(12) United States Patent
Baeuerle et al.

(10) Patent No.: US 12,084,518 B2
(45) Date of Patent: *Sep. 10, 2024

(54) TRISPECIFIC BINDING PROTEINS AND METHODS OF USE

(71) Applicant: Harpoon Therapeutics, Inc., South San Francisco, CA (US)

(72) Inventors: Patrick Baeuerle, Gauting (DE); Luke Evnin, San Francisco, CA (US); Jeanmarie Guenot, San Francisco, CA (US); Vanitha Ramakrishnan, Belmont, CA (US); Holger Wesche, San Francisco, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 862 days.

This patent is subject to a terminal disclaimer.

(21) Appl. No.: 17/165,760

(22) Filed: Feb. 2, 2021

(65) Prior Publication Data

US 2021/0179735 A1 Jun. 17, 2021

Related U.S. Application Data

(63) Continuation of application No. 15/630,259, filed on Jun. 22, 2017, now Pat. No. 10,954,311, which is a continuation of application No. 15/160,984, filed on May 20, 2016, now Pat. No. 9,708,412.

(60) Provisional application No. 62/305,088, filed on Mar. 8, 2016, provisional application No. 62/165,833, filed on May 22, 2015, provisional application No. 62/165,153, filed on May 21, 2015.

(51) Int. Cl.
*A61K 39/395* (2006.01)
*C07K 16/18* (2006.01)
*C07K 16/28* (2006.01)
*C07K 16/30* (2006.01)
*C07K 16/46* (2006.01)

(52) U.S. Cl.
CPC ............ *C07K 16/468* (2013.01); *C07K 16/18* (2013.01); *C07K 16/2809* (2013.01); *C07K 16/3069* (2013.01); *C07K 2317/31* (2013.01); *C07K 2317/569* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 4,816,567 A | 3/1989 | Cabilly et al. |
|---|---|---|
| 4,943,533 A | 7/1990 | Mendelsohn et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,811,097 A | 9/1998 | Allison et al. |
| 5,840,526 A | 11/1998 | Casterman et al. |
| 5,843,439 A | 12/1998 | Anderson et al. |
| 5,844,093 A | 12/1998 | Kettleborough et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 5,977,318 A | 11/1999 | Linsley et al. |
| 6,005,079 A | 12/1999 | Casterman et al. |
| 6,015,695 A | 1/2000 | Casterman et al. |
| 6,051,227 A | 4/2000 | Allison et al. |
| 6,107,090 A | 8/2000 | Bander |
| 6,120,766 A | 9/2000 | Hale et al. |
| 6,136,311 A | 10/2000 | Bander |
| 6,210,669 B1 | 4/2001 | Aruffo et al. |
| 6,303,121 B1 | 10/2001 | Kwon |
| 6,326,193 B1 | 12/2001 | Liu et al. |
| 6,331,415 B1 | 12/2001 | Cabilly et al. |
| 6,352,694 B1 | 3/2002 | June et al. |
| 6,355,476 B1 | 3/2002 | Kwon et al. |
| 6,362,325 B1 | 3/2002 | Kwon |
| 6,407,213 B1 | 6/2002 | Carter et al. |
| 6,534,055 B1 | 3/2003 | June et al. |
| 6,548,640 B1 | 4/2003 | Winter |

(Continued)

FOREIGN PATENT DOCUMENTS

| CA | 2992797 A1 | 2/2017 |
|---|---|---|
| CA | 2994579 A1 | 2/2017 |

(Continued)

OTHER PUBLICATIONS

Almagro & Fransson, Frontiers in Bioscience 2008 (Year: 2008).*

(Continued)

*Primary Examiner* — Meera Natarajan
(74) *Attorney, Agent, or Firm* — WILSON SONSINI GOODRICH & ROSATI

(57) ABSTRACT

Provided herein are trispecific antigen-binding proteins comprising a domain binding to CD3, a half-life extension domain, and a domain binding to a target antigen. Also provided are pharmaceutical compositions thereof, as well as nucleic acids, recombinant expression vectors and host cells for making such trispecific antigen-binding proteins. Also disclosed are methods of using the disclosed trispecific antigen-binding proteins in the prevention, and/or treatment diseases, conditions and disorders.

21 Claims, 13 Drawing Sheets

Specification includes a Sequence Listing.

(56) References Cited

U.S. PATENT DOCUMENTS

| | | |
|---|---|---|
| 6,569,997 B1 | 5/2003 | Kwon |
| 6,670,453 B2 | 12/2003 | Frenken et al. |
| 6,682,736 B1 | 1/2004 | Hanson et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,808,710 B1 | 10/2004 | Wood et al. |
| 6,867,041 B2 | 3/2005 | Berenson et al. |
| 6,887,466 B2 | 5/2005 | June et al. |
| 6,887,673 B2 | 5/2005 | Kunkel et al. |
| 6,905,680 B2 | 6/2005 | June et al. |
| 6,905,681 B1 | 6/2005 | June et al. |
| 6,905,685 B2 | 6/2005 | Kwon |
| 6,905,874 B2 | 6/2005 | Berenson et al. |
| 6,974,863 B2 | 12/2005 | Kwon |
| 6,984,720 B1 | 1/2006 | Korman et al. |
| 7,034,121 B2 | 4/2006 | Carreno et al. |
| 7,060,808 B1 | 6/2006 | Goldstein et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,214,493 B2 | 5/2007 | Kunkel et al. |
| 7,232,566 B2 | 6/2007 | June et al. |
| 7,247,301 B2 | 7/2007 | Van De Winkel et al. |
| 7,262,276 B2 | 8/2007 | Huang et al. |
| 7,288,638 B2 | 10/2007 | Jure-Kunkel et al. |
| 7,488,802 B2 | 2/2009 | Collins et al. |
| 7,595,378 B2 | 9/2009 | Van De Winkel et al. |
| 7,605,238 B2 | 10/2009 | Korman et al. |
| 7,666,414 B2 | 2/2010 | Bander |
| 7,723,484 B2 | 5/2010 | Beidler et al. |
| 7,807,162 B2 | 10/2010 | Silence |
| 7,812,135 B2 | 10/2010 | Smith et al. |
| 7,850,971 B2 | 12/2010 | Maddon et al. |
| 7,939,072 B2 | 5/2011 | Yarden et al. |
| 7,943,743 B2 | 5/2011 | Korman et al. |
| 8,008,449 B2 | 8/2011 | Korman et al. |
| 8,114,965 B2 | 2/2012 | Maddon et al. |
| 8,153,768 B2 | 4/2012 | Kunz et al. |
| 8,168,757 B2 | 5/2012 | Finnefrock et al. |
| 8,188,223 B2 | 5/2012 | Beirnaert et al. |
| 8,236,308 B2 | 8/2012 | Kischel et al. |
| 8,354,509 B2 | 1/2013 | Carven et al. |
| 8,388,967 B2 | 3/2013 | Smith et al. |
| 8,470,330 B2 | 6/2013 | Schuelke et al. |
| 8,552,156 B2 | 10/2013 | Takayanagi et al. |
| 8,609,089 B2 | 12/2013 | Langermann et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,709,424 B2 | 4/2014 | Schebye et al. |
| 8,779,105 B2 | 7/2014 | Korman et al. |
| 8,784,821 B1 | 7/2014 | Kufer et al. |
| 8,846,042 B2 | 9/2014 | Zhou |
| 8,900,587 B2 | 12/2014 | Carven et al. |
| 8,907,071 B2 | 12/2014 | Sullivan et al. |
| 8,937,164 B2 | 1/2015 | Descamps et al. |
| 8,986,972 B2 | 3/2015 | Stull et al. |
| 9,089,615 B2 | 7/2015 | Stull et al. |
| 9,089,616 B2 | 7/2015 | Stull et al. |
| 9,089,617 B2 | 7/2015 | Stull et al. |
| 9,090,683 B2 | 7/2015 | Stull et al. |
| 9,107,961 B2 | 8/2015 | Stull et al. |
| 9,126,984 B2 | 9/2015 | Crosignani et al. |
| 9,127,071 B2 | 9/2015 | Yoshida et al. |
| 9,133,271 B1 | 9/2015 | Stull et al. |
| 9,155,803 B1 | 10/2015 | Stull et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,334,318 B1 | 5/2016 | Stull et al. |
| 9,340,621 B2 | 5/2016 | Kufer et al. |
| 9,345,787 B2 | 5/2016 | Hemminki et al. |
| 9,352,051 B1 | 5/2016 | Stull et al. |
| 9,353,182 B2 | 5/2016 | Stull et al. |
| 9,358,304 B1 | 6/2016 | Stull et al. |
| 9,359,442 B2 | 6/2016 | Hoffee et al. |
| 9,422,368 B2 | 8/2016 | Spee et al. |
| 9,480,757 B2 | 11/2016 | Stull et al. |
| 9,481,724 B2 | 11/2016 | Ravetch et al. |
| 9,486,537 B2 | 11/2016 | Stull et al. |
| 9,624,185 B1 | 4/2017 | Xu |
| 9,642,918 B2 | 5/2017 | Bruederle et al. |
| 9,708,412 B2 | 7/2017 | Baeuerle et al. |
| 9,764,042 B1 | 9/2017 | Stull et al. |
| 9,770,518 B1 | 9/2017 | Stull et al. |
| 9,775,916 B1 | 10/2017 | Stull et al. |
| 9,855,343 B2 | 1/2018 | Stull et al. |
| 9,861,708 B2 | 1/2018 | Stull et al. |
| 9,867,887 B1 | 1/2018 | Stull et al. |
| 9,878,053 B2 | 1/2018 | Stull et al. |
| 9,920,115 B2 | 3/2018 | Dubridge et al. |
| 9,931,420 B2 | 4/2018 | Stull et al. |
| 9,931,421 B2 | 4/2018 | Stull et al. |
| 9,937,268 B2 | 4/2018 | Stull et al. |
| 10,066,016 B2 | 9/2018 | Dubridge et al. |
| 10,100,106 B2 | 10/2018 | Dubridge et al. |
| 10,137,204 B2 | 11/2018 | Stull et al. |
| 10,428,120 B2 | 10/2019 | Kontermann et al. |
| 10,543,271 B2 | 1/2020 | Wesche et al. |
| 10,544,221 B2 | 1/2020 | Dubridge et al. |
| 10,730,954 B2 | 8/2020 | Wesche et al. |
| 10,815,311 B2 | 10/2020 | Wesche et al. |
| 10,844,134 B2 | 11/2020 | Baeuerle et al. |
| 10,849,973 B2 | 12/2020 | Dubridge et al. |
| 10,927,180 B2 | 2/2021 | Wesche et al. |
| 10,954,311 B2 | 3/2021 | Baeuerle et al. |
| 11,111,311 B2 | 9/2021 | Yoshida et al. |
| 11,136,403 B2 | 10/2021 | Wesche et al. |
| 11,180,563 B2 | 11/2021 | Wesche et al. |
| 2002/0015704 A1 | 2/2002 | Bander |
| 2002/0051780 A1 | 5/2002 | Lindhofer et al. |
| 2002/0081296 A1 | 6/2002 | Theill et al. |
| 2003/0031673 A1 | 2/2003 | Bander |
| 2003/0092892 A1 | 5/2003 | Frenken et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0095244 A1 | 5/2005 | Jure-Kunkel et al. |
| 2005/0100543 A1 | 5/2005 | Hansen et al. |
| 2005/0175606 A1 | 8/2005 | Huang et al. |
| 2006/0034810 A1 | 2/2006 | Riley et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0028880 A1 | 1/2009 | Beirnaert et al. |
| 2009/0041789 A1 | 2/2009 | Elsaesser-Beile et al. |
| 2009/0117108 A1 | 5/2009 | Wang et al. |
| 2009/0136485 A1 | 5/2009 | Chu et al. |
| 2009/0136494 A1 | 5/2009 | Ponath et al. |
| 2009/0252683 A1 | 10/2009 | Kischel et al. |
| 2009/0259026 A1 | 10/2009 | Tomlinson et al. |
| 2010/0022452 A1 | 1/2010 | Silence |
| 2010/0028330 A1 | 2/2010 | Collins et al. |
| 2010/0122358 A1 | 5/2010 | Bruggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0150892 A1 | 6/2011 | Thudium et al. |
| 2011/0165621 A1 | 7/2011 | Dreier et al. |

(56) References Cited

U.S. PATENT DOCUMENTS

| | | |
|---|---|---|
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0039906 A1 | 2/2012 | Olive |
| 2012/0114649 A1 | 5/2012 | Langermann et al. |
| 2012/0231024 A1 | 9/2012 | Elsaesser-Beile et al. |
| 2012/0237977 A1 | 9/2012 | Daugherty et al. |
| 2012/0263677 A1 | 10/2012 | Eagle et al. |
| 2012/0328619 A1 | 12/2012 | Fey et al. |
| 2013/0017199 A1 | 1/2013 | Langermann |
| 2013/0017200 A1 | 1/2013 | Scheer et al. |
| 2013/0136744 A1 | 5/2013 | Bouche et al. |
| 2013/0183321 A1 | 7/2013 | Smith et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0315906 A1 | 11/2013 | Lowman et al. |
| 2013/0330335 A1 | 12/2013 | Bremel et al. |
| 2014/0004121 A1 | 1/2014 | Fanslow, III et al. |
| 2014/0004575 A1 | 1/2014 | Ito et al. |
| 2014/0023664 A1 | 1/2014 | Lowman et al. |
| 2014/0044728 A1 | 2/2014 | Takayanagi et al. |
| 2014/0045195 A1 | 2/2014 | Daugherty et al. |
| 2014/0065152 A1 | 3/2014 | Kwon |
| 2014/0072565 A1 | 3/2014 | Kwon |
| 2014/0072566 A1 | 3/2014 | Kwon |
| 2014/0073767 A1 | 3/2014 | Lee et al. |
| 2014/0088295 A1 | 3/2014 | Smith et al. |
| 2014/0093511 A1 | 4/2014 | Lonberg et al. |
| 2014/0161828 A1 | 6/2014 | Armitage et al. |
| 2014/0205601 A1 | 7/2014 | Beirnaert et al. |
| 2014/0220002 A1 | 8/2014 | Ponte et al. |
| 2014/0242075 A1 | 8/2014 | Parren et al. |
| 2014/0302037 A1 | 10/2014 | Borges et al. |
| 2014/0308285 A1 | 10/2014 | Yan et al. |
| 2014/0322218 A1 | 10/2014 | Xiao et al. |
| 2014/0348841 A1 | 11/2014 | Schebye et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0079109 A1 | 3/2015 | Li et al. |
| 2015/0093336 A1 | 4/2015 | Van Ginderachter et al. |
| 2015/0174268 A1 | 6/2015 | Li et al. |
| 2015/0175697 A1 | 6/2015 | Bonvini et al. |
| 2015/0183875 A1 | 7/2015 | Cobbold et al. |
| 2015/0225367 A1 | 8/2015 | Crosignani et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2015/0328332 A1 | 11/2015 | Stull et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0046724 A1 | 2/2016 | Brogdon et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0185875 A1 | 6/2016 | Cheng et al. |
| 2016/0194399 A1 | 7/2016 | Irving et al. |
| 2016/0215063 A1 | 7/2016 | Bernett et al. |
| 2016/0229913 A1 | 8/2016 | Bosques et al. |
| 2016/0251438 A1 | 9/2016 | Lucas et al. |
| 2016/0251440 A1 | 9/2016 | Roobrouck et al. |
| 2016/0257721 A1 | 9/2016 | Lieber et al. |
| 2016/0263087 A1 | 9/2016 | Crosignani et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037130 A1 | 2/2017 | Raum et al. |
| 2017/0037149 A1 | 2/2017 | Raum et al. |
| 2017/0051068 A1 | 2/2017 | Pillarisetti et al. |
| 2017/0152316 A1 | 6/2017 | Cobbold et al. |
| 2017/0158771 A1 | 6/2017 | Glennie et al. |
| 2017/0204164 A1 | 7/2017 | Himmler et al. |
| 2017/0274094 A1 | 9/2017 | Stull et al. |
| 2017/0275373 A1 | 9/2017 | Kufer et al. |
| 2017/0306014 A1 | 10/2017 | Cornen et al. |
| 2017/0334979 A1 | 11/2017 | Dubridge et al. |
| 2017/0334997 A1 | 11/2017 | Dubridge et al. |
| 2017/0349660 A1 | 12/2017 | Saville et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0036306 A1 | 2/2018 | Jones et al. |
| 2018/0134789 A1 | 5/2018 | Baeuerle et al. |
| 2018/0148508 A1 | 5/2018 | Wang et al. |
| 2018/0318417 A1 | 11/2018 | Schuetz et al. |
| 2018/0326060 A1 | 11/2018 | Wesche et al. |
| 2018/0327511 A1 | 11/2018 | Satoh et al. |
| 2018/0346601 A1 | 12/2018 | Dettling et al. |
| 2019/0016811 A1 | 1/2019 | Lucas et al. |
| 2019/0023786 A1 | 1/2019 | Broderick et al. |
| 2019/0031749 A1 | 1/2019 | Dubridge et al. |
| 2019/0046656 A1 | 2/2019 | Stull et al. |
| 2019/0062427 A1 | 2/2019 | Rosenthal et al. |
| 2019/0092862 A1 | 3/2019 | Cui et al. |
| 2019/0112381 A1 | 4/2019 | Wesche et al. |
| 2019/0127483 A1 | 5/2019 | Li |
| 2019/0225702 A1 | 7/2019 | Baeuerle et al. |
| 2019/0247510 A1 | 8/2019 | Stull et al. |
| 2020/0115461 A1 | 4/2020 | Evnin et al. |
| 2020/0148771 A1 | 5/2020 | Paeuerle et al. |
| 2020/0155520 A1 | 5/2020 | Colburn et al. |
| 2020/0231672 A1 | 7/2020 | Dubridge et al. |
| 2020/0270362 A1 | 8/2020 | Wesche et al. |
| 2020/0289646 A1 | 9/2020 | Wesche et al. |
| 2020/0352998 A1 | 11/2020 | Albertson et al. |
| 2021/0047439 A1 | 2/2021 | Wesche et al. |
| 2021/0095047 A1 | 4/2021 | Baeuerle et al. |
| 2021/0100902 A1 | 4/2021 | Dubridge et al. |
| 2021/0171649 A1 | 6/2021 | Wesche et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0355219 A1 | 11/2021 | Lin et al. |
| 2021/0380715 A1 | 12/2021 | Yoshida et al. |
| 2022/0017626 A1 | 1/2022 | Wesche et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |
| 2022/0267462 A1 | 8/2022 | Wesche et al. |
| 2023/0257451 A1 | 8/2023 | Dubridge et al. |
| 2024/0084009 A1 | 3/2024 | Dubridge et al. |
| 2024/0084035 A1 | 3/2024 | Molloy et al. |
| 2024/0100157 A1 | 3/2024 | Wesche et al. |

FOREIGN PATENT DOCUMENTS

| | | |
|---|---|---|
| CA | 3040823 A1 | 4/2018 |
| CN | 1563092 A | 1/2005 |
| CN | 101098891 A | 1/2008 |
| CN | 101557817 A | 10/2009 |
| CN | 101646689 A | 2/2010 |
| CN | 101809035 A | 8/2010 |
| CN | 104520324 A | 4/2015 |
| CN | 108026174 A | 5/2018 |
| CN | 108137706 A | 6/2018 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| EP | 2581113 A1 | 4/2013 |
| EP | 2817338 A2 | 12/2014 |
| EP | 3093293 A1 | 11/2016 |

(56) References Cited

FOREIGN PATENT DOCUMENTS

| | | | |
|---|---|---|---|
| EP | 3093294 A1 | 11/2016 |
| EP | 3095797 A1 | 11/2016 |
| EP | 3146979 A1 | 3/2017 |
| EP | 3337517 A2 | 6/2018 |
| EP | 3193929 B1 | 6/2019 |
| EP | 3556400 A1 | 10/2019 |
| FR | 901228 A | 7/1945 |
| JP | 2005501517 A | 1/2005 |
| JP | 2005518789 A | 6/2005 |
| JP | 2007535915 A | 12/2007 |
| JP | 2008278814 A | 11/2008 |
| JP | 2015501135 A | 1/2015 |
| JP | 2015528003 A | 9/2015 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0130381 A2 | 5/2001 |
| WO | WO-0190190 A2 | 11/2001 |
| WO | WO-0196584 A2 | 12/2001 |
| WO | WO-0222685 A2 | 3/2002 |
| WO | WO-02055082 A1 | 7/2002 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004035607 A2 | 4/2004 |
| WO | WO-2004041867 A2 | 5/2004 |
| WO | WO-2004042404 A1 | 5/2004 |
| WO | WO-2004049794 A2 | 6/2004 |
| WO | WO-2004056312 A2 | 7/2004 |
| WO | WO-2004099249 A2 | 11/2004 |
| WO | WO-2005003168 A2 | 1/2005 |
| WO | WO-2005009465 A1 | 2/2005 |
| WO | WO-2005040220 A1 | 5/2005 |
| WO | WO-2005095456 A1 | 10/2005 |
| WO | WO-2006020258 A2 | 2/2006 |
| WO | WO-2006072620 A1 | 7/2006 |
| WO | WO-2006072625 A2 | 7/2006 |
| WO | WO-2006072626 A1 | 7/2006 |
| WO | WO-2006105021 A2 | 10/2006 |
| WO | WO-2006121168 A1 | 11/2006 |
| WO | WO-2006122786 A2 | 11/2006 |
| WO | WO-2006122787 A1 | 11/2006 |
| WO | WO-2007005874 A2 | 1/2007 |
| WO | WO-2007024715 A2 | 3/2007 |
| WO | WO-2007042261 A2 | 4/2007 |
| WO | WO-2007042573 A2 | 4/2007 |
| WO | WO-2007062466 A1 | 6/2007 |
| WO | WO-2007113648 A2 | 10/2007 |
| WO | WO-2007115230 A2 | 10/2007 |
| WO | WO-2008028977 A2 | 3/2008 |
| WO | WO-2008084106 A1 | 7/2008 |
| WO | WO-2009009116 A2 | 1/2009 |
| WO | WO-2009025846 A2 | 2/2009 |
| WO | WO-2009030285 A1 | 3/2009 |
| WO | WO-2009035577 A1 | 3/2009 |
| WO | WO-2009101611 A1 | 8/2009 |
| WO | WO-2009114335 A2 | 9/2009 |
| WO | WO-2009147248 A2 | 12/2009 |
| WO | WO-2010003118 A1 | 1/2010 |
| WO | WO-2010012557 A1 | 2/2010 |
| WO | WO-2010019570 A2 | 2/2010 |
| WO | WO-2010027827 A2 | 3/2010 |
| WO | WO-2010037836 A2 | 4/2010 |
| WO | WO-2010037837 A2 | 4/2010 |
| WO | WO-2010065939 A1 | 6/2010 |
| WO | WO-2010077634 A1 | 7/2010 |
| WO | WO-2010081173 A2 | 7/2010 |
| WO | WO-2011028683 A1 | 3/2011 |
| WO | WO-2011039368 A2 | 4/2011 |
| WO | WO-2011051327 A2 | 5/2011 |
| WO | WO-2011066342 A2 | 6/2011 |
| WO | WO-2011070024 A1 | 6/2011 |
| WO | WO-2011079283 A1 | 6/2011 |
| WO | WO-2011107553 A1 | 9/2011 |
| WO | WO-2011131407 A1 | 10/2011 |
| WO | WO-2011140249 A2 | 11/2011 |
| WO | WO-2011155607 A1 | 12/2011 |
| WO | WO-2011161260 A1 | 12/2011 |
| WO | WO-2012071411 A2 | 5/2012 |
| WO | WO-2012122444 A1 | 9/2012 |
| WO | WO-2012131053 A1 | 10/2012 |
| WO | WO-2012138475 A1 | 10/2012 |
| WO | WO-2012145493 A1 | 10/2012 |
| WO | WO-2012158818 A2 | 11/2012 |
| WO | WO-2012160448 A2 | 11/2012 |
| WO | WO-2012163805 A1 | 12/2012 |
| WO | WO-2012175400 A1 | 12/2012 |
| WO | WO-2013006490 A2 | 1/2013 |
| WO | WO-2013036130 A1 | 3/2013 |
| WO | WO-2013039954 A1 | 3/2013 |
| WO | WO-2013045707 A2 | 4/2013 |
| WO | WO-2013053725 A1 | 4/2013 |
| WO | WO-2013072406 A1 | 5/2013 |
| WO | WO-2013072415 A1 | 5/2013 |
| WO | WO-2013079174 A1 | 6/2013 |
| WO | WO-2013087699 A1 | 6/2013 |
| WO | WO-2013104804 A2 | 7/2013 |
| WO | WO-2013110531 A1 | 8/2013 |
| WO | WO-2013119716 A1 | 8/2013 |
| WO | WO-2013126712 A1 | 8/2013 |
| WO | WO-2013128027 A1 | 9/2013 |
| WO | WO-2013132044 A1 | 9/2013 |
| WO | WO-2013158856 A2 | 10/2013 |
| WO | WO-2013169264 A1 | 11/2013 |
| WO | WO-2013173223 A1 | 11/2013 |
| WO | WO-2014008218 A1 | 1/2014 |
| WO | WO-2014012085 A2 | 1/2014 |
| WO | WO-2014033304 A2 | 3/2014 |
| WO | WO-2014036357 A1 | 3/2014 |
| WO | WO-2014047231 A1 | 3/2014 |
| WO | WO-2014055648 A1 | 4/2014 |
| WO | WO-2014094122 A1 | 6/2014 |
| WO | WO-2014125273 A1 | 8/2014 |
| WO | WO-2014132072 A1 | 9/2014 |
| WO | WO-2014138306 A1 | 9/2014 |
| WO | WO-2014140358 A1 | 9/2014 |
| WO | WO-2014151910 A1 | 9/2014 |
| WO | WO-2014153270 A1 | 9/2014 |
| WO | WO-2015026684 A1 | 2/2015 |
| WO | WO-2015031667 A2 | 3/2015 |
| WO | WO-2015031693 A1 | 3/2015 |
| WO | WO-2015042246 A1 | 3/2015 |
| WO | WO-2015082499 A2 | 6/2015 |
| WO | WO-2015103072 A1 | 7/2015 |
| WO | WO-2015121812 A1 | 8/2015 |
| WO | WO-2015127407 A1 | 8/2015 |
| WO | WO-2015140717 A1 | 9/2015 |
| WO | WO-2015142675 A2 | 9/2015 |
| WO | WO-2015146437 A1 | 10/2015 |
| WO | WO-2015150097 A1 | 10/2015 |
| WO | WO-2015150327 A1 | 10/2015 |
| WO | WO-2015150447 A1 | 10/2015 |
| WO | WO-2015173764 A1 | 11/2015 |
| WO | WO-2015184099 A1 | 12/2015 |
| WO | WO-2015184207 A1 | 12/2015 |
| WO | WO-2015187835 A2 | 12/2015 |
| WO | WO-2016009029 A1 | 1/2016 |
| WO | WO-2016026772 A1 | 2/2016 |
| WO | WO-2016032334 A1 | 3/2016 |
| WO | WO-2016046778 A2 | 3/2016 |
| WO | WO-2016055551 A1 | 4/2016 |
| WO | WO-2016071283 A1 | 5/2016 |
| WO | WO-2016071293 A2 | 5/2016 |
| WO | WO-2016075099 A1 | 5/2016 |
| WO | WO-2016087531 A1 | 6/2016 |
| WO | WO-2016105450 A2 | 6/2016 |
| WO | WO-2016125017 A1 | 8/2016 |
| WO | WO-2016130819 A2 | 8/2016 |

(56) References Cited

FOREIGN PATENT DOCUMENTS

| | | |
|---|---|---|
| WO | WO-2016134333 A1 | 8/2016 |
| WO | WO-2016134335 A2 | 8/2016 |
| WO | WO-2016138038 A1 | 9/2016 |
| WO | WO-2016147144 A1 | 9/2016 |
| WO | WO-2016171999 A2 | 10/2016 |
| WO | WO-2016179003 A1 | 11/2016 |
| WO | WO-2016179518 A2 | 11/2016 |
| WO | WO-2016180982 A1 | 11/2016 |
| WO | WO-2016181348 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017007700 A1 | 1/2017 |
| WO | WO-2017021349 A1 | 2/2017 |
| WO | WO-2017025038 A1 | 2/2017 |
| WO | WO-2017025698 A1 | 2/2017 |
| WO | WO-2017025868 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017093969 A1 | 6/2017 |
| WO | WO-2017134134 A1 | 8/2017 |
| WO | WO-2017136549 A1 | 8/2017 |
| WO | WO-2017156178 A1 | 9/2017 |
| WO | WO-2017157305 A1 | 9/2017 |
| WO | WO-2017161206 A1 | 9/2017 |
| WO | WO-2017162587 A1 | 9/2017 |
| WO | WO-2017201442 A1 | 11/2017 |
| WO | WO-2017201488 A1 | 11/2017 |
| WO | WO-2017201493 A1 | 11/2017 |
| WO | WO-2017220988 A1 | 12/2017 |
| WO | WO-2018017863 A1 | 1/2018 |
| WO | WO-2018017864 A2 | 1/2018 |
| WO | WO-2018026953 A1 | 2/2018 |
| WO | WO-2018027203 A1 | 2/2018 |
| WO | WO-2018033798 A1 | 2/2018 |
| WO | WO-2018048975 A1 | 3/2018 |
| WO | WO-2018071777 A1 | 4/2018 |
| WO | WO-2018075359 A1 | 4/2018 |
| WO | WO-2018083204 A1 | 5/2018 |
| WO | WO-2018085469 A2 | 5/2018 |
| WO | WO-2018098354 A1 | 5/2018 |
| WO | WO-2018098356 A1 | 5/2018 |
| WO | WO-2018106529 A1 | 6/2018 |
| WO | WO-2018106588 A1 | 6/2018 |
| WO | WO-2018110555 A1 | 6/2018 |
| WO | WO-2018115859 A1 | 6/2018 |
| WO | WO-2018119183 A2 | 6/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018183366 A1 | 10/2018 |
| WO | WO-2018204717 A1 | 11/2018 |
| WO | WO-2018209298 A1 | 11/2018 |
| WO | WO-2018209304 A1 | 11/2018 |
| WO | WO-2019011852 A1 | 1/2019 |
| WO | WO-2019011855 A1 | 1/2019 |
| WO | WO-2019025983 A1 | 2/2019 |
| WO | WO-2019075359 A1 | 4/2019 |
| WO | WO-2019075378 A1 | 4/2019 |
| WO | WO-2019136305 A1 | 7/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2019246004 A1 | 12/2019 |
| WO | WO-2020053263 A1 | 3/2020 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020092792 A2 | 5/2020 |
| WO | WO-2020097403 A1 | 5/2020 |
| WO | WO-2019166650 A9 | 8/2020 |
| WO | WO-2020181145 A1 | 9/2020 |
| WO | WO-2020232303 A1 | 11/2020 |
| WO | WO-2020252349 A1 | 12/2020 |
| WO | WO-2020261093 A1 | 12/2020 |
| WO | WO-2020263830 A1 | 12/2020 |
| WO | WO-2021097060 A1 | 5/2021 |
| WO | WO-2021168303 A1 | 8/2021 |
| WO | WO-2021231434 A1 | 11/2021 |
| WO | WO-2022031884 A2 | 2/2022 |
| WO | WO-2022032006 A2 | 2/2022 |
| WO | WO-2022098909 A1 | 5/2022 |
| WO | WO-2022212732 A1 | 10/2022 |
| WO | WO-2022256498 A1 | 12/2022 |
| WO | WO-2022256499 A2 | 12/2022 |
| WO | WO-2022256500 A2 | 12/2022 |
| WO | WO-2022272033 A2 | 12/2022 |
| WO | WO-2023064945 A2 | 4/2023 |

OTHER PUBLICATIONS

De Genst et al., Dev Comp Immunol 2006; 30:187-98 (Year: 2006).*
Yoshinaga et al., J. Biochem 2008; 143:593-601 (Year: 2008).*
Annual Report Pursuant to Section 13 or 15(d) of the Securities Exchange Act of 1934. 2019 22-24 [online]. [Retrieved on Aug. 5, 2021]. Retrieved from website URL:https://www.annualreports.com/HostedData/AnnualReportArchive/h/NASDAQ_HARP_2018.pdf.
Hassanzadeh-Ghassabeh et al. Nanobodies and their potential applications. Nanomedicine 8(6):1013-1026 (2013).
Krzywinska et al. CD45 Isoform Profile Identifies Natural Killer (NK) Subsets with Differential Activity. PLoS One 11(4):e0150434 (2016).
Leibl et al. Ovarian granulosa cell tumors frequently express EGFR (Her-1), Her-3, and Her-4: An immunohistochemical study. Gynecol Oncol 101(1):18-23 (2006).
Mason et al. CD79a: a novel marker for B-cell neoplasms in routinely processed tissue samples. Blood 86(4):1453-1459 (1995).
PCT/US2021/018853 International Search Report and Written Opinion dated Jul. 8, 2021.
PCT/US2021/031790 International Search Report and Written Opinion dated Sep. 16, 2021.
Sandler et al. Nondermatologic adverse events associated with anti-EGFR therapy. Oncology (Williston Park) 20(5 Suppl 2):35-40 (2006).
Thomas. Cetuximab: adverse event profile and recommendations for toxicity management. Clin J Oncol Nurs. 9(3):332-8 (2005).
UniProtKB Accession No. A0A3M1V7M7_9EURY, Ig-like_bact domain-containing protein, Feb. 13, 2019 [online] [Retrieved on Jun. 8, 2021]. Retrieved from the internet < url: < a href="https://www.uniprotorg/uniprot/A0A3M1V7M7.bct" > https://www.uniprotorg/uniprot/A0A3M1V7M7.bct < /url:. < a >.
U.S. Appl. No. 16/161,986 Office Action dated Dec. 2, 2021.
Balzar et al. The biology of the 17-1A antigen (Ep-CAM). J. Mol. Med. 77:699-712 (1999).
Chaubal et al. Ep-CAM—a marker for the detection of disseminated tumor cells in patients suffering from SCCHN. Anticancer Res 19:2237-2242 (1999).
Davé et al. Fab-dsFv: A bispecific antibody format with extended serum half-life through albumin binding. MAbs 8(7):1319-1335 (2016).
Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).

(56) References Cited

OTHER PUBLICATIONS

Kim et al. Strategies and 1-17 Advancement in Antibody-Drug Conjugate Optimization for Targeted Cancer Therapeutics. Biomol Ther (Seoul) 23(6):493-509 (2015).
Koprowski et al. Colorectal carcinoma antigens detected by hybridoma antibodies. Somatic Cell Genet. 5:957-971 (1979).
Lehmann et al. Stability engineering of anti-EGFR scFv antibodies by rational design of a lambda-to-kappa swap of the VL framework using a structure-guided approach. MAbs 7(6):1058-1071 (2015).
Lin et al. Improved affinity of a chicken single-chain antibody to avian infectious bronchitis virus by site-directed mutagenesis of complementarity-determining region H3. African Journal of Biotechnology 10(79):18294-18302 (2011).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Lucchi et al. The Masking Game: Design of Activatable Antibodies and Mimetics for Selective Thera-peutics Cell Control. ACS Cent Sci 7(5):724-738 (2021).
McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
McCarthy et al. Altering the fine specificity of an anti-Legionella single chain antibody by a single amino acid insertion. J Immunol Methods 251(1-2):137-49 (2001).
Osta et al. EpCAM is overexpressed in breast cancer and is a potential target for breast cancer gene therapy. Cancer Res 64:5818-24 (2004).
PCT/US2021/058108 International Search Report and Written Opinion dated Apr. 1, 2022.
Piyathilake et al. The expression of Ep-CAM (17-1A) in squamous cell cancers of the lung. Hum Pathol. 31:482-487 (2000).
Quak et al. Production of a monoclonal antibody (K 931) to a squamous cell carcinoma associated antigen identified as the 17-1A antigen. Hybridoma 9:377-387 (1990).
Simon et al. Epithelial glycoprotein is a member of a family of epithelial cell surface antigens homologous to nidogen, a matrix adhesion protein. PNAS USA 87:2755-2759 (1990).
Trail et al. Antibody drug 1-17 conjugates for treatment of breast cancer: Novel targets and diverse approaches in ADC design. Pharmacol Ther 181:126-142 (2018).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
U.S. Appl. No. 16/339,263 Office Action dated Jan. 11, 2022.
U.S. Appl. No. 16/489,523 Office Action dated Feb. 14, 2022.
U.S. Appl. No. 16/773,843 Office Action dated Feb. 8, 2022.
PCT/US2022/078178 International Search Report and Written Opinion dated Jul. 18, 2023.
U.S. Appl. No. 17/072,370 Office Action dated Jun. 2, 2023.
Allard et al., The ectonucleotidases CD39 and CD73: Novel checkpoint inhibitor targets. Immunol Rev., 276(1):121-144 (2018).
Altenhofer et al., The NOX toolbox: validating the role of NADPH oxidases in physiology and disease. Cell Mol Life Sciences 69(14):2327-2343 (2012).
Austin et al. TriTACs, a Novel Class of T-Cell-Engaging Protein Constructs Designed for the Treatment of Solid Tumors. Mol Cancer Ther 20(1):109-120 (2021).
Ayers et al. IFN-γ-related mRNA profile predicts clinical response to PD-1 blockade. The Journal of Clinical Investigation 127(8):2930-2940 (Aug. 2017).
Balzar et al. Epidermal growth factor-like repeats mediate lateral and reciprocal interactions of Ep-CAM molecules in homophilic adhesions. Mol Cell Biol. 21(7):2570-80 (2001).

Bluemel et al. Epitope distance to the target cell membrane and antigen size determine the potency of T cell-mediated lysis by BiTE antibodies specific for a large melanoma surface antigen. Cancer Immunol Immunother 59(8): 1197-209 (2010).
Cheong et al., A patent review of IDO1 inhibitors for cancer. Expert Opin Ther Pat. 28(4):317-330 (2018).
Croso et al., Real-time detection of mesothelin in pancreatic cancer cell line supernatant using an acoustic wave immunosensor. Cancer Detect. Prev. 30:180-187 (2006).
Dickopf et al. Format and geometries matter: Structure-based design defines the functionality of bispecific antibodies. Comput Struct Biotechnol J 18:1221-1227 (2020).
Fang et al. Characterization of an anti-human ovarian carcinomaxantihuman CD3 bispecific single-chain antibody with an albumin-original interlinker. Gynecol Oncol 92(1):135-146 (2004).
Gautam et al., Dual Inhibition of NOX2 and Receptor Tyrosine Kinase by BJ-1301 Enhances Anticancer Therapy Efficacy via Suppression of Autocrine-Stimulatory Factors in Lung Cancer. Mol Cancer Ther 16(10):2144-2156 (2017).
Gianni et al., A novel and specific NADPH oxidase-1 (Nox1) small-molecule inhibitor blocks the formation of functional invadopodia in human colon cancer cells. ACS Chem Biol 5(10):981-93 (2010).
Gorshkova et al. Single domain antibodies and bioengineering drugs on their basis: new opportunities for diagnostics and therapy. Medical Immunology (Russia) 18(6):505-520 (2016) (English Abstract).
Harris et al. A bispecific antibody agonist of the IL-2 heterodimeric receptor preferentially promotes in vivo expansion of CD8 and NK cells. Sci Rep. 11(1):10592 (2021).
Jang et al. Human 4-1BB (CD137) signals are mediated by TRAF2 and activate nuclear factor-kappa B. Biochem. Biophys. Res. Commun. 242 (3):613-20 (1998).
Julian et al. Efficient affinity maturation of antibody variable domains requires co-selection of compensatory mutations to maintain thermodynamic stability. Sci Rep 7:45259 (2017).
Kakkad et al. Collagen 1 fiber content may predict for recurrence in non-small cell lung cancer. Cancer Research 78(13 Supplement):3691-3691 (2018).
Kauder et al., ALX148 blocks CD47 and enhances innate and adaptive antitumor immunity with a favorable safety profile. PLoS One 13(8):e0201832 (2019).
Kim et al., 2077—An oral dual inhibitor of IDO and TDO enhances anti-cancer immunity and synergizes with immune checkpoint blockade. Annals Oncol 29 (suppl_8):viii400-viii441 (2018) (Poster Abstract).
Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf.
Lu et al., Characterization of potent and selective iodonium-class inhibitors of NADPH oxidases. Biochem Pharmacol 143:25-38 (2017).
Lv et al. Mesothelin as a biomarker for targeted therapy. Biomark Res 7:18 (2019).
Ma et al. Combination therapy with T cell engager and PD-L1 blockade enhances the antitumor potency of T cells as predicted by a QSP model. J Immunother Cancer. 8(2):e001141 (2020).
Magiera-Mularz et al. Bioactive macrocyclic inhibitors of the PD-1/PD-L1 immune checkpoint Angew. Chem. Int. Ed. 56(44):13732-13735 (2017).
Monney et al. Th1-specific cell surface protein Tim-3 regulates macrophage activation and severity of an autoimmune disease. Nature 415:536-41 (2002).
Nakae et al. Phenotypic differences between Th1 and Th17 cells and negative regulation of Th1 cell differentiation by IL-17. J Leukoc Biol 81:1258-68 (2007).
Nicolaou et al. Calicheamicin ϴ'1 : a rationally designed molecule with extremely potent and selective DNA cleaving properties and apoptosis inducing activity. Angew. Chem. Intl. Ed. Engl., 33:183-186 (1994).
PCT/US2022/019302 International Search Report and Written Opinion dated Jun. 27, 2022.

(56) References Cited

OTHER PUBLICATIONS

PCT/US2022/022871 International Search Report and Written Opinion dated Aug. 3, 2022.
PCT/US2022/031916 International Search Report and Written Opinion dated Sep. 29, 2022.
Perrot et al., Blocking Antibodies Targeting the CD39/CD73 Immunosuppressive Pathway Unleash Immune Responses in Combination Cancer Therapies. Cell Reports 8:2411-2425.E9 (2019).
Poczatek et al. Ep-Cam levels in prostatic adenocarcinoma and prostatic intraepithelial neoplasia. J Urol. 162:1462-1464 (1999).
Popoli et al., Effects of SCH 58261, an Adenosine A2A receptor antagonist, on quinpirole-induced turning in 6-Hydroxydopamine-lesioned rats: lack of tolerance after chronic caffeine intake. Neuropsychopharm 22:522-529 (2000).
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
Schaer et al. Modulation of GITR for cancer immunotherapy. Curr Opin Immunol. 24(2): 217-224 (2012).
Sheng et al. Novel Transgenic Mouse Model for Studying Human Serum Albumin as a Biomarker of Carcinogenic Exposure. Chem. Res. Toxicol. 29(5):797-809 (2016).
Sheridan. IDO inhibitors move center stage in immuno-oncology. Nat Biotechnol 33:321-322 (2015).
Stasi et al., Animal models of Parkinson's disease: Effects of two adenosine A2A receptor antagonists ST4206 and ST3932, metabolites of 2-n-Butyl-9-methyl-8-[1,2,3]triazol-2-yl-9H-purin-6-ylamine (ST1535). Europ J Pharmacol 761:353-361 (2015).
Stehle et al. Albumin-based drug carriers: comparison between serum albumins of different species on pharmacokinetics and tumor uptake of the conjugate. Anticancer Drugs. 10(8):785-90 (1999).
Tang et al., NOX4, a new genetic target for anti-cancer therapy in digestive system cancer. J Dig Dis 19(10):578-585 (2018).
U.S. Appl. No. 16/159,554 Office Action dated Mar. 16, 2021.
U.S. Appl. No. 16/339,263 Office Action dated May 3, 2022.
U.S. Appl. No. 16/773,843 Office Action dated Aug. 11, 2022.
U.S. Appl. No. 16/802,007 Office Action dated Sep. 29, 2022.
Wang et al., A Small Molecule Antagonist of PD-1/PD-L1 Interactions Acts as an Immune Checkpoint Inhibitor for NSCLC and Melanoma Immunotherapy. Front. Immunol. 12:654463.
Wang et al., In vitro characterization of the anti-PD-1 antibody nivolumab, BMS-936558, and in vivo toxicology in non-human primates. Cancer Immunol. Res. 2(9):846-856 (2014).
Watt et al., Homophilic adhesion of human CEACAM1 involves N-terminal domain interactions: structural analysis of the binding site. Blood 98:1469-1479 (2001).
Weir et al., Colony stimulating factor-1 plays a role in osteoclast formation and function in bone resorption induced by parathyroid hormone and parathyroid hormone-related protein. J Bone Mineral Res 11:1474-1481 (1996).
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Almagro et al. Humanization of antibodies. Front Biosci 13:1619-1633 (2008).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1997).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Baum et al. Antitumor activities of PSMAxCD3 diabodies by redirected T-cell lysis of prostate cancer cells. Immunotherapy 5(1):27-38 (2013).
Bedouelle et al. Diversity and junction residues as hotspots of binding energy in an antibody neutralizing the dengue virus. FEBS J 273(1):34-46 (2006).
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Design and synthesis of germline-based hemi-humanized single-chain Fv against the CD18 surface antigen. Protein Eng 13(5):353-360 (2000).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Casset et al. A peptide mimetic of an anti-CD4 monoclonal antibody by rational design. Biochemical and Biophysical Research Communication 307:198-205 (2003).
Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).

(56) References Cited

OTHER PUBLICATIONS

Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of mmunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prev 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients wih mesothelioma and lung cancer. Clin. Cancer Res. 13:5076-5081 (2007).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD38 variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholine to an anti-DNA autoantibody is due to a single base change in its heavy chain variable region. PNAS USA 84(9):2926-30 (1987).

Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prev 15:1751 (2006).
Holliger, et al. "Diabodies": small bivalent and bispecific antibody fragments. Proc Natl Acad Sci USA. Jul. 15, 1993; 90(14): 6444-6448. doi: 10.1073/pnas.90.14.6444.
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half- life of a single-chain diabody-ABD fusion protein. Protein Eng. Des. Sel. 23(11):827-34 (2010).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).

(56) References Cited

OTHER PUBLICATIONS

Jones et al. Replacing the complementarity-determining regions in a human antibody with those from a mouse. Nature 321:522-525 (1986).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by Rtx. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017/056530 International Search Report and Written Opinion dated Jan. 23, 2018.
PCT/US2017/063121 International Search Report and Written Opinion dated Mar. 26, 2018.
PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.

(56) References Cited

OTHER PUBLICATIONS

PCT/US2018/055682 International Search Report and Written Opinion dated Mar. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052270 International Search Report and Written Opinion dated Mar. 5, 2020.
PCT/US2019/053017 International Search Report and Written Opinion dated Jan. 31, 2020.
PCT/US/2020/032985 International Search Report and Written Opinion dated Oct. 15, 2020.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen-binding loops of camel single-domain antibodies. J. Mol. Biol. 352(3):597-607 (2005).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement- dependent cytotoxicity against acute myeloid leukemia progenitor cells. Blood 117(16):4262-4272 (2011).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).

(56) References Cited

OTHER PUBLICATIONS

Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.
U.S. Appl. No. 15/704,620 Office Action dated Oct. 26, 2017.
U.S. Appl. No. 15/821,498 Office Action dated Apr. 21, 2020.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).

Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10): e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin For Monitoring and Treating Mesothelioma. Sci Rep 5:9928 (2015).
Zhu et al. COMBODY: one-domain antibody multimer with improved avidity. Immunology and Cell Biology 88(6):667-675 (2010).
Chen et al. Enhancement and destruction of antibody function U by somatic mutation: unequal occurrence is controlled by V gene combinatorial associations. The EMBO Journal 14(12):2784-2794 (1995).
Colman. Effects of amino acid sequence changes on antibody-antigen interactions. Res Immunol 145(1):33-36 (1994).
Galsky et al. Phase I trial of the prostate-specific membrane antigen-directed immunoconjugate MLN2704 in patients with progressive metastatic castration-resistant prostate cancer. J Clin Oncol 26(13):2147-54 (2008).
Henry et al. A prostate-specific membrane antigen-targeted monoclonal antibody-chemotherapeutic conjugate designed for the treatment of prostate cancer. Cancer Res. 64(21):7995-8001 (2004).
Hupe et al. Expression of Prostate-Specific Membrane Antigen (PSMA) on Biopsies Is an Independent Risk Stratifier of Prostate Cancer Patients at Time of Initial Diagnosis. Front Oncol 8:623 (2018).
Jemaa et al. Co-expression and impact of prostate specific membrane antigen and prostate specific antigen in prostatic pathologies. J Exp Clin Cancer Res 29(1):171 (2010).
Jiang et al. Protritac: A protease cleavable T cell Engager Platform. Scientific Reports 6(Suppl 1):115 Available at https://calidibio.com/wp-content/uploads/2019/10/609-Abstract-_SITC-2018.pdf (2018).
Kelm et al., Functional groups of sialic acids involved in binding to siglecs (sialoadhesins) deduced from interactions with synthetic analogues. Eur. J. Biochem. 255:663-672 (1998).
Kelm et al., The Sialoadhesins—a family of sialic acid-dependent cellular recognition molecules within the immunoglobulin superfamily. Glycoconj. J. 13:913-926 (1996).
Korenchuk et al. VCaP, a cell-based model system of human prostate cancer. In Vivo. 15(2):163-8 (2001).
Loberg et al. Development of the VCaP androgen-independent model of prostate cancer. Urol Oncol 24(2):161-8 (2006).
McDevitt et al. An alpha-particle emitting antibody ([213Bi]J591) for radioimmunotherapy of prostate cancer. Cancer Res. 60:6095-6100 (2000).
PCT/US2022/031917 International Search Report and Written Opinion dated Dec. 2, 2022.
PCT/US2022/031919 International Search Report and Written Opinion dated Nov. 21, 2022.

(56) References Cited

OTHER PUBLICATIONS

PCT/US2022/034856 International Search Report and Written Opinion dated Dec. 8, 2022.
Rabia, et al. Understanding and overcoming trade-offs between antibody affinity, specificity, stability and solubility. Biochem Eng J. 137:365-374. (2018).
Sramkoski et al. A new human prostate carcinoma cell line, 22Rv1. In Vitro Cell Dev Biol Anim 35(7):403-409 (1999).
Stanciu-Herrera et al., Anti-CD19 and anti-CD22 monoclonal antibodies increase the effectiveness of chemotherapy in Pre-B acute lymphoblastic leukemia cell lines . Leuk Res. 32:625-32 (2008).
Tamura et al. Structural correlates of an anticarcinoma antibody: identification of specificity—determining residues (SDRs) and development of a minimally immunogenic antibody variant by retention of SDRs only. J Immunol. 164(3):1432-41 (2020).
U.S. Appl. No. 16/339,263 Office Action dated Jan. 18, 2023.
U.S. Appl. No. 16/802,007 Office Action dated Apr. 14, 2023.
U.S. Appl. No. 16/999,773 Office Action dated Apr. 21, 2023.
U.S. Appl. No. 17/030,118 Office Action dated May 5, 2023.
Ye et al. Androgen and epidermal growth factor down-regulate cyclin-dependent kinase inhibitor p27Kip1 and costimulate proliferation of MDA PCa 2a and MDA PCa 2b prostate cancer cells. Clin Cancer Res 5(8):2171-7 (1999).
Chen et al. Preparation and characterization of dexamethasone acetate-loaded solid lipid nanoparticles. Chinese J Pharm 39(4):261-264 (2008) (English abstract).
Dondelinger et al., Understanding the Significance and Implications of Antibody Numbering and Antigen-Binding Surface/Residue Definition. Frontiers in Immunology 9(2278):1-15 (2018).
Eshhar, et al., Specific activation and targeting of cytotoxic lymphocytes through chimeric single chains consisting of antibody-binding domains and the y or s subunits of the immunoglobulin and T-cell receptors. PNAS USA 90:720-724 (1993).
GenBank AHA34196.1, immunoglobulin variable heavy regionJIY-F10 RTA-F10, partial [Vicugna pacos] (Nov. 18, 2013).
Hu et al. Over-expression of human Notch ligand Delta-like 3 promotes proliferation of human gastric cancer cells in vitro. Nan Fang Yi Ke Da Xue Xue Bao 38(1):14-19 (2018) (English Abstract).
Le Gall et al., Immunosuppressive Properties of Anti-CD3 Single-Chain Fv and Diabody. Journal of Immunological Methods 285(1):111-127 (2004).
MacCallum, Robert M, et al., Antibody-Antigen Interactions: Contact Analysis and Binding Site Topography. Journal of Molecular Biology 262(5):732-745 (1996).
Ryan et al. Antibody targeting of B-cell maturation antigen on malignant plasma cells. Mol Cancer Ther 6(11):3009-3018 (2007).
U.S. Appl. No. 17/150,272 Office Action dated Sep. 15, 2023.
U.S. Appl. No. 17/276,796 Office Action dated Feb. 1, 2024.
Zhao et al. Novel Antibody Therapeutics Targeting Mesothelin In Solid Tumors. Clin Cancer Drugs 3(2):76-86 (2016).

* cited by examiner

SEQUENCE LISTING

<160> NUMBER OF SEQ ID NOS: 60

<210> SEQ ID NO 1
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Gly Ser Leu Lys Leu Ser Cys Ala Ala
145                 150                 155                 160

Ser Gly Phe Thr Phe Asn Lys Tyr Ala Met Asn Trp Val Arg Gln Ala
                165                 170                 175

Pro Gly Lys Gly Leu Glu Trp Val Ala Arg Ile Arg Ser Lys Tyr Asn
            180                 185                 190

Asn Tyr Ala Thr Tyr Tyr Ala Asp Ser Val Lys Asp Arg Phe Thr Ile
        195                 200                 205

Ser Arg Asp Asp Ser Lys Asn Thr Ala Tyr Leu Gln Met Asn Asn Leu
    210                 215                 220

Lys Thr Glu Asp Thr Ala Val Tyr Tyr Cys Val Arg His Gly Asn Phe
225                 230                 235                 240

Gly Asn Ser Tyr Ile Ser Tyr Trp Ala Tyr Trp Gly Gln Gly Thr Leu
                245                 250                 255

Val Thr Val Ser Ser Gly Gly Gly Gly Ser Gly Gly Gly Gly Ser Gly
            260                 265                 270

Gly Gly Gly Ser Gln Thr Val Val Thr Gln Glu Pro Ser Leu Thr Val
        275                 280                 285

Ser Pro Gly Gly Thr Val Thr Leu Thr Cys Gly Ser Ser Thr Gly Ala
    290                 295                 300

Val Thr Ser Gly Asn Tyr Pro Asn Trp Val Gln Gln Lys Pro Gly Gln
305                 310                 315                 320

Ala Pro Arg Gly Leu Ile Gly Gly Thr Lys Phe Leu Ala Pro Gly Thr
                325                 330                 335

Pro Ala Arg Phe Ser Gly Ser Leu Leu Gly Gly Lys Ala Ala Leu Thr
            340                 345                 350

Leu Ser Gly Val Gln Pro Glu Asp Glu Ala Glu Tyr Tyr Cys Val Leu
        355                 360                 365

Trp Tyr Ser Asn Arg Trp Val Phe Gly Gly Gly Thr Lys Leu Thr Val
    370                 375                 380

Leu Gly Gly Gly Gly Ser Gly Gly Gly Ser Glu Val Gln Leu Val Glu
385                 390                 395                 400

Ser Gly Gly Gly Leu Val Gln Pro Gly Asn Ser Leu Arg Leu Ser Cys
```

```
            405                 410                 415
Ala Ala Ser Gly Phe Thr Phe Ser Ser Phe Gly Met Ser Trp Val Arg
            420                 425                 430

Gln Ala Pro Gly Lys Gly Leu Glu Trp Val Ser Ser Ile Ser Gly Ser
            435                 440                 445

Gly Ser Asp Thr Leu Tyr Ala Asp Ser Val Lys Gly Arg Phe Thr Ile
            450                 455                 460

Ser Arg Asp Asn Ala Lys Thr Thr Leu Tyr Leu Gln Met Asn Ser Leu
465                 470                 475                 480

Arg Pro Glu Asp Thr Ala Val Tyr Tyr Cys Thr Ile Gly Gly Ser Leu
                485                 490                 495

Ser Arg Ser Ser Gln Gly Thr Leu Val Thr Val Ser Ser His His His
            500                 505                 510

His His His
        515

<210> SEQ ID NO 2
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Arg
225                 230                 235                 240
```

```
Ser Ser Gln Gly Thr Leu Val Thr Val Ser Ser Gly Gly Gly Ser
            245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
            275                 280                 285

Phe Asn Lys Tyr Ala Met Asn Trp Val Arg Gln Ala Pro Gly Lys Gly
290                 295                 300

Leu Glu Trp Val Ala Arg Ile Arg Ser Lys Tyr Asn Asn Tyr Ala Thr
305                 310                 315                 320

Tyr Tyr Ala Asp Ser Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Gly Asn Phe Gly Asn Ser Tyr
            355                 360                 365

Ile Ser Tyr Trp Ala Tyr Trp Gly Gln Gly Thr Leu Val Thr Val Ser
            370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
            405                 410                 415

Thr Val Thr Leu Thr Cys Gly Ser Ser Thr Gly Ala Val Thr Ser Gly
            420                 425                 430

Asn Tyr Pro Asn Trp Val Gln Gln Lys Pro Gly Gln Ala Pro Arg Gly
            435                 440                 445

Leu Ile Gly Gly Thr Lys Phe Leu Ala Pro Gly Thr Pro Ala Arg Phe
450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Val Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 3
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80
```

-continued

```
Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Ser Glu Val Gln Leu Val Glu Ser Gly Gly Leu Val Gln Ala
            260                 265                 270

Gly Gly Ser Leu Arg Leu Ser Cys Ala Ala Ser Gly Arg Thr Phe Ser
        275                 280                 285

Ser Tyr Ala Met Gly Trp Phe Arg Gln Ala Pro Gly Lys Glu Arg Glu
    290                 295                 300

Phe Val Val Ala Ile Asn Trp Ser Ser Gly Ser Thr Tyr Tyr Ala Asp
305                 310                 315                 320

Ser Val Lys Gly Arg Phe Thr Ile Ser Arg Asp Asn Ala Lys Asn Thr
                325                 330                 335

Met Tyr Leu Gln Met Asn Ser Leu Lys Pro Glu Asp Thr Ala Val Tyr
            340                 345                 350

Tyr Cys Ala Ala Gly Tyr Gln Ile Asn Ser Gly Asn Tyr Asn Phe Lys
        355                 360                 365

Asp Tyr Glu Tyr Asp Tyr Trp Gly Gln Gly Thr Gln Val Thr Val Ser
    370                 375                 380

Ser Gly Gly Gly Gly Ser Gly Gly Gly Ser Glu Val Gln Leu Val Glu
385                 390                 395                 400

Ser Gly Gly Gly Leu Val Gln Pro Gly Asn Ser Leu Arg Leu Ser Cys
                405                 410                 415

Ala Ala Ser Gly Phe Thr Phe Ser Ser Phe Gly Met Ser Trp Val Arg
            420                 425                 430

Gln Ala Pro Gly Lys Gly Leu Glu Trp Val Ser Ser Ile Ser Gly Ser
        435                 440                 445

Gly Ser Asp Thr Leu Tyr Ala Asp Ser Val Lys Gly Arg Phe Thr Ile
    450                 455                 460

Ser Arg Asp Asn Ala Lys Thr Thr Leu Tyr Leu Gln Met Asn Ser Leu
465                 470                 475                 480

Arg Pro Glu Asp Thr Ala Val Tyr Tyr Cys Thr Ile Gly Gly Ser Leu
                485                 490                 495
```

-continued

Ser Arg Ser Ser Gln Gly Thr Leu Thr Val Ser Ser His His His
            500                 505                 510

His His His
      515

<210> SEQ ID NO 4
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Ser Glu Val Gln Leu Val Glu Ser Gly Gly Gly Leu Val Gln Pro
            260                 265                 270

Gly Asn Ser Leu Arg Leu Ser Cys Ala Ala Ser Gly Phe Thr Phe Ser
        275                 280                 285

Ser Phe Gly Met Ser Trp Val Arg Gln Ala Pro Gly Lys Gly Leu Glu
    290                 295                 300

Trp Val Ser Ser Ile Ser Gly Ser Gly Ser Asp Thr Leu Tyr Ala Asp
305                 310                 315                 320

Ser Val Lys Gly Arg Phe Thr Ile Ser Arg Asp Asn Ala Lys Thr Thr
                325                 330                 335

-continued

```
Leu Tyr Leu Gln Met Asn Ser Leu Arg Pro Glu Asp Thr Ala Val Tyr
            340                 345                 350
Tyr Cys Thr Ile Gly Gly Ser Leu Ser Arg Ser Ser Gln Gly Thr Leu
        355                 360                 365
Val Thr Val Ser Ser Gly Gly Gly Gly Ser Gly Gly Gly Ser Glu Val
    370                 375                 380
Gln Leu Val Glu Ser Gly Gly Gly Leu Val Gln Ala Gly Gly Ser Leu
385                 390                 395                 400
Arg Leu Ser Cys Ala Ala Ser Gly Arg Thr Phe Ser Ser Tyr Ala Met
                405                 410                 415
Gly Trp Phe Arg Gln Ala Pro Gly Lys Glu Arg Glu Phe Val Val Ala
            420                 425                 430
Ile Asn Trp Ser Ser Gly Ser Thr Tyr Tyr Ala Asp Ser Val Lys Gly
        435                 440                 445
Arg Phe Thr Ile Ser Arg Asp Asn Ala Lys Asn Thr Met Tyr Leu Gln
    450                 455                 460
Met Asn Ser Leu Lys Pro Glu Asp Thr Ala Val Tyr Tyr Cys Ala Ala
465                 470                 475                 480
Gly Tyr Gln Ile Asn Ser Gly Asn Tyr Asn Phe Lys Asp Tyr Glu Tyr
                485                 490                 495
Asp Tyr Trp Gly Gln Gly Thr Gln Val Thr Val Ser Ser His His His
            500                 505                 510
His His His
        515

<210> SEQ ID NO 5
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Glu Val Gln Leu
        115                 120                 125
Val Glu Ser Gly Gly Gly Leu Val Gln Ala Gly Gly Ser Leu Arg Leu
    130                 135                 140
Ser Cys Ala Ala Ser Gly Arg Thr Phe Ser Ser Tyr Ala Met Gly Trp
145                 150                 155                 160
Phe Arg Gln Ala Pro Gly Lys Glu Arg Glu Phe Val Val Ala Ile Asn
```

```
                   165                 170                 175
Trp Ser Ser Gly Ser Thr Tyr Tyr Ala Asp Ser Val Lys Gly Arg Phe
                180                 185                 190
Thr Ile Ser Arg Asp Asn Ala Lys Asn Thr Met Tyr Leu Gln Met Asn
            195                 200                 205
Ser Leu Lys Pro Glu Asp Thr Ala Val Tyr Tyr Cys Ala Ala Gly Tyr
        210                 215                 220
Gln Ile Asn Ser Gly Asn Tyr Asn Phe Lys Asp Tyr Glu Tyr Asp Tyr
225                 230                 235                 240
Trp Gly Gln Gly Thr Gln Val Thr Val Ser Ser Gly Gly Gly Gly Ser
                245                 250                 255
Gly Gly Gly Ser Glu Val Gln Leu Val Glu Ser Gly Gly Gly Leu Val
                260                 265                 270
Gln Pro Gly Gly Ser Leu Lys Leu Ser Cys Ala Ala Ser Gly Phe Thr
            275                 280                 285
Phe Asn Lys Tyr Ala Met Asn Trp Val Arg Gln Ala Pro Gly Lys Gly
        290                 295                 300
Leu Glu Trp Val Ala Arg Ile Arg Ser Lys Tyr Asn Asn Tyr Ala Thr
305                 310                 315                 320
Tyr Tyr Ala Asp Ser Val Lys Asp Arg Phe Thr Ile Ser Arg Asp Asp
                325                 330                 335
Ser Lys Asn Thr Ala Tyr Leu Gln Met Asn Asn Leu Lys Thr Glu Asp
            340                 345                 350
Thr Ala Val Tyr Tyr Cys Val Arg His Gly Asn Phe Gly Asn Ser Tyr
        355                 360                 365
Ile Ser Tyr Trp Ala Tyr Trp Gly Gln Gly Thr Leu Val Thr Val Ser
    370                 375                 380
Ser Gly Gly Gly Gly Ser Gly Gly Gly Ser Gly Gly Gly Gly Ser
385                 390                 395                 400
Gln Thr Val Val Thr Gln Glu Pro Ser Leu Thr Val Ser Pro Gly Gly
                405                 410                 415
Thr Val Thr Leu Thr Cys Gly Ser Ser Thr Gly Ala Val Thr Ser Gly
                420                 425                 430
Asn Tyr Pro Asn Trp Val Gln Gln Lys Pro Gly Gln Ala Pro Arg Gly
            435                 440                 445
Leu Ile Gly Gly Thr Lys Phe Leu Ala Pro Gly Thr Pro Ala Arg Phe
        450                 455                 460
Ser Gly Ser Leu Leu Gly Gly Lys Ala Ala Leu Thr Leu Ser Gly Val
465                 470                 475                 480
Gln Pro Glu Asp Glu Ala Glu Tyr Tyr Cys Val Leu Trp Tyr Ser Asn
                485                 490                 495
Arg Trp Val Phe Gly Gly Gly Thr Lys Leu Thr Val Leu His His
                500                 505                 510
His His His
        515

<210> SEQ ID NO 6
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

-continued

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Glu Val Gln Leu
        115                 120                 125
Val Glu Ser Gly Gly Gly Leu Val Gln Pro Gly Gly Ser Leu Lys Leu
    130                 135                 140
Ser Cys Ala Ala Ser Gly Phe Thr Phe Asn Lys Tyr Ala Met Asn Trp
145                 150                 155                 160
Val Arg Gln Ala Pro Gly Lys Gly Leu Glu Trp Val Ala Arg Ile Arg
                165                 170                 175
Ser Lys Tyr Asn Asn Tyr Ala Thr Tyr Tyr Ala Asp Ser Val Lys Asp
            180                 185                 190
Arg Phe Thr Ile Ser Arg Asp Asp Ser Lys Asn Thr Ala Tyr Leu Gln
        195                 200                 205
Met Asn Asn Leu Lys Thr Glu Asp Thr Ala Val Tyr Tyr Cys Val Arg
    210                 215                 220
His Gly Asn Phe Gly Asn Ser Tyr Ile Ser Tyr Trp Ala Tyr Trp Gly
225                 230                 235                 240
Gln Gly Thr Leu Val Thr Val Ser Ser Gly Gly Gly Ser Gly Gly
                245                 250                 255
Gly Gly Ser Gly Gly Gly Gly Ser Gln Thr Val Val Thr Gln Glu Pro
            260                 265                 270
Ser Leu Thr Val Ser Pro Gly Gly Thr Val Thr Leu Thr Cys Gly Ser
        275                 280                 285
Ser Thr Gly Ala Val Thr Ser Gly Asn Tyr Pro Asn Trp Val Gln Gln
    290                 295                 300
Lys Pro Gly Gln Ala Pro Arg Gly Leu Ile Gly Gly Thr Lys Phe Leu
305                 310                 315                 320
Ala Pro Gly Thr Pro Ala Arg Phe Ser Gly Ser Leu Leu Gly Gly Lys
                325                 330                 335
Ala Ala Leu Thr Leu Ser Gly Val Gln Pro Glu Asp Glu Ala Glu Tyr
            340                 345                 350
Tyr Cys Val Leu Trp Tyr Ser Asn Arg Trp Val Phe Gly Gly Gly Thr
        355                 360                 365
Lys Leu Thr Val Leu Gly Gly Gly Ser Gly Gly Ser Glu Val
    370                 375                 380
Gln Leu Val Glu Ser Gly Gly Leu Val Gln Ala Gly Gly Ser Leu
385                 390                 395                 400
Arg Leu Ser Cys Ala Ala Ser Gly Arg Thr Phe Ser Ser Tyr Ala Met
                405                 410                 415
Gly Trp Phe Arg Gln Ala Pro Gly Lys Glu Arg Glu Phe Val Val Ala
```

```
                       420                 425                 430
Ile Asn Trp Ser Ser Gly Ser Thr Tyr Tyr Ala Asp Ser Val Lys Gly
            435                 440                 445

Arg Phe Thr Ile Ser Arg Asp Asn Ala Lys Asn Thr Met Tyr Leu Gln
            450                 455                 460

Met Asn Ser Leu Lys Pro Glu Asp Thr Ala Val Tyr Tyr Cys Ala Ala
465                 470                 475                 480

Gly Tyr Gln Ile Asn Ser Gly Asn Tyr Asn Phe Lys Asp Tyr Glu Tyr
            485                 490                 495

Asp Tyr Trp Gly Gln Gly Thr Gln Val Thr Val Ser Ser His His His
            500                 505                 510

His His His
    515

<210> SEQ ID NO 7
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
            85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Lys Gln
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Asn Tyr Gly Val His Trp Val Arg
145                 150                 155                 160

Gln Ser Pro Gly Lys Gly Leu Glu Trp Leu Gly Val Ile Trp Ser Gly
            165                 170                 175

Gly Asn Thr Asp Tyr Asn Thr Pro Phe Thr Ser Arg Leu Ser Ile Asn
            180                 185                 190

Lys Asp Asn Ser Lys Ser Gln Val Phe Phe Lys Met Asn Ser Leu Gln
        195                 200                 205

Ser Asn Asp Thr Ala Ile Tyr Tyr Cys Ala Arg Ala Leu Thr Tyr Tyr
    210                 215                 220

Asp Tyr Glu Phe Ala Tyr Trp Gly Gln Gly Thr Leu Val Thr Val Ser
225                 230                 235                 240

Ala Ser Gly Gly Gly Gly Ser Glu Val Gln Leu Val Glu Ser Gly Gly
            245                 250                 255
```

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

His His His His His His
            500

<210> SEQ ID NO 8
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Gly Ser
            100                 105                 110

```
Gly Gly Gly Gly Ser Gly Gly Gly Ser Gln Val Gln Leu Lys Gln
            115                 120                 125
Ser Gly Pro Gly Leu Val Gln Pro Ser Gln Ser Leu Ser Ile Thr Cys
    130                 135                 140
Thr Val Ser Gly Phe Ser Leu Thr Asn Tyr Gly Val His Trp Val Arg
145                 150                 155                 160
Gln Ser Pro Gly Lys Gly Leu Glu Trp Leu Gly Val Ile Trp Ser Gly
                165                 170                 175
Gly Asn Thr Asp Tyr Asn Thr Pro Phe Thr Ser Arg Leu Ser Ile Asn
            180                 185                 190
Lys Asp Asn Ser Lys Ser Gln Val Phe Phe Lys Met Asn Ser Leu Gln
        195                 200                 205
Ser Asn Asp Thr Ala Ile Tyr Tyr Cys Ala Arg Ala Leu Thr Tyr Tyr
    210                 215                 220
Asp Tyr Glu Phe Ala Tyr Trp Gly Gln Gly Thr Leu Val Thr Val Ser
225                 230                 235                 240
Ala Ser Gly Gly Gly Gly Ser Glu Val Gln Leu Val Glu Ser Gly Gly
                245                 250                 255
Gly Leu Val Gln Pro Gly Gly Ser Leu Lys Leu Ser Cys Ala Ala Ser
            260                 265                 270
Gly Phe Thr Phe Asn Lys Tyr Ala Met Asn Trp Val Arg Gln Ala Pro
        275                 280                 285
Gly Lys Gly Leu Glu Trp Val Ala Arg Ile Arg Ser Lys Tyr Asn Asn
    290                 295                 300
Tyr Ala Thr Tyr Tyr Ala Asp Ser Val Lys Asp Arg Phe Thr Ile Ser
305                 310                 315                 320
Arg Asp Asp Ser Lys Asn Thr Ala Tyr Leu Gln Met Asn Asn Leu Lys
                325                 330                 335
Thr Glu Asp Thr Ala Val Tyr Tyr Cys Val Arg His Gly Asn Phe Gly
            340                 345                 350
Asn Ser Tyr Ile Ser Tyr Trp Ala Tyr Trp Gly Gln Gly Thr Leu Val
        355                 360                 365
Thr Val Ser Ser Gly Gly Gly Ser Gly Gly Gly Ser Gly Gly
    370                 375                 380
Gly Gly Ser Gln Thr Val Val Thr Gln Glu Pro Ser Leu Thr Val Ser
385                 390                 395                 400
Pro Gly Gly Thr Val Thr Leu Thr Cys Gly Ser Ser Thr Gly Ala Val
                405                 410                 415
Thr Ser Gly Asn Tyr Pro Asn Trp Val Gln Gln Lys Pro Gly Gln Ala
            420                 425                 430
Pro Arg Gly Leu Ile Gly Gly Thr Lys Phe Leu Ala Pro Gly Thr Pro
        435                 440                 445
Ala Arg Phe Ser Gly Ser Leu Leu Gly Gly Lys Ala Ala Leu Thr Leu
    450                 455                 460
Ser Gly Val Gln Pro Glu Asp Glu Ala Glu Tyr Tyr Cys Val Leu Trp
465                 470                 475                 480
Tyr Ser Asn Arg Trp Val Phe Gly Gly Gly Thr Lys Leu Thr Val Leu
                485                 490                 495
Gly Gly Gly Gly Ser Gly Gly Gly Ser Glu Val Gln Leu Val Glu Ser
            500                 505                 510
Gly Gly Gly Leu Val Gln Pro Gly Asn Ser Leu Arg Leu Ser Cys Ala
        515                 520                 525
```

```
Ala Ser Gly Phe Thr Phe Ser Ser Phe Gly Met Ser Trp Val Arg Gln
        530                 535                 540

Ala Pro Gly Lys Gly Leu Glu Trp Val Ser Ser Ile Ser Gly Ser Gly
545                 550                 555                 560

Ser Asp Thr Leu Tyr Ala Asp Ser Val Lys Gly Arg Phe Thr Ile Ser
            565                 570                 575

Arg Asp Asn Ala Lys Thr Thr Leu Tyr Leu Gln Met Asn Ser Leu Arg
        580                 585                 590

Pro Glu Asp Thr Ala Val Tyr Tyr Cys Thr Ile Gly Gly Ser Leu Ser
        595                 600                 605

Arg Ser Ser Gln Gly Thr Leu Val Thr Val Ser Ser His His His His
    610                 615                 620

His His
625

<210> SEQ ID NO 9
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Gly Ser Leu Lys Leu Ser Cys Ala Ala
    130                 135                 140

Ser Gly Phe Thr Phe Asn Lys Tyr Ala Met Asn Trp Val Arg Gln Ala
145                 150                 155                 160

Pro Gly Lys Gly Leu Glu Trp Val Ala Arg Ile Arg Ser Lys Tyr Asn
                165                 170                 175

Asn Tyr Ala Thr Tyr Tyr Ala Asp Ser Val Lys Asp Arg Phe Thr Ile
            180                 185                 190

Ser Arg Asp Asp Ser Lys Asn Thr Ala Tyr Leu Gln Met Asn Asn Leu
        195                 200                 205

Lys Thr Glu Asp Thr Ala Val Tyr Tyr Cys Val Arg His Gly Asn Phe
    210                 215                 220

Gly Asn Ser Tyr Ile Ser Tyr Trp Ala Tyr Trp Gly Gln Gly Thr Leu
225                 230                 235                 240

Val Thr Val Ser Ser Gly Gly Gly Gly Ser Gly Gly Gly Gly Ser Gly
                245                 250                 255
```

```
Gly Gly Gly Ser Gln Thr Val Thr Gln Glu Pro Ser Leu Thr Val
            260                 265                 270

Ser Pro Gly Gly Thr Val Thr Leu Thr Cys Gly Ser Ser Thr Gly Ala
        275                 280                 285

Val Thr Ser Gly Asn Tyr Pro Asn Trp Val Gln Gln Lys Pro Gly Gln
    290                 295                 300

Ala Pro Arg Gly Leu Ile Gly Gly Thr Lys Phe Leu Ala Pro Gly Thr
305                 310                 315                 320

Pro Ala Arg Phe Ser Gly Ser Leu Leu Gly Gly Lys Ala Ala Leu Thr
                325                 330                 335

Leu Ser Gly Val Gln Pro Glu Asp Glu Ala Glu Tyr Tyr Cys Val Leu
            340                 345                 350

Trp Tyr Ser Asn Arg Trp Val Phe Gly Gly Gly Thr Lys Leu Thr Val
                355                 360                 365

Leu Gly Gly Gly Gly Ser Gly Gly Gly Ser Glu Val Gln Leu Val Glu
        370                 375                 380

Ser Gly Gly Gly Leu Val Gln Pro Gly Asn Ser Leu Arg Leu Ser Cys
385                 390                 395                 400

Ala Ala Ser Gly Phe Thr Phe Ser Ser Phe Gly Met Ser Trp Val Arg
                405                 410                 415

Gln Ala Pro Gly Lys Gly Leu Glu Trp Val Ser Ser Ile Ser Gly Ser
            420                 425                 430

Gly Ser Asp Thr Leu Tyr Ala Asp Ser Val Lys Gly Arg Phe Thr Ile
        435                 440                 445

Ser Arg Asp Asn Ala Lys Thr Thr Leu Tyr Leu Gln Met Asn Ser Leu
450                 455                 460

Arg Pro Glu Asp Thr Ala Val Tyr Tyr Cys Thr Ile Gly Gly Ser Leu
465                 470                 475                 480

Ser Arg Ser Ser Gln Gly Thr Leu Val Thr Val Ser Ser His His His
                485                 490                 495

His His His

<210> SEQ ID NO 10
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110
```

Gly Gly Gly Ser Gly Gly Ser Glu Val Gln Leu Val Glu Ser Gly
            115                 120                 125
Gly Gly Leu Val Gln Pro Gly Asn Ser Leu Arg Leu Ser Cys Ala Ala
130                 135                 140
Ser Gly Phe Thr Phe Ser Ser Phe Gly Met Ser Trp Val Arg Gln Ala
145                 150                 155                 160
Pro Gly Lys Gly Leu Glu Trp Val Ser Ser Ile Ser Gly Ser Gly Ser
            165                 170                 175
Asp Thr Leu Tyr Ala Asp Ser Val Lys Gly Arg Phe Thr Ile Ser Arg
            180                 185                 190
Asp Asn Ala Lys Thr Thr Leu Tyr Leu Gln Met Asn Ser Leu Arg Pro
            195                 200                 205
Glu Asp Thr Ala Val Tyr Tyr Cys Thr Ile Gly Gly Ser Leu Ser Arg
            210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Gly Leu Val
            245                 250                 255
Gln Pro Gly Gly Ser Leu Lys Leu Ser Cys Ala Ala Ser Gly Phe Thr
            260                 265                 270
Phe Asn Lys Tyr Ala Met Asn Trp Val Arg Gln Ala Pro Gly Lys Gly
            275                 280                 285
Leu Glu Trp Val Ala Arg Ile Arg Ser Lys Tyr Asn Asn Tyr Ala Thr
            290                 295                 300
Tyr Tyr Ala Asp Ser Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
            325                 330                 335
Thr Ala Val Tyr Tyr Cys Val Arg His Gly Asn Phe Gly Asn Ser Tyr
            340                 345                 350
Ile Ser Tyr Trp Ala Tyr Trp Gly Gln Gly Thr Leu Val Thr Val Ser
            355                 360                 365
Ser Gly Gly Gly Gly Ser Gly Gly Gly Ser Gly Gly Gly Gly Ser
            370                 375                 380
Gln Thr Val Val Thr Gln Glu Pro Ser Leu Thr Val Ser Pro Gly Gly
385                 390                 395                 400
Thr Val Thr Leu Thr Cys Gly Ser Ser Thr Gly Ala Val Thr Ser Gly
            405                 410                 415
Asn Tyr Pro Asn Trp Val Gln Gln Lys Pro Gly Gln Ala Pro Arg Gly
            420                 425                 430
Leu Ile Gly Gly Thr Lys Phe Leu Ala Pro Gly Thr Pro Ala Arg Phe
            435                 440                 445
Ser Gly Ser Leu Leu Gly Gly Lys Ala Ala Leu Thr Leu Ser Gly Val
            450                 455                 460
Gln Pro Glu Asp Glu Ala Glu Tyr Tyr Cys Val Leu Trp Tyr Ser Asn
465                 470                 475                 480
Arg Trp Val Phe Gly Gly Gly Thr Lys Leu Thr Val Leu His His
            485                 490                 495
His His His

<210> SEQ ID NO 11
<211> LENGTH: 499
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 11

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Ser Glu Val Gln Leu Val Glu Ser Gly Gly Gly Leu Val Gln Pro
            260                 265                 270

Gly Asn Ser Leu Arg Leu Ser Cys Ala Ala Ser Gly Phe Thr Phe Ser
        275                 280                 285

Ser Phe Gly Met Ser Trp Val Arg Gln Ala Pro Gly Lys Gly Leu Glu
    290                 295                 300

Trp Val Ser Ser Ile Ser Gly Ser Gly Ser Asp Thr Leu Tyr Ala Asp
305                 310                 315                 320

Ser Val Lys Gly Arg Phe Thr Ile Ser Arg Asp Asn Ala Lys Thr Thr
                325                 330                 335

Leu Tyr Leu Gln Met Asn Ser Leu Arg Pro Glu Asp Thr Ala Val Tyr
            340                 345                 350

Tyr Cys Thr Ile Gly Gly Ser Leu Ser Arg Ser Ser Gln Gly Thr Leu
        355                 360                 365

Val Thr Val Ser Ser Gly Gly Gly Gly Ser Gly Gly Gly Ser Glu Val
    370                 375                 380
```

Gln Leu Val Glu Ser Gly Gly Gly Leu Val Gln Pro Gly Gly Ser Leu
385                 390                 395                 400

Thr Leu Ser Cys Ala Ala Ser Arg Phe Met Ile Ser Glu Tyr Ser Met
                405                 410                 415

His Trp Val Arg Gln Ala Pro Gly Lys Gly Leu Glu Trp Val Ser Thr
            420                 425                 430

Ile Asn Pro Ala Gly Thr Thr Asp Tyr Ala Glu Ser Val Lys Gly Arg
                435                 440                 445

Phe Thr Ile Ser Arg Asp Asn Ala Lys Asn Thr Leu Tyr Leu Gln Met
    450                 455                 460

Asn Ser Leu Lys Pro Glu Asp Thr Ala Val Tyr Tyr Cys Asp Gly Tyr
465                 470                 475                 480

Gly Tyr Arg Gly Gln Gly Thr Gln Val Thr Val Ser Ser His His His
                485                 490                 495

His His His

<210> SEQ ID NO 12
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Thr Leu
130                 135                 140

Ser Cys Ala Ala Ser Arg Phe Met Ile Ser Glu Tyr Ser Met His Trp
145                 150                 155                 160

Val Arg Gln Ala Pro Gly Lys Gly Leu Glu Trp Val Ser Thr Ile Asn
                165                 170                 175

Pro Ala Gly Thr Thr Asp Tyr Ala Glu Ser Val Lys Gly Arg Phe Thr
            180                 185                 190

Ile Ser Arg Asp Asn Ala Lys Asn Thr Leu Tyr Leu Gln Met Asn Ser
        195                 200                 205

Leu Lys Pro Glu Asp Thr Ala Val Tyr Tyr Cys Asp Gly Tyr Gly Tyr
210                 215                 220

Arg Gly Gln Gly Thr Gln Val Thr Val Ser Ser Gly Gly Gly Gly Ser
225                 230                 235                 240

Glu Val Gln Leu Val Glu Ser Gly Gly Gly Leu Val Gln Pro Gly Gly
                245                 250                 255

Ser Leu Lys Leu Ser Cys Ala Ala Ser Gly Phe Thr Phe Asn Lys Tyr
            260                 265                 270

Ala Met Asn Trp Val Arg Gln Ala Pro Gly Lys Gly Leu Glu Trp Val
        275                 280                 285

Ala Arg Ile Arg Ser Lys Tyr Asn Asn Tyr Ala Thr Tyr Tyr Ala Asp
    290                 295                 300

Ser Val Lys Asp Arg Phe Thr Ile Ser Arg Asp Asp Ser Lys Asn Thr
305                 310                 315                 320

Ala Tyr Leu Gln Met Asn Asn Leu Lys Thr Glu Asp Thr Ala Val Tyr
                325                 330                 335

Tyr Cys Val Arg His Gly Asn Phe Gly Asn Ser Tyr Ile Ser Tyr Trp
            340                 345                 350

Ala Tyr Trp Gly Gln Gly Thr Leu Val Thr Val Ser Ser Gly Gly Gly
        355                 360                 365

Gly Ser Gly Gly Gly Gly Ser Gly Gly Gly Gly Ser Gln Thr Val Val
    370                 375                 380

Thr Gln Glu Pro Ser Leu Thr Val Ser Pro Gly Gly Thr Val Thr Leu
385                 390                 395                 400

Thr Cys Gly Ser Ser Thr Gly Ala Val Thr Ser Gly Asn Tyr Pro Asn
                405                 410                 415

Trp Val Gln Gln Lys Pro Gly Gln Ala Pro Arg Gly Leu Ile Gly Gly
            420                 425                 430

Thr Lys Phe Leu Ala Pro Gly Thr Pro Ala Arg Phe Ser Gly Ser Leu
        435                 440                 445

Leu Gly Gly Lys Ala Ala Leu Thr Leu Ser Gly Val Gln Pro Glu Asp
    450                 455                 460

Glu Ala Glu Tyr Tyr Cys Val Leu Trp Tyr Ser Asn Arg Trp Val Phe
465                 470                 475                 480

Gly Gly Gly Thr Lys Leu Thr Val Leu His His His His His
                485                 490                 495

<210> SEQ ID NO 13
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Ser Gly Gly Ser Glu Val Gln Leu
        115                 120                 125

Val Glu Ser Gly Gly Gly Leu Val Gln Pro Gly Gly Ser Leu Lys Leu
130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser Gly Gly Gly Ser Gly Gly
                245                 250                 255

Gly Gly Ser Gly Gly Gly Ser Gln Thr Val Thr Gln Glu Pro
            260                 265                 270

Ser Leu Thr Val Ser Pro Gly Gly Thr Val Thr Leu Thr Cys Gly Ser
        275                 280                 285

Ser Thr Gly Ala Val Thr Ser Gly Asn Tyr Pro Asn Trp Val Gln Gln
    290                 295                 300

Lys Pro Gly Gln Ala Pro Arg Gly Leu Ile Gly Thr Lys Phe Leu
305                 310                 315                 320

Ala Pro Gly Thr Pro Ala Arg Phe Ser Gly Ser Leu Leu Gly Gly Lys
                325                 330                 335

Ala Ala Leu Thr Leu Ser Gly Val Gln Pro Glu Asp Glu Ala Glu Tyr
            340                 345                 350

Tyr Cys Val Leu Trp Tyr Ser Asn Arg Trp Val Phe Gly Gly Gly Thr
        355                 360                 365

Lys Leu Thr Val Leu Gly Gly Gly Gly Ser Gly Gly Gly Ser Glu Val
    370                 375                 380

Gln Leu Val Glu Ser Gly Gly Gly Leu Val Gln Pro Gly Gly Ser Leu
385                 390                 395                 400

Thr Leu Ser Cys Ala Ala Ser Arg Phe Met Ile Ser Glu Tyr Ser Met
                405                 410                 415

His Trp Val Arg Gln Ala Pro Gly Lys Gly Leu Glu Trp Val Ser Thr
            420                 425                 430

Ile Asn Pro Ala Gly Thr Thr Asp Tyr Ala Glu Ser Val Lys Gly Arg
        435                 440                 445

Phe Thr Ile Ser Arg Asp Asn Ala Lys Asn Thr Leu Tyr Leu Gln Met
    450                 455                 460

Asn Ser Leu Lys Pro Glu Asp Thr Ala Val Tyr Tyr Cys Asp Gly Tyr
465                 470                 475                 480

Gly Tyr Arg Gly Gln Gly Thr Gln Val Thr Val Ser Ser His His
                485                 490                 495

His His His

<210> SEQ ID NO 14
<211> LENGTH: 628
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Lys Pro
            165                 170                 175

Gly Gln Ala Pro Lys Ser Leu Ile Tyr Ser Ala Ser Tyr Arg Tyr Ser
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Ser Tyr Pro Tyr Thr Phe Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
    435                 440                 445

Thr Pro Ala Arg Phe Ser Gly Ser Leu Leu Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Ser Gly Gly Gly Ser Glu Val Gln Leu Val
            500                 505                 510

Glu Ser Gly Gly Gly Leu Val Gln Pro Gly Asn Ser Leu Arg Leu Ser
        515                 520                 525

Cys Ala Ala Ser Gly Phe Thr Phe Ser Ser Phe Gly Met Ser Trp Val
530                 535                 540

Arg Gln Ala Pro Gly Lys Gly Leu Glu Trp Val Ser Ser Ile Ser Gly
545                 550                 555                 560

Ser Gly Ser Asp Thr Leu Tyr Ala Asp Ser Val Lys Gly Arg Phe Thr
                565                 570                 575

Ile Ser Arg Asp Asn Ala Lys Thr Thr Leu Tyr Leu Gln Met Asn Ser
            580                 585                 590

Leu Arg Pro Glu Asp Thr Ala Val Tyr Tyr Cys Thr Ile Gly Gly Ser
        595                 600                 605

Leu Ser Arg Ser Ser Gln Gly Thr Leu Val Thr Val Ser Ser His His
    610                 615                 620

His His His His
625

<210> SEQ ID NO 15
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

```
Gln Gly Thr Leu Val Thr Val Ser Ser Gly Gly Gly Ser Gly Gly
            115                 120                 125
Gly Gly Ser Gly Gly Gly Ser Asp Ile Gln Met Thr Gln Ser Pro
130                 135                 140
Ser Ser Leu Ser Ala Ser Val Gly Asp Arg Val Thr Ile Thr Cys Lys
145                 150                 155                 160
Ala Ser Gln Asn Val Asp Thr Asn Val Ala Trp Tyr Gln Gln Lys Pro
                165                 170                 175
Gly Gln Ala Pro Lys Ser Leu Ile Tyr Ser Ala Ser Tyr Arg Tyr Ser
            180                 185                 190
Asp Val Pro Ser Arg Phe Ser Gly Ser Ala Ser Gly Thr Asp Phe Thr
        195                 200                 205
Leu Thr Ile Ser Ser Val Gln Ser Glu Asp Phe Ala Thr Tyr Tyr Cys
    210                 215                 220
Gln Gln Tyr Asp Ser Tyr Pro Tyr Thr Phe Gly Gly Gly Thr Lys Leu
225                 230                 235                 240
Glu Ile Lys Ser Gly Gly Gly Gly Ser Glu Val Gln Leu Val Glu Ser
                245                 250                 255
Gly Gly Gly Leu Val Gln Pro Gly Gly Ser Leu Lys Leu Ser Cys Ala
            260                 265                 270
Ala Ser Gly Phe Thr Phe Asn Lys Tyr Ala Met Asn Trp Val Arg Gln
        275                 280                 285
Ala Pro Gly Lys Gly Leu Glu Trp Val Ala Arg Ile Arg Ser Lys Tyr
    290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
                325                 330                 335
Leu Lys Thr Glu Asp Thr Ala Val Tyr Tyr Cys Val Arg His Gly Asn
            340                 345                 350
Phe Gly Asn Ser Tyr Ile Ser Tyr Trp Ala Tyr Trp Gly Gln Gly Thr
        355                 360                 365
Leu Val Thr Val Ser Ser Gly Gly Gly Ser Gly Gly Gly Gly Ser
    370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
            420                 425                 430
Gln Ala Pro Arg Gly Leu Ile Gly Gly Thr Lys Phe Leu Ala Pro Gly
        435                 440                 445
Thr Pro Ala Arg Phe Ser Gly Ser Leu Leu Gly Gly Lys Ala Ala Leu
450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
                485                 490                 495
Val Leu His His His His His His
            500

<210> SEQ ID NO 16
<211> LENGTH: 451
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
                20                  25                  30

Glu Asp Gly Val Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln Gly
        50                  55                  60

Gly Gly Gly Ser Gly Gly Gly Ser Glu Val Gln Leu Val Glu Ser Gly
65                  70                  75                  80

Gly Gly Leu Val Gln Pro Gly Gly Ser Leu Lys Leu Ser Cys Ala Ala
                85                  90                  95

Ser Gly Phe Thr Phe Asn Lys Tyr Ala Met Asn Trp Val Arg Gln Ala
                100                 105                 110

Pro Gly Lys Gly Leu Glu Trp Val Ala Arg Ile Arg Ser Lys Tyr Asn
                115                 120                 125

Asn Tyr Ala Thr Tyr Tyr Ala Asp Ser Val Lys Asp Arg Phe Thr Ile
            130                 135                 140

Ser Arg Asp Asp Ser Lys Asn Thr Ala Tyr Leu Gln Met Asn Asn Leu
145                 150                 155                 160

Lys Thr Glu Asp Thr Ala Val Tyr Tyr Cys Val Arg His Gly Asn Phe
                165                 170                 175

Gly Asn Ser Tyr Ile Ser Tyr Trp Ala Tyr Trp Gly Gln Gly Thr Leu
                180                 185                 190

Val Thr Val Ser Ser Gly Gly Gly Gly Ser Gly Gly Gly Gly Ser Gly
                195                 200                 205

Gly Gly Gly Ser Gln Thr Val Val Thr Gln Glu Pro Ser Leu Thr Val
            210                 215                 220

Ser Pro Gly Gly Thr Val Thr Leu Thr Cys Gly Ser Ser Thr Gly Ala
225                 230                 235                 240

Val Thr Ser Gly Asn Tyr Pro Asn Trp Val Gln Gln Lys Pro Gly Gln
                245                 250                 255

Ala Pro Arg Gly Leu Ile Gly Gly Thr Lys Phe Leu Ala Pro Gly Thr
                260                 265                 270

Pro Ala Arg Phe Ser Gly Ser Leu Leu Gly Gly Lys Ala Ala Leu Thr
                275                 280                 285

Leu Ser Gly Val Gln Pro Glu Asp Glu Ala Glu Tyr Tyr Cys Val Leu
                290                 295                 300

Trp Tyr Ser Asn Arg Trp Val Phe Gly Gly Gly Thr Lys Leu Thr Val
305                 310                 315                 320

Leu Gly Gly Gly Gly Ser Gly Gly Gly Ser Glu Val Gln Leu Val Glu
                325                 330                 335

Ser Gly Gly Gly Leu Val Gln Pro Gly Asn Ser Leu Arg Leu Ser Cys
                340                 345                 350

Ala Ala Ser Gly Phe Thr Phe Ser Ser Phe Gly Met Ser Trp Val Arg
                355                 360                 365

Gln Ala Pro Gly Lys Gly Leu Glu Trp Val Ser Ser Ile Ser Gly Ser
                370                 375                 380
```

Gly Ser Asp Thr Leu Tyr Ala Asp Ser Val Lys Gly Arg Phe Thr Ile
385                 390                 395                 400

Ser Arg Asp Asn Ala Lys Thr Thr Leu Tyr Leu Gln Met Asn Ser Leu
                405                 410                 415

Arg Pro Glu Asp Thr Ala Val Tyr Tyr Cys Thr Ile Gly Gly Ser Leu
            420                 425                 430

Ser Arg Ser Ser Gln Gly Thr Leu Val Thr Val Ser Ser His His His
        435                 440                 445

His His His
    450

<210> SEQ ID NO 17
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gly Gly Gly
                245                 250                 255

Gly Ser Glu Val Gln Leu Val Glu Ser Gly Gly Gly Leu Val Gln Pro
            260                 265                 270

Gly Asn Ser Leu Arg Leu Ser Cys Ala Ala Ser Gly Phe Thr Phe Ser

```
                275                 280                 285
Ser Phe Gly Met Ser Trp Val Arg Gln Ala Pro Gly Lys Gly Leu Glu
290                 295                 300

Trp Val Ser Ser Ile Ser Gly Ser Gly Ser Asp Thr Leu Tyr Ala Asp
305                 310                 315                 320

Ser Val Lys Gly Arg Phe Thr Ile Ser Arg Asp Asn Ala Lys Thr Thr
                325                 330                 335

Leu Tyr Leu Gln Met Asn Ser Leu Arg Pro Glu Asp Thr Ala Val Tyr
                340                 345                 350

Tyr Cys Thr Ile Gly Gly Ser Leu Ser Arg Ser Ser Gln Gly Thr Leu
                355                 360                 365

Val Thr Val Ser Ser Gly Gly Gly Gly Ser Gly Gly Gly Ser Gln Val
            370                 375                 380

Gln Leu Val Gln Ser Gly Gly Gly Leu Val Gln Pro Gly Gly Ser Leu
385                 390                 395                 400

Arg Leu Ser Cys Ala Ala Ser Asp Phe Asp Phe Ala Ala Tyr Asp Met
                405                 410                 415

Ser Trp Val Arg Gln Ala Pro Gly Gln Gly Leu Glu Trp Val Ala Ile
                420                 425                 430

Ile Ser His Asp Gly Ile Asp Lys Tyr Tyr Asp Asp Ser Val Lys Gly
            435                 440                 445

Arg Phe Thr Ile Ser Arg Asp Asn Ser Lys Asn Thr Leu Tyr Leu Gln
        450                 455                 460

Met Asn Thr Leu Arg Ala Glu Asp Thr Ala Thr Tyr Gln Cys Leu Arg
465                 470                 475                 480

Leu Gly Ala Val Gly Gln Gly Thr Leu Val Thr Val Ser Ser His His
                485                 490                 495

His His His His
            500

<210> SEQ ID NO 18
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser Gly Gly Gly Gly Ser Gly Gly Gly Ser Gln Val Gln Leu
            115                 120                 125
```

Val Gln Ser Gly Gly Gly Leu Val Gln Pro Gly Gly Ser Leu Arg Leu
130                 135                 140

Ser Cys Ala Ala Ser Asp Phe Asp Phe Ala Ala Tyr Asp Met Ser Trp
145                 150                 155                 160

Val Arg Gln Ala Pro Gly Gln Gly Leu Glu Trp Val Ala Ile Ile Ser
                165                 170                 175

His Asp Gly Ile Asp Lys Tyr Tyr Asp Asp Ser Val Lys Gly Arg Phe
                180                 185                 190

Thr Ile Ser Arg Asp Asn Ser Lys Asn Thr Leu Tyr Leu Gln Met Asn
            195                 200                 205

Thr Leu Arg Ala Glu Asp Thr Ala Thr Tyr Gln Cys Leu Arg Leu Gly
210                 215                 220

Ala Val Gly Gln Gly Thr Leu Val Thr Val Ser Ser Gly Gly Gly Gly
225                 230                 235                 240

Ser Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
                260                 265                 270

Thr Phe Asn Lys Tyr Ala Met Asn Trp Val Arg Gln Ala Pro Gly Lys
            275                 280                 285

Gly Leu Glu Trp Val Ala Arg Ile Arg Ser Lys Tyr Asn Asn Tyr Ala
290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Ser
                340                 345                 350

Tyr Ile Ser Tyr Trp Ala Tyr Trp Gly Gln Gly Thr Leu Val Thr Val
            355                 360                 365

Ser Ser Gly Gly Gly Gly Ser Gly Gly Gly Ser Gly Gly Gly Gly
370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
                405                 410                 415

Gly Asn Tyr Pro Asn Trp Val Gln Gln Lys Pro Gly Gln Ala Pro Arg
                420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Thr Lys Leu Thr Val Leu His His
                485                 490                 495

His His His His
        500

<210> SEQ ID NO 19
<211> LENGTH: 500
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser Gly Gly Gly Gly Ser Gly Gly
                245                 250                 255

Gly Gly Ser Gly Gly Gly Gly Ser Gln Thr Val Val Thr Gln Glu Pro
            260                 265                 270

Ser Leu Thr Val Ser Pro Gly Gly Thr Val Thr Leu Thr Cys Gly Ser
        275                 280                 285

Ser Thr Gly Ala Val Thr Ser Gly Asn Tyr Pro Asn Trp Val Gln Gln
    290                 295                 300

Lys Pro Gly Gln Ala Pro Arg Gly Leu Ile Gly Gly Thr Lys Phe Leu
305                 310                 315                 320

Ala Pro Gly Thr Pro Ala Arg Phe Ser Gly Ser Leu Leu Gly Gly Lys
                325                 330                 335

Ala Ala Leu Thr Leu Ser Gly Val Gln Pro Glu Asp Glu Ala Glu Tyr
            340                 345                 350

Tyr Cys Val Leu Trp Tyr Ser Asn Arg Trp Val Phe Gly Gly Gly Thr
        355                 360                 365

Lys Leu Thr Val Leu Gly Gly Gly Gly Ser Gly Gly Gly Ser Gln Val
    370                 375                 380

Gln Leu Val Gln Ser Gly Gly Gly Leu Val Gln Pro Gly Gly Ser Leu
385                 390                 395                 400

```
Arg Leu Ser Cys Ala Ala Ser Asp Phe Asp Phe Ala Ala Tyr Asp Met
                405                 410                 415

Ser Trp Val Arg Gln Ala Pro Gly Gln Gly Leu Glu Trp Val Ala Ile
            420                 425                 430

Ile Ser His Asp Gly Ile Asp Lys Tyr Tyr Asp Asp Ser Val Lys Gly
        435                 440                 445

Arg Phe Thr Ile Ser Arg Asp Asn Ser Lys Asn Thr Leu Tyr Leu Gln
    450                 455                 460

Met Asn Thr Leu Arg Ala Glu Asp Thr Ala Thr Tyr Gln Cys Leu Arg
465                 470                 475                 480

Leu Gly Ala Val Gly Gln Gly Thr Leu Val Thr Val Ser Ser His His
                485                 490                 495

His His His His
        500

<210> SEQ ID NO 20
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Val Val Gln Pro Gly Arg
1               5                   10                  15

Ser Leu Arg Leu Ser Cys Ala Ala Ser Gly Phe Lys Phe Ser Gly Tyr
                20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
            35                  40                  45

Ser Thr Ile Ser Thr Ser Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115
```

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Gln Leu Thr Gln Pro Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
            35                  40                  45

Ile Tyr Asp Asp Asp Lys Arg Pro Asp Gly Val Pro Asp Arg Phe Ser
        50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                85                  90                  95

Ser Phe Asn Val Phe Gly Gly Gly Thr Lys Leu Thr Val Leu Arg
            100                 105                 110
```

<210> SEQ ID NO 25
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Thr Asp Lys Ser Thr Ser Thr Ala Tyr
```

```
                65                  70                  75                  80
Met Glu Leu Ser Ser Leu Arg Ser Glu Asp Thr Ala Thr Tyr Tyr Cys
                    85                  90                  95

Ala Arg Tyr Tyr Asp Asp His Tyr Cys Leu Asp Tyr Trp Gly Gln Gly
                100                 105                 110

Thr Thr Val Thr Val Ser Ser Gly Glu Gly Thr Ser Thr Gly Ser Gly
            115                 120                 125

Gly Ser Gly Gly Ser Gly Gly Ala Asp Asp Ile Val Leu Thr Gln Ser
        130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105

<210> SEQ ID NO 28
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 29
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60
```

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Glu Ile Val Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln His Tyr Ile Asn Trp Pro
                85                  90                  95

Leu Thr Phe Gly Gly Gly Thr Lys Val Glu Ile Lys
            100                 105

<210> SEQ ID NO 32

<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Gln Val His Tyr Asp Tyr Asn Gly Phe Pro Tyr Trp Gly
            100                 105                 110

Gln Gly Thr Leu Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg
            100                 105

<210> SEQ ID NO 34
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Lys Leu Leu Glu Ser Gly Gly Gly Leu Val Gln Pro Lys Gly
1               5                   10                  15

```
Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 35
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
                180                 185                 190

Thr Asn Lys Arg Ala Pro Gly Val Pro Ala Arg Phe Ser Gly Ser Leu
                195                 200                 205

Leu Gly Gly Lys Ala Ala Leu Thr Leu Ser Gly Ala Gln Pro Glu Asp
    210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu
                245
```

```
<210> SEQ ID NO 37
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Ala Lys Thr Thr Pro Asp Ile Val Leu
        115                 120                 125

Thr Gln Ser Pro Ala Ile Met Ser Ala Ser Pro Gly Glu Lys Val Thr
    130                 135                 140

Met Thr Cys Ser Ala Ser Ser Ser Val Ser Tyr Met Asn Trp Tyr Gln
145                 150                 155                 160

Gln Lys Ser Gly Thr Ser Pro Lys Arg Trp Ile Tyr Asp Thr Ser Lys
                165                 170                 175

Leu Ala Ser Gly Val Pro Ala His Phe Arg Gly Ser Gly Ser Gly Thr
                180                 185                 190
```

```
Ser Tyr Ser Leu Thr Ile Ser Gly Met Glu Ala Glu Asp Ala Ala Thr
        195                 200                 205

Tyr Tyr Cys Gln Gln Trp Ser Ser Asn Pro Phe Thr Phe Gly Ser Gly
    210                 215                 220

Thr Lys Leu Glu Ile Asn Arg Ala Asp Thr Ala Ala Ala Gly Ser His
225                 230                 235                 240

His His His His His
                245

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Ser Trp Val Arg Gln Ala Pro Gly Lys Gly Leu Glu Trp Val
        35                  40                  45

Ser Ser Ile Asp Phe Met Gly Pro His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Ser Met Leu Pro Met Lys Gly Lys Phe Asp Tyr
            100                 105                 110

Trp Gly Gln Gly Thr Leu Val Thr Val Ser Ser
        115                 120

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Asp Glu Tyr
            20                  25                  30

Asn Met Ser Trp Val Arg Gln Ala Pro Gly Lys Gly Leu Glu Trp Val
        35                  40                  45

Ser Thr Ile Leu Pro His Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Pro Leu Tyr Arg Phe Asp Tyr Trp Gly Gln Gly Thr
            100                 105                 110
```

```
Leu Val Thr Val Ser Ser
        115

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45

Tyr Arg Ser Ser Ser Leu Gln Ser Ala Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Thr Tyr Ala Val Pro Pro
                85                  90                  95

Thr Phe Gly Gln Gly Thr Lys Val Glu Ile Lys Arg
            100                 105

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Arg Val Pro Pro
                85                  90                  95

Thr Phe Gly Gln Gly Thr Lys Val Glu Ile Lys Arg
            100                 105

<210> SEQ ID NO 42
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115

<210> SEQ ID NO 43
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 44
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys Arg Thr
                100                 105                 110

<210> SEQ ID NO 46
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
                100                 105                 110

Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Asn

```
1               5                   10                  15
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
    115
```

<210> SEQ ID NO 48
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
1               5                   10                  15
Ala Val Gln Leu Val Glu Ser Gly Gly Gly Leu Val Gln Gly Gly Gly

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val
            35                  40                  45

Ala Thr Cys Ile Thr Val Gly Asp Ser Thr Asn Tyr Ala Asp Ser Val
            50                  55                  60

Lys Gly Arg Phe Thr Ile Ser Met Asp Tyr Thr Lys Gln Thr Val Tyr
 65                  70                  75                  80

Leu His Met Asn Ser Leu Arg Pro Glu Asp Thr Gly Leu Tyr Tyr Cys
            85                  90                  95

Lys Ile Arg Arg Thr Trp His Ser Glu Leu Trp Gly Gln Gly Thr Gln
            100                 105                 110

Val Thr Val Ser Ser
        115
```

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units, wherein some positions may be absent

<400> SEQUENCE: 49

```
1               5                   10                  15
Gly Ser Gly Ser Gly Ser Gly Ser Gly Ser Gly Ser Gly Ser Gly Ser

Gly Ser Gly Ser
        20
```

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units, wherein some positions may be absent

<400> SEQUENCE: 50

Gly Gly Ser Gly Gly Ser Gly Gly Ser Gly Gly Ser Gly Gly Gly
1               5                   10                  15

Gly Ser Gly Gly Ser Gly Gly Ser Gly Gly Ser Gly Gly Ser
            20                  25                  30

<210> SEQ ID NO 51
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units, wherein some positions may be absent

<400> SEQUENCE: 51

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 52
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units, wherein some positions may be absent

<400> SEQUENCE: 52

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 53
<211> LENGTH: 50
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units, wherein some positions may be absent

<400> SEQUENCE: 53

Gly Gly Ser Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Gly Ser Gly Gly Gly Gly Ser
        35                  40                  45

Gly Gly
    50

<210> SEQ ID NO 54
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units, wherein some positions may be absent

<400> SEQUENCE: 54

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser
    50

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Gly Ser Gly Gly Gly Gly Ser Gly Gly Gly Ser Gly
1               5                   10                  15

Gly Gly Gly Ser
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Gly Ser Gly Gly Gly Gly Ser Gly Gly Gly Gly Ser
```

```
<210> SEQ ID NO 57
<211> LENGTH: 5
<212> TYPE: PRT
<213> ORGANISM: Unknown
<220> FEATURE:
<223> OTHER INFORMATION: Description of Unknown:
      Sortase recognition sequence

<400> SEQUENCE: 57

Leu Pro Glu Thr Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Gly Ser
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

His His His His His His
1               5

<210> SEQ ID NO 60
<211> LENGTH: 6
<212> TYPE: PRT
<213> ORGANISM: Unknown
<220> FEATURE:
<223> OTHER INFORMATION: Description of Unknown:
      Sortase recognition sequence

<400> SEQUENCE: 60

Leu Pro Glu Thr Gly Gly
1               5
```

TRISPECIFIC BINDING PROTEINS AND METHODS OF USE

CROSS-REFERENCE

This application is a continuation of U.S. patent application Ser. No. 15/630,259, filed Jun. 22, 2017; which is a continuation of U.S. patent application Ser. No. 15/160,984, filed May 20, 2016 (now U.S. Pat. No. 9,708,412, issued Jul. 18, 2017); which claims the benefit of U.S. Provisional Application No. 62/305,088, filed Mar. 8, 2016; U.S. Provisional Application No. 62/165,833, filed May 22, 2015; and U.S. Provisional Application No. 62/165,153, filed May 21, 2015, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 20, 2016, is named 47517-701.301_SL.txt and is 128,516 bytes in size.

BACKGROUND OF THE INVENTION

The selective destruction of an individual cell or a specific cell type is often desirable in a variety of clinical settings. For example, it is a primary goal of cancer therapy to specifically destroy tumor cells, while leaving healthy cells and tissues intact and undamaged. One such method is by inducing an immune response against the tumor, to make immune effector cells such as natural killer (NK) cells or cytotoxic T lymphocytes (CTLs) attack and destroy tumor cells.

SUMMARY OF THE INVENTION

Provided herein are trispecific antigen-binding protein, pharmaceutical compositions thereof, as nucleic acids, recombinant expression vectors and host cells for making such trispecific antigen-binding proteins, and methods of use for the treatment of diseases, disorders, or conditions. In one aspect, described herein are trispecific antigen-binding proteins wherein said proteins comprise (a) a first domain (A) which specifically binds to human CD3; (b) a second domain (B) which is a half-life extension domain; and (c) a third domain (C) which specifically binds to a target antigen, wherein the domains are linked in the order $H_2N$-(A)-(B)-(C)-COOH, $H_2N$-(A)-(C)-(B)-COOH, $H_2N$-(B)-(A)-(C)-COOH, $H_2N$-(B)-(C)-(A)-COOH, $H_2N$-(C)-(B)-(A)-COOH, or $H_2N$-(C)-(A)-(B)-COOH by linkers L1 and L2.

Also provided herein in certain aspects are trispecific antigen-binding proteins, wherein said proteins comprise (a) a first domain (A) which specifically binds to human CD3; (b) a second domain (B) which is a half-life extension domain; and (c) a third domain (C) which specifically binds to a target antigen, wherein the domains are linked in the order $H_2N$-(A)-(C)-(B)-COOH, $H_2N$-(B)-(A)-(C)-COOH, $H_2N$-(C)-(B)-(A)-COOH, or by linkers L1 and L2.

Also provided herein in certain aspects are trispecific antigen-binding proteins, wherein said proteins comprise (a) a first domain (A) which specifically binds to human CD3; (b) a second domain (B) which is a half-life extension domain; and (c) a third domain (C) which specifically binds to a target antigen, wherein the domains are linked in the order $H_2N$-(A)-(B)-(C)-COOH, $H_2N$-(A)-(C)-(B)-COOH, $H_2N$-(B)-(A)-(C)-COOH, $H_2N$-(B)-(C)-(A)-COOH, $H_2N$-(C)-(B)-(A)-COOH, or $H_2N$-(C)-(A)-(B)-COOH by linkers L1 and L2, and wherein the first domain binds to human CD3 with a KD of greater than 100 nM.

Also provided herein in certain aspects are trispecific antigen-binding proteins, wherein said proteins comprise (a) a first domain (A) which specifically binds to human CD3; (b) a second domain (B) which is a half-life extension domain; and (c) a third domain (C) which specifically binds to a target antigen, wherein the domains are linked in the order $H_2N$-(A)-(B)-(C)-COOH, $H_2N$-(A)-(C)-(B)-COOH, $H_2N$-(B)-(A)-(C)-COOH, $H_2N$-(B)-(C)-(A)-COOH, $H_2N$-(C)-(B)-(A)-COOH, or $H_2N$-(C)-(A)-(B)-COOH by linkers L1 and L2, and wherein the protein has a molecular weight of less than 55 kDa.

Also provided herein in certain aspects are trispecific antigen-binding proteins, wherein said proteins comprise (a) a first domain (A) which specifically binds to human CD3; (b) a second domain (B) which is a half-life extension domain; and (c) a third domain (c) which specifically binds to a target antigen, wherein the domains are linked in the order $H_2N$-(A)-(B)-(C)-COOH, $H_2N$-(A)-(C)-(B)-COOH, $H_2N$-(B)-(A)-(C)-COOH, $H_2N$-(B)-(C)-(A)-COOH, $H_2N$-(C)-(B)-(A)-COOH, or $H_2N$-(C)-(A)-(B)-COOH by linkers L1 and L2, and wherein B comprises a single domain antibody that binds to serum albumin.

Various embodiments of trispecific antigen-binding proteins are also provided herein, contemplated for any aspect herein, alone or in combination. In some embodiments, first domain comprises a variable light chain and variable heavy chain each of which is capable of specifically binding to human CD3. In some embodiments, the variable light chain is a λ (lamda) light chain. In some embodiments, the variable light chain is a κ (kappa) light chain. In some embodiments, the first domain comprises a single-chain variable fragment (scFv) specific to human CD3. In some embodiments, the first domain is specific for CD3ε (epsilon). In some embodiments, the first domain is specific for CD3δ (delta). In some embodiments, the first domain is specific for CD3γ (gamma). In some embodiments, the first domain comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31. In some embodiments, the first domain is humanized or human. In some embodiments, the first domain has a KD binding of 1000 nM or less to CD3 on CD3 expressing cells. In some embodiments, the first domain has a KD binding of 100 nM or less to CD3 on CD3 expressing cells. In some embodiments, the first domain has a KD binding of 10 nM or less to CD3 on CD3 expressing cells. In some embodiments, the first domain has crossreactivity with cynomolgus CD3. In some embodiments, the first domain comprises an amino acid sequence provided herein.

In some embodiments, the second domain binds human serum albumin. In some embodiments, the second domain comprises a scFv, a variable heavy domain (VH), a variable light domain (VL), a single domain antibody, a peptide, a ligand, or a small molecule. In some embodiments, the second domain comprises a scFv. In some embodiments, the second domain comprises a VH domain. In some embodiments, the second domain comprises a VL domain. In some embodiments, the second domain comprises a single domain antibody. In some embodiments, the second domain comprises a peptide. In some embodiments, the second domain comprises a ligand. In some embodiments, the second domain comprises a small molecule entity.

In some embodiments, the third domain comprises a scFv, a VH domain, a VL domain, a non-Ig domain, a ligand, a knottin, or a small molecule entity that specifically binds to a target antigen. In some embodiments, the third domain is specific to a cell surface molecule. In some embodiments, the third domain is specific to a tumor antigen.

In some embodiments, linkers L1 and L2 are peptide linkers. In some embodiments, linkers L1 and L2 independently consist of about 20 or less amino acid residues. In some embodiments, linkers L1 and L2 are each independently selected from (GS)n (SEQ ID NO: 49), (GGS)n (SEQ ID NO: 50), (GGGS)n (SEQ ID NO: 51), (GGSG)n (SEQ ID NO: 52), (GGSGG)n (SEQ ID NO: 53), or (GGGGS)n (SEQ ID NO: 54), wherein n is 1, 2, 3, 4, 5, 6, 7, 8, 9, or 10. In some embodiments, linkers L1 and L2 are each independently (GGGGS)4 (SEQ ID NO: 55) or (GGGGS)3 (SEQ ID NO: 56). In some embodiments, linkers L1 and L2 are chemical linkers.

In some embodiments, the first domain is at the N-terminus of the protein. In some embodiments, the second domain is at the N-terminus of the protein. In some embodiments, the third domain is at the N-terminus of the protein. In some embodiments, the first domain is at the C-terminus of the protein. In some embodiments, the second domain is at the C-terminus of the protein. In some embodiments, the third domain is at the C-terminus of the protein.

In some embodiments, the protein is less than about 80 kDa. In some embodiments, the protein is about 50 to about 75 kDa. In some embodiments, the protein is less than about 50 kDa. In some embodiments, the protein is less than about 40 kDa. In some embodiments, the protein is about 20 to about 40 kDa. In some embodiments, the protein has an elimination half-time of at least about 50 hours. In some embodiments, the protein has an elimination half-time of at least about 100 hours. In some embodiments, the protein has increased tissue penetration as compared to an IgG to the same target antigen.

Also provided herein, in another aspect are polynucleotides encoding trispecific antigen-binding proteins according to any one of the above embodiments. In another aspect provided herein are vectors comprising the described polynucleotides. In another aspect, provided herein are host cells transformed with the described vectors In yet another aspect, provided herein are pharmaceutical compositions comprising a trispecific antigen-binding protein of any of the above embodiments, a polynucleotide encoding a trispecific antigen-binding protein of any of the above embodiments, a vector comprising the described polynucleotides, or a host cell transformed with a vector of any of the above embodiments and a pharmaceutically acceptable carrier.

Also provided herein, are processes for the production of trispecific antigen-binding proteins according to any of the aspects and embodiments herein, said process comprising culturing a host transformed or transfected with a vector comprising a nucleic acid sequence encoding any trispecific antigen-binding protein herein under conditions allowing the expression of the protein and recovering and purifying the produced protein from the culture.

Also provided herein are methods for the treatment amelioration of a proliferative disease, a tumorous disease, an inflammatory disease, an immunological disorder, an autoimmune disease, an infectious disease, viral disease, allergic reactions, parasitic reactions, graft-versus-host diseases or host-versus-graft diseases comprising the administration of a trispecific antigen-binding protein of any of the above embodiments to a subject in need of such a treatment or amelioration. In some embodiments, the subject is a human. In some embodiments, the method further comprises administration of an agent in combination with the trispecific antigen-binding protein described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 left, an exemplary trispecific antigen-binding protein comprising single domain antibody fragments for all its domains. FIG. 2 middle, an exemplary trispecific antigen-binding protein comprising a knottin that binds to a target antigen.

FIG. 2 right, an exemplary trispecific antigen-binding protein comprising a natural ligand that binds to a target antigen.

DETAILED DESCRIPTION OF THE INVENTION

Figure 1:
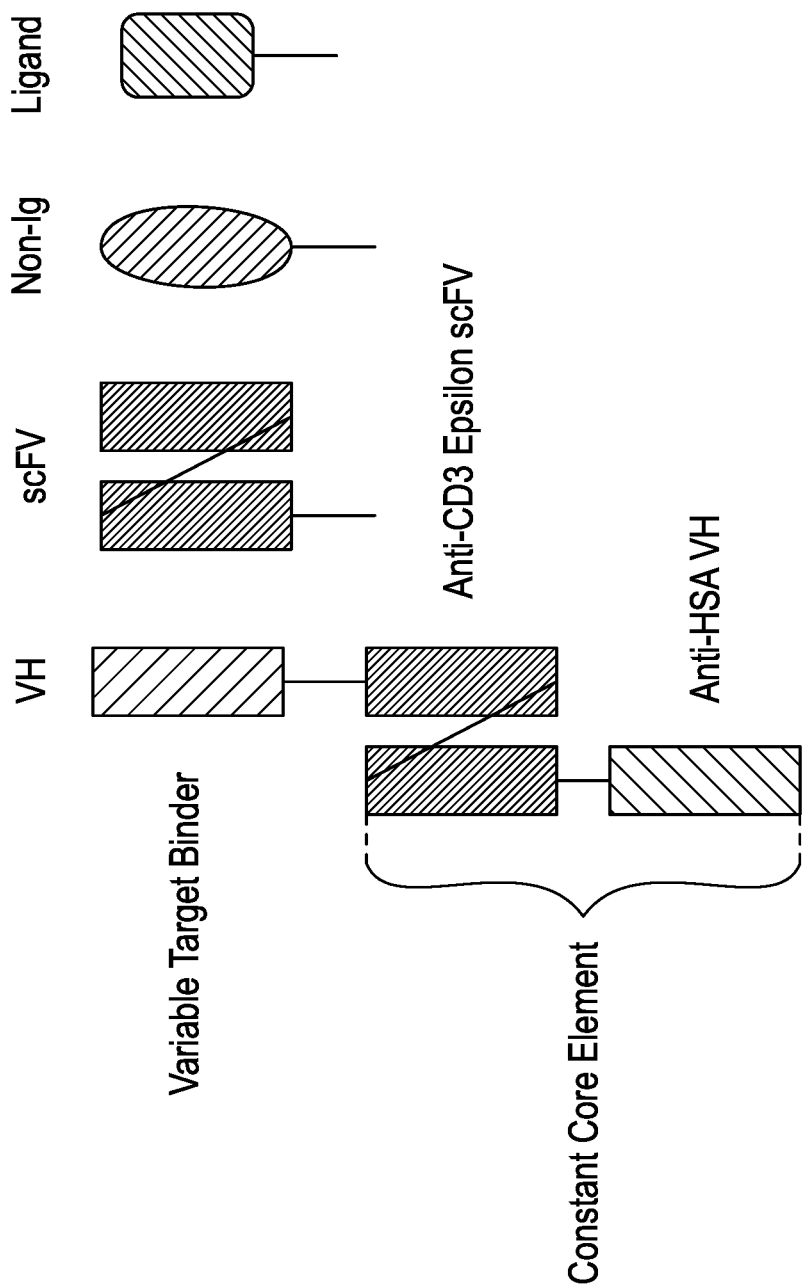
FIG. 1 is schematic representation of an exemplary trispecific antigen-binding protein where the protein has an constant core element comprising an anti-CD3ε single chain variable fragment (scFv) and an anti-HSA variable heavy chain region; and a variable target binding domain that can be a VH, scFv, a non-Ig binder, or ligand.
Figure 2:
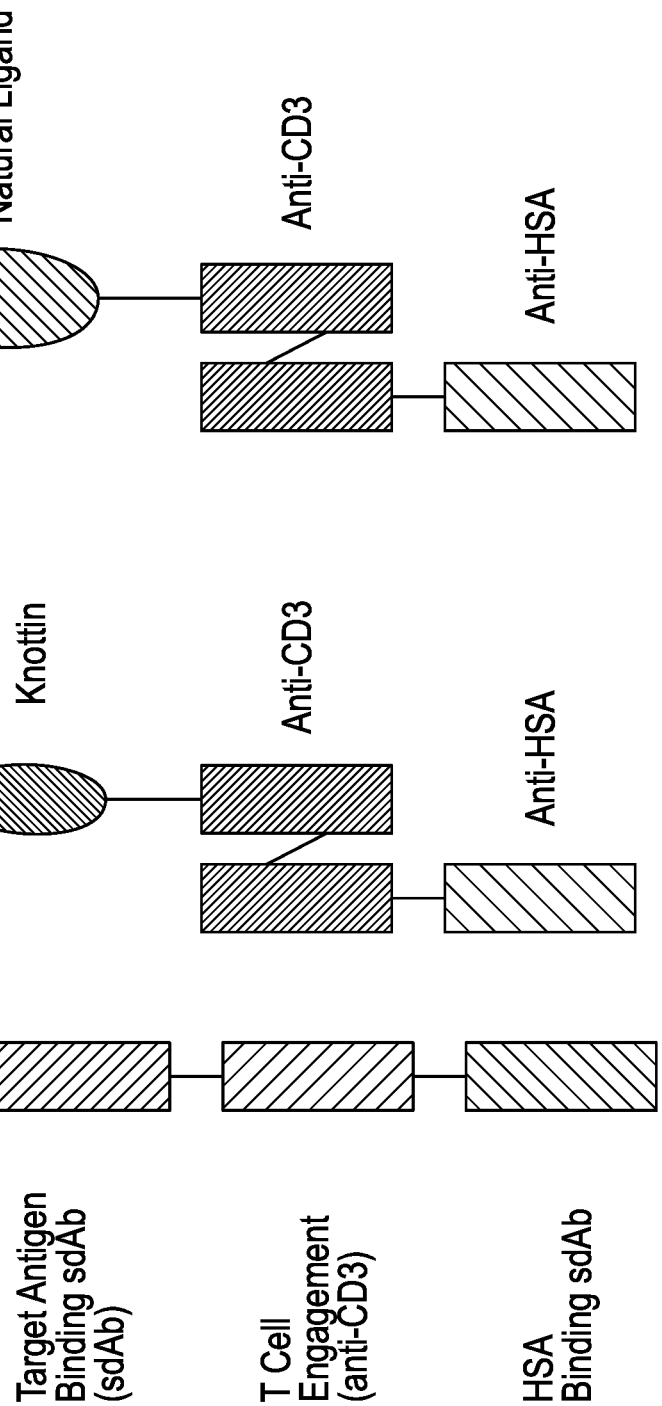
FIG. 2 is schematic representation of additional exemplary trispecific antigen-binding proteins constructed for optimal tissue penetration.
Figure 3:
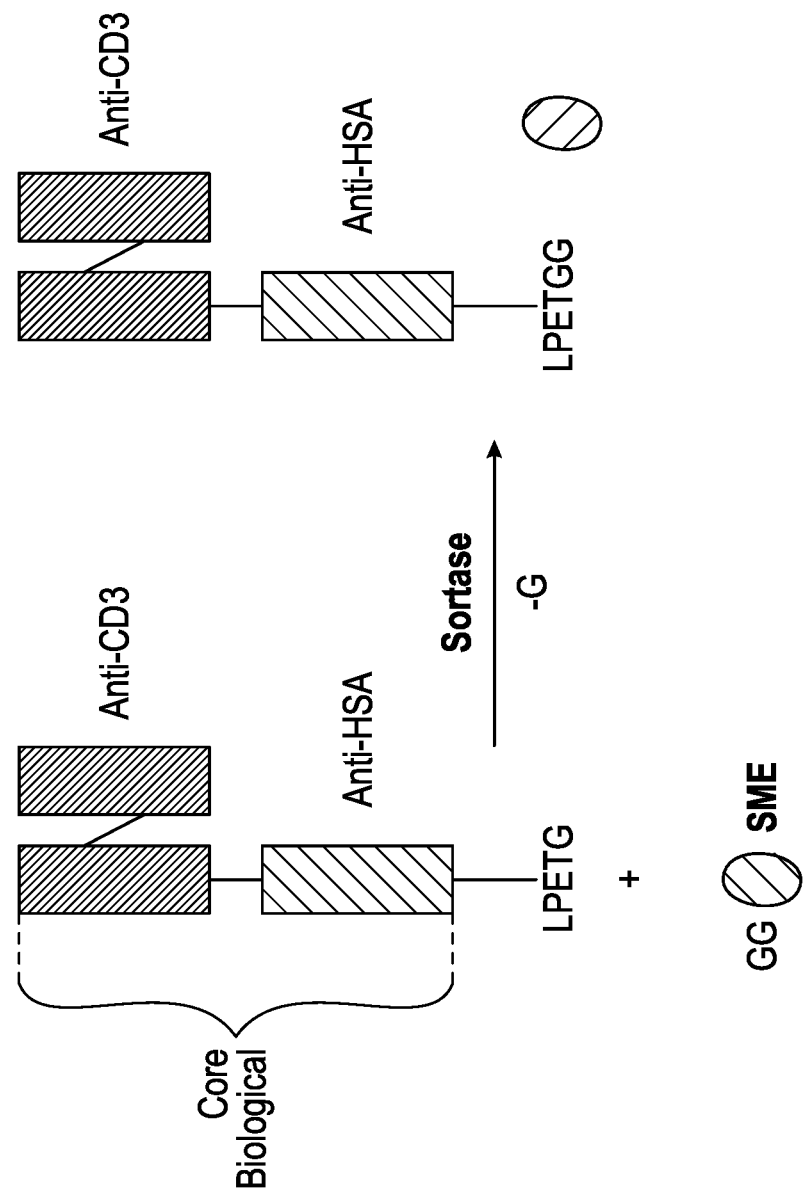
FIG. 3 is a schematic representation of attaching a small molecule entity binder to a trispecific antigen-binding protein. The trispecific antigen-binding protein comprises a sortase recognition sequence as its target antigen binding domain. Upon incubating the protein with a sortase and a glycine-attached small molecule binder, the sortase ligates or conjugates the small molecule binder onto the recognition site. Figure discloses "LPETGG" as SEQ ID NO: 60 and "LPETG" as SEQ ID NO: 57.

Described herein are trispecific antigen-binding proteins, pharmaceutical compositions thereof, as well as nucleic acids, recombinant expression vectors and host cells for making such trispecific antigen-binding proteins. Also provided are methods of using the disclosed trispecific antigen-binding proteins in the prevention, and/or treatment of diseases, conditions and disorders. The trispecific antigen-binding proteins are capable of specifically binding to a target antigen as well as CD3 and a half-life extension domain, such as a domain binding human serum albumin (HSA). FIG. 1 depicts one non-limiting example of a trispecific antigen-binding protein.

In one aspect, the trispecific antigen-binding proteins comprise a domain (A) which specifically binds to CD3, a domain (B) which specifically binds to human serum albumin (HSA), and a domain (C) which specifically binds to a target antigen. The three domains in trispecific antigen-binding proteins are arranged in any order. Thus, it is contemplated that the domain order of the trispecific antigen-binding proteins are:

H$_2$N-(A)-(B)-(C)-COOH,
H$_2$N-(A)-(C)-(B)-COOH,
H$_2$N-(B)-(A)-(C)-COOH,
H$_2$N-(B)-(C)-(A)-COOH,
H$_2$N-(C)-(B)-(A)-COOH, or
H$_2$N-(C)-(A)-(B)-COOH.

In some embodiments, the trispecific antigen-binding proteins have a domain order of H$_2$N-(A)-(B)-(C)-COOH. In some embodiments, the trispecific antigen-binding proteins have a domain order of H$_2$N-(A)-(C)-(B)-COOH. In some embodiments, the trispecific antigen-binding proteins have a domain order of H$_2$N-(B)-(A)-(C)-COOH. In some embodiments, the trispecific antigen-binding proteins have a domain order of H$_2$N-(B)-(C)-(A)-COOH. In some embodiments, the trispecific antigen-binding proteins have a domain order of H$_2$N-(C)-(B)-(A)-COOH. In some embodiments, the trispecific antigen-binding proteins have a domain order of H$_2$N-(C)-(A)-(B)-COOH.

Trispecific antigen-binding proteins described herein optionally comprise a polypeptide having a sequence described in Table 6 or Table 7 (SEQ ID NOS: 1-48) and subsequences thereof. In some embodiments, the trispecific antigen binding protein comprises a polypeptide having at least 70%-95% or more homology to a sequence described in Table 6 or Table 7 (SEQ ID NOS: 1-48). In some embodiments, the trispecific antigen binding protein comprises a polypeptide having at least 70%, 75%, 80%, 85%, 90%, 95%, or more homology to a sequence described in Table 6 or Table 7 (SEQ ID NO: 1-48). In some embodiments, the trispecific antigen binding protein has a sequence comprising at least a portion of a sequence described in Table 6 or Table 7 (SEQ ID NOS: 1-48). In some embodiments, the trispecific antigen-binding protein comprises a polypeptide comprising one or more of the sequences described in Table 6 or Table 7 (SEQ ID NOS: 1-48).

The trispecific antigen-binding proteins described herein are designed to allow specific targeting of cells expressing a target antigen by recruiting cytotoxic T cells. This improves efficacy compared to ADCC (antibody dependent cell-mediated cytotoxicity), which is using full length antibodies directed to a sole antigen and is not capable of directly recruiting cytotoxic T cells. In contrast, by engaging CD3 molecules expressed specifically on these cells, the trispecific antigen-binding proteins can crosslink cytotoxic T cells with cells expressing a target antigen in a highly specific fashion, thereby directing the cytotoxic potential of the T cell towards the target cell. The trispecific antigen-binding proteins described herein engage cytotoxic T cells via binding to the surface-expressed CD3 proteins, which form part of the TCR. Simultaneous binding of several trispecific antigen-binding protein to CD3 and to a target antigen expressed on the surface of particular cells causes T cell activation and mediates the subsequent lysis of the particular target antigen expressing cell. Thus, trispecific antigen-binding proteins are contemplated to display strong, specific and efficient target cell killing. In some embodiments, the trispecific antigen-binding proteins described herein stimulate target cell killing by cytotoxic T cells to eliminate pathogenic cells (e.g., tumor cells, virally or bacterially infected cells, autoreactive T cells, etc). In some of such embodiments, cells are eliminated selectively, thereby reducing the potential for toxic side effects. In other embodiments, the same polypeptides could be used to enhance the elimination of endogenous cells for therapeutic effect, such as B or T lymphocytes in autoimmune disease, or hematopoietic stem cells (HSCs) for stem cell transplantation.

The trispecific antigen-binding proteins described herein confer further therapeutic advantages over traditional monoclonal antibodies and other smaller bispecific molecules. Generally, the effectiveness of recombinant protein pharmaceuticals depends heavily on the intrinsic pharmacokinetics of the protein itself. One such benefit here is that the trispecific antigen-binding proteins described herein have extended pharmacokinetic elimination half-time due to having a half-life extension domain such as a domain specific to HSA. In this respect, the trispecific antigen-binding proteins described herein have an extended serum elimination half-time of about two, three, about five, about seven, about 10, about 12, or about 14 days in some embodiments. This contrasts to other binding proteins such as BiTE or DART molecules which have relatively much shorter elimination half-times. For example, the BiTE CD19×CD3 bispecific scFv-scFv fusion molecule requires continuous intravenous infusion (i.v.) drug delivery due to its short elimination half-time. The longer intrinsic half-times of the trispecific antigen-binding proteins solve this issue thereby allowing for increased therapeutic potential such as low-dose pharmaceutical formulations, decreased periodic administration and/or novel pharmaceutical compositions.

The trispecific antigen-binding proteins described herein also have an optimal size for enhanced tissue penetration and tissue distribution. Larger sizes limit or prevent penetration or distribution of the protein in the target tissues. The trispecific antigen-binding proteins described herein avoid this by having a small size that allows enhanced tissue penetration and distribution. Accordingly, the trispecific antigen-binding proteins described herein, in some embodiments have a size of about 50 kD to about 80 kD, about 50 kD to about 75 kD, about 50 kD to about 70 kD, or about 50 kD to about 65 kD. Thus, the size of the trispecific antigen-binding proteins is advantageous over IgG antibodies which are about 150 kD and the BiTE and DART diabody molecules which are about 55 kD but are not half-life extended and therefore cleared quickly through the kidney.

In further embodiments, the trispecific antigen-binding proteins described herein have an optimal size for enhanced tissue penetration and distribution. In these embodiments, the trispecific antigen-binding proteins are constructed to be as small as possible, while retaining specificity toward its targets. Accordingly, in these embodiments, the trispecific antigen-binding proteins described herein have a size of about 20 kD to about 40 kD or about 25 kD to about 35 kD to about 40 kD, to about 45 kD, to about 50 kD, to about 55 kD, to about 60 kD, to about 65 kD. In some embodiments, the trispecific antigen-binding proteins described herein have a size of about 50 kD, 49, kD, 48 kD, 47 kD, 46 kD, 45 kD, 44 kD, 43 kD, 42 kD, 41 kD, 40 kD, about 39 kD, about 38 kD, about 37 kD, about 36 kD, about 35 kD, about 34 kD, about 33 kD, about 32 kD, about 31 kD, about 30 kD, about 29 kD, about 28 kD, about 27 kD, about 26 kD, about 25 kD, about 24 kD, about 23 kD, about 22 kD, about 21 kD, or about 20 kD. An exemplary approach to the small size is through the use of single domain antibody (sdAb) fragments for each of the domains. For example, a particular trispecific antigen-binding protein has an anti-CD3 sdAb, anti-HSA sdAb and an sdAb for a target antigen. This reduces the size of the exemplary trispecific antigen-binding protein to under 40 kD. Thus in some embodiments, the domains of the trispecific antigen-binding proteins are all single domain antibody (sdAb) fragments. In other embodiments, the trispecific antigen-binding proteins described herein comprise small molecule entity (SME) binders for HSA and/or the target antigen. SME binders are small molecules averaging about 500 to 2000 Da in size and are attached to the trispecific antigen-binding proteins by known methods, such as sortase ligation or conjugation. In these instances, one of the domains of a trispecific antigen-binding protein is a sortase recognition sequence, e.g., LPETG (SEQ ID NO: 57). To attach a SE binder to a trispecific antigen-binding protein with a sortase recognition sequence, the protein is incubated with a sortase and a SE binder whereby the sortase attaches the SVE binder to the recognition sequence. Known SE binders include MIP-1072 and MIP-1095 which bind to prostate-specific membrane antigen (PSMA). In yet other embodiments, the domain which binds to a target antigen of a trispecific antigen-binding proteins described herein comprise a knottin peptide for binding a target antigen. Knottins are disulfide-stabilized peptides with a cysteine knot scaffold and have average sizes about 3.5 kD. Knottins have been contemplated for binding to certain tumor molecules such as fibronectin and VEGF-receptor. In further embodiments, domain which binds to a target antigen of a trispecific antigen-binding proteins described herein comprise a natural receptor ligand such as B-cell activating factor (BAFF/BLyS).

Another feature of the trispecific antigen-binding proteins described herein is that they are of a single-polypeptide design with flexible linkage of their domains. This allows for facile production and manufacturing of the trispecific antigen-binding proteins as they can be encoded by single cDNA molecule to be easily incorporated into a vector. Further, because the trispecific antigen-binding proteins described herein are a monomeric single polypeptide chain, there are no chain pairing issues or a requirement for dimerization. It is contemplated that the trispecific antigen-binding proteins described herein have a reduced tendency to aggregate unlike other reported molecules such as bispecific proteins with Fc-gamma immunoglobulin domains.

In the trispecific antigen-binding proteins described herein, the domains are linked by internal linkers L1 and L2, where L1 links the first and second domain of the trispecific antigen-binding proteins and L2 links the second and third domains of the trispecific antigen-binding proteins. Linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 are "short", i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 are "long", i.e., consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the trispecific antigen-binding proteins, do not interfere with the binding domains as well as resist cleavage from proteases. For example, glycine and serine residues generally provide protease resistance. Examples of internal linkers suitable for linking the domains in the trispecific antigen-binding proteins include but are not limited to $(GS)_n$ (SEQ ID NO: 49), $(GGS)_n$ (SEQ ID NO: 50), $(GGGS)_n$ (SEQ ID NO: 51), $(GGSG)_n$ (SEQ ID NO: 52), $(GGSGG)_n$ (SEQ ID NO: 53), or $(GGGGS)_n$ (SEQ ID NO: 54), wherein n is 1, 2, 3, 4, 5, 6, 7, 8, 9, or 10. In one embodiment, internal linker L1 and/or L2 is $(GGGGS)_4$ (SEQ ID NO: 55) or $(GGGGS)_3$ (SEQ ID NO: 56).

CD3 Binding Domain

The specificity of the response of T cells is mediated by the recognition of antigen (displayed in context of a major histocompatibility complex, MHC) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3 ζ (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the trispecific antigen-binding proteins described herein comprise a domain which specifically binds to CD3. In one aspect, the trispecific antigen-binding proteins described herein comprise a domain which specifically binds to human CD3. In some embodiments, the trispecific antigen-binding proteins described herein comprise a domain which specifically binds to CD3γ. In some embodiments, the trispecific antigen-binding proteins described herein comprise a domain which specifically binds to CD3δ. In some embodiments, the trispecific antigen-binding proteins described herein comprise a domain which specifically binds to CD3ε.

In further embodiments, the trispecific antigen-binding proteins described herein comprise a domain which specifically binds to the TCR. In certain instances, the trispecific antigen-binding proteins described herein comprise a domain which specifically binds the α chain of the TCR. In certain instances, the trispecific antigen-binding proteins described herein comprise a domain which specifically binds the β chain of the TCR.

In certain embodiments, the CD3 binding domain of the trispecific antigen-binding proteins described herein exhibit not only potent CD3 binding affinities with human CD3, but show also excellent crossreactivity with the respective cynomolgus monkey CD3 proteins. In some instances, the CD3 binding domain of the trispecific antigen-binding proteins are cross-reactive with CD3 from cynomolgus monkey. In certain instances, human:cynomolgous $K_D$ ratios for CD3 are between 5 and 0.2.

In some embodiments, the CD3 binding domain of the trispecific antigen-binding protein can be any domain that binds to CD3 including but not limited to domains from a monoclonal antibody, a polyclonal antibody, a recombinant antibody, a human antibody, a humanized antibody. In some instances, it is beneficial for the CD3 binding domain to be derived from the same species in which the trispecific antigen-binding protein will ultimately be used in. For example, for use in humans, it may be beneficial for the CD3 binding domain of the trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lamda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the anti-CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the anti-CD3 binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region—scFv linker-heavy chain variable region or heavy chain variable region—scFv linker-light chain variable region.

In some instances, scFvs which bind to CD3 are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow inter-chain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light chain domain and a variable heavy chain domain in a scFv include but are not limited to (GS)$_n$ (SEQ ID NO: 49), (GGS)$_n$ (SEQ ID NO: 50), (GGGS)$_n$ (SEQ ID NO: 51), (GGSG)$_n$ (SEQ ID NO: 52), (GGSGG)$_n$ (SEQ ID NO: 53), or (GGGGS)$_n$ (SEQ ID NO: 54), wherein n is 1, 2, 3, 4, 5, 6, 7, 8, 9, or 10. In one embodiment, the scFv linker can be (GGGGS)$_4$ (SEQ ID NO: 55) or (GGGGS)$_3$ (SEQ ID NO: 56). Variation in the linker length may retain or enhance activity, giving rise to superior efficacy in activity studies.

In some embodiments, CD3 binding domain of a trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of a trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of a trispecific antigen-binding protein has low affinity to CD3, i.e., about 100 nM or greater.

The affinity to bind to CD3 can be determined, for example, by the ability of the trispecific antigen-binding protein itself or its CD3 binding domain to bind to CD3 coated on an assay plate; displayed on a microbial cell surface; in solution; etc. The binding activity of the trispecific antigen-binding protein itself or its CD3 binding domain of the present disclosure to CD3 can be assayed by immobilizing the ligand (e.g., CD3) or the trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

Half-Life Extension Domain

Contemplated herein are domains which extend the half-life of an antigen-binding domain. Such domains are contemplated to include but are not limited to HSA binding domains, Fc domains, small molecules, and other half-life extension domains known in the art.

Human serum albumin (HSA) (molecular mass ~67 kDa) is the most abundant protein in plasma, present at about 50 mg/ml (600 µM), and has a half-life of around 20 days in humans. HSA serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins. For example, a recombinant fusion of an albumin binding domain to a Fab fragment resulted in an in vivo clearance of 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action.

In one aspect, the trispecific antigen-binding proteins described herein comprise a half-life extension domain, for example a domain which specifically binds to HSA. In some embodiments, the HSA binding domain of a trispecific antigen-binding protein can be any domain that binds to HSA including but not limited to domains from a monoclonal antibody, a polyclonal antibody, a recombinant antibody, a human antibody, a humanized antibody. In some embodiments, the HSA binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the HSA binding domain is a single-domain antibody. In other embodiments, the HSA binding domain is a peptide. In further embodiments, the HSA binding domain is a small molecule. It is contemplated that the HSA binding domain of a trispecific antigen-binding protein is fairly small and no more than 25 kD, no more than 20 kD, no more than 15 kD, or no more than 10 kD in some embodiments. In certain instances, the HSA binding is 5 kD or less if it is a peptide or small molecule entity.

The half-life extension domain of a trispecific antigen-binding protein provides for altered pharmacodynamics and pharmacokinetics of the trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without an half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include $K_D$ concentrations at 10 nM or less (high), between 10 nM and 100 nM (medium), and greater than 100 nM (low). As above, binding affinities to HSA are determined by known methods such as Surface Plasmon Resonance (SPR).

Target Antigen Binding Domain

In addition to the described CD3 and half-life extension domains, the trispecific antigen-binding proteins described herein also comprise a domain that binds to a target antigen. A target antigen is involved in and/or associated with a disease, disorder or condition. In particular, a target antigen associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some embodiments, a target antigen is a tumor antigen expressed on a tumor cell. Alternatively in some embodiments, a target antigen is associated with a pathogen such as a virus or bacterium.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

The design of the trispecific antigen-binding proteins described herein allows the binding domain to a target antigen to be flexible in that the binding domain to a target antigen can be any type of binding domain, including but not limited to, domains from a monoclonal antibody, a polyclonal antibody, a recombinant antibody, a human antibody, a humanized antibody. In some embodiments, the binding domain to a target antigen is a single chain variable fragments (scFv), single-domain antibody such as a heavy chain variable domain (VH), a light chain variable domain (VL) and a variable domain (VHH) of camelid derived single domain antibody. In other embodiments, the binding domain to a target antigen is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to a target antigen is a ligand or peptide that binds to or associates with a target antigen. In yet further embodiments, the binding domain to a target antigen is a knottin. In yet further embodiments, the binding domain to a target antigen is a small molecular entity.

Trispecific Protein Modifications

The trispecific antigen-binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in trispecific antigen-binding proteins described herein, including the peptide backbone, the amino acid side-chains, and the amino or carboxyl termini. Certain common peptide modifications that are useful for modification of trispecific antigen-binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding Trispecific Antigen-Binding Proteins

Also provided, in some embodiments, are polynucleotide molecules encoding a trispecific antigen-binding protein described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. In the embodiments where the target antigen binding domain is a small molecule, the polynucleotides contain genes encoding the CD3 binding domain and the half-life extension domain. In the embodiments where the half-life extension domain is a small molecule, the polynucleotides contain genes encoding the domains that bind to CD3 and the target antigen. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described trispecific antigen-binding protein. Examples of expression vectors for expression in *E. coli* are pSKK (Le Gall et al., J Immunol Methods. (2004) 285(1):111-27) or pcDNA5 (Invitrogen) for expression in mammalian cells.

Thus, the trispecific antigen-binding proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising a trispecific antigen-binding protein described herein, a vector comprising the polynucleotide encoding the polypeptide of the trispecific antigen-binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the trispecific antigen-binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the trispecific antigen-binding protein is attached to liposomes. In some instances, the trispecific antigen-binding protein are conjugated to the surface of liposomes. In some instances, the trispecific antigen-binding protein are encapsulated within the shell of a liposome. In some instances, the liposome is a cationic liposome.

The trispecific antigen-binding proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods of Treatment

Also provided herein, in some embodiments, are methods and uses for stimulating the immune system of an individual in need thereof comprising administration of a trispecific antigen-binding protein described herein. In some instances, the administration of a trispecific antigen-binding protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof a trispecific antigen-binding protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. In one instance, the cancer is a hematological cancer. In another instance, the cancer is a solid tumor cancer.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the trispecific antigen-binding proteins are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the trispecific antigen-binding proteins are administered in combination with anti-diarrheal agents, anti-emetic agents, analgesics, opioids and/or non-steroidal anti-inflamatory agents. In some embodiments, the trispecific antigen-binding proteins are administered before, during, or after surgery.

Certain Definitions

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2}=0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

EXAMPLES

Example 1: Construction of an Exemplary Trispecific Antigen-Binding Protein to CD20

Generation of a scFv CD3 Binding Domain

The human CD3ε chain canonical sequence is Uniprot Accession No. P07766. The human CD3γ chain canonical sequence is Uniprot Accession No. P09693. The human CD3δ chain canonical sequence is Uniprot Accession No. P043234. Antibodies against CD3ε, CD3γ or CD3δ are generated via known technologies such as affinity maturation. Where murine anti-CD3 antibodies are used as a starting material, humanization of murine anti-CD3 antibodies is desired for the clinical setting, where the mouse-specific residues may induce a human-anti-mouse antigen (HAMA) response in subjects who receive treatment of a trispecific antigen-binding protein described herein. Humanization is accomplished by grafting CDR regions from murine anti-CD3 antibody onto appropriate human germline acceptor frameworks, optionally including other modifications to CDR and/or framework regions. As provided herein, antibody and antibody fragment residue numbering follows Kabat (Kabat E. A. et al, 1991; Chothia et al, 1987).

Human or humanized anti-CD3 antibodies are therefore used to generate scFv sequences for CD3 binding domains of a trispecific antigen-binding protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO: 58) or "G$_4$S" (SEQ ID NO: 58) subunit (G$_4$S)$_3$ (SEQ ID NO: 56) connect the variable domains to create the scFv domain. Anti-CD3 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD3-expressing cells.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoetic stem cells, activated B lymphocytes (plasma cells) and normal tissue. As such, several antibodies mostly of murine origin have been described: 1F5, 2B8/C2B8, 2H7, and 1H4.

A scFv binding domain to CD20 is generated similarly to the above method for generation of a scFv binding domain to CD3.

Cloning of DNA Expression Constructs Encoding the Trispecific Antigen-Binding Protein The anti-CD3 scFv domains are used to construct a trispecific antigen-binding protein in combination with an anti-CD20 scFv domain and a HSA binding domain (e.g, a peptide or VH domain), with the domains organized as shown FIG. 1. For expression of a trispecific antigen-binding protein in CHO cells, coding sequences of all protein domains are cloned into a mammalian expression vector system. In brief, gene sequences encoding the CD3 binding domain, HSA binding domain, and CD20 binding domain along with peptide linkers L1 and L2 are separately synthesized and subcloned. The resulting constructs are then ligated together in the order of 'CD20 binding domain—L1—CD3 binding domain—L2—HSA binding domain' to yield a final construct. All expression constructs are designed to contain coding sequences for an N-terminal signal peptide and a C-terminal hexahistidine (6×His)-tag (SEQ ID NO: 59) to facilitate protein secretion and purification, respectively.

Expression of Trispecific Antigen-Binding Proteins in Stably Transfected CHO Cells A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted trispecific antigen-binding proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing trispecific antigen-binding proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Trispecific antigen-binding proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Trispecific Antigen-Binding Proteins

Trispecific antigen-binding proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 2: Determination of Antigen Affinity by Flow Cytometry

The trispecific antigen-binding proteins of Example 1 are tested for their binding affinities to human CD3$^+$ and CD20$^+$ cells and cynomolgus CD3$^+$ and CD20$^+$ cells.

CD3$^+$ and CD20$^+$ cells are incubated with 100 μL of serial dilutions of the trispecific antigen-binding proteins of Example 1. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the trispecific antigen-binding proteins. The cells were then washed again and resuspended in 0.2 mL of FACS buffer containing 2 μg/mL propidium iodide (PI) in order to exclude dead cells. The fluorescence of $1 \times 10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are them used for calculation of the $K_D$ values with the equation for one-site binding (hyperbola) of the GraphPad Prism (version 6.00 for Windows, GraphPad Software, La Jolla California USA).

CD3 binding affinity and crossreactivity are evaluated in titration and flow cytometric experiments on $CD3^+$ Jurkat cells and the cynomolgus $CD3^+$ HSC-F cell line (JCRB, cat.:JCRB1164). CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 3: Cytotoxicity Assay

The trispecific antigen-binding protein of Example 1 is evaluated in vitro on its mediation of T cell dependent cytotoxicity to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the trispecific antigen-binding protein of Example 1. After incubation for 4 h at 37° C. in a humidified incubator, the release of the fluorescent dye from the target cells into the supernatant is determined in a spectrofluorimeter. Target cells incubated without the trispecific antigen-binding protein of Example land target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/number of living targets$_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 4: Pharmacokinetics of Trispecific Antigen-Binding Proteins

The trispecific antigen-binding protein of Example 1 is evaluated for half-time elimination in animal studies.

The trispecific antigen-binding protein is administered to cynomolgus monkeys as a 0.5 mg/kg bolus injection intramuscularly. Another cynomolgus monkey group receives a comparable protein in size with binding domains to CD3 and CD20, but lacking HSA binding. A third and fourth group receive a protein with CD3 and HSA binding domains and a protein with CD20 and HSA binding domains respectively, and both comparable in size to the trispecific antigen-binding protein. Each test group consists of 5 monkeys. Serum samples are taken at indicated time points, serially diluted, and the concentration of the proteins is determined using a binding ELISA to CD3 and/or CD20.

Pharmacokinetic analysis is performed using the test article plasma concentrations.

Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications*, 5th edition, American Pharmaceutical Assoc., Washington, D.C.

It is expected that the trispecific antigen-binding protein of Example 1 has improved pharmacokinetic parameters such as an increase in elimination half-time as compared to proteins lacking an HSA binding domain.

Example 5: Xenograft Tumor Model

The trispecific antigen-binding protein of Example 1 is evaluated in a xenograft model.

Female immune-deficient NOD/scid mice are sub-lethally irradiated (2 Gy) and subcutaneously inoculated with $4 \times 10^6$ Ramos RA1 cells into their the right dorsal flank. When tumors reach 100 to 200 mm³, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of 50 μg trispecific antigen-binding protein of Example 1 (qd×9d). Groups 1 and 2 are only treated with vehicle. Body weight and tumor volume are determined for 30 days.

It is expected that animals treated with the trispecific antigen-binding protein of Example 1 have a statistically significant delay in tumor growth in comparison to the respective vehicle-treated control group.

Example 6: Proof-of-Concept Clinical Trial Protocol for Administration of the Trispecific Antigen-Binding Protein of Example 1 to B-Cell Lymphoma Patients This is a Phase I/II clinical trial for studying the trispecific antigen-binding protein of Example 1 as a treatment for with B-cell Lymphoma.
Study Outcomes:
Primary: Maximum tolerated dose of trispecific antigen-binding protein of Example 1
Secondary: To determine whether in vitro response of trispecific antigen-binding protein of Example 1 is associated with clinical response
Phase I
The maximum tolerated dose (MTD) will be determined in the phase I section of the trial.
1.1 The maximum tolerated dose (MTD) will be determined in the phase I section of the trial.
1.2 Patients who fulfill eligibility criteria will be entered into the trial to trispecific antigen-binding protein of Example 1.
1.3 The goal is to identify the highest dose of trispecific antigen-binding protein of Example 1 that can be administered safely without severe or unmanageable side effects in participants. The dose given will depend on the number of participants who have been enrolled in the study prior and how well the dose was tolerated. Not all participants will receive the same dose.
Phase II
2.1 A subsequent phase II section will be treated at the MTD with a goal of determining if therapy with therapy of trispecific antigen-binding protein of Example 1 results in at least a 20% response rate.
Primary Outcome for the Phase II—To determine if therapy of trispecific antigen-binding protein of Example 1 results in at least 20% of patients achieving a clinical response (blast response, minor response, partial response, or complete response)
Eligibility:
Histologically confirmed newly diagnosed aggressive B-cell lymphoma according to the current World Health Organisation Classification, from 2001 to 2007
Any stage of disease.
Treatment with R-CHOP or R-CHOP like regimens (+/−transplant).
Age ≥18 years
Karnofsky performance status ≥50% or ECOG performance status 0-2
Life expectancy ≥6 weeks Example 7: Methods to Assess Binding and Cytotoxic Activities of Trispecific Antigen Binding Molecules Protein Production
Sequences of trispecific molecules were cloned into mammalian expression vector pCDNA 3.4 (Invitrogen) preceded by a leader sequence and followed by a 6× Histidine Tag (SEQ ID NO: 59). Expi293F cells (Life Technologies A14527) were maintained in suspension in Optimum Growth Flasks (Thomson) between 0.2 to 8×1e6 cells/ml in Expi293 media. Purified plasmid DNA was transfected into Expi293 cells in accordance with Expi293 Expression System Kit (Life Technologies, A14635) protocols, and maintained for 4-6 days post transfection. Conditioned media was partially purified by affinity and desalting chromatography. Trispecific proteins were subsequently polished by ion exchange or, alternatively, concentrated with Amicon Ultra centrifugal filtration units (EMD Millipore), applied to Superdex 200 size exclusion media (GE Healthcare) and resolved in a neutral buffer containing excipients. Fraction pooling and final purity were assessed by SDS-PAGE and analytical SEC.
Affinity Measurements
The affinities of the all binding domains molecules were measured by biolayer inferometry using an Octet instrument.
PSMA affinities were measured by loading human PSMA-Fc protein (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 50 seconds. EGFR and CD3 affinities were measured by loading human EGFR-Fc protein or human CD3-Flag-Fc protein, respectively, (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 300 seconds. Affinities to human serum albumin (HSA) were measured by loading biotinylated albumin onto streptavidin biosensors, then following the same kinetic parameters as for CD3 affinity measurements. All steps were performed at 30° C. in 0.25% casein in phosphate-buffered saline.
Cytotoxicity Assays
A human T-cell dependent cellular cytotoxicity (TDCC) assay is used to measure the ability of T cell engagers, including trispecific molecules, to direct T cells to kill tumor cells (Nazarian et al. 2015. J Biomol Screen. 20:519-27). In this assay, T cells and target cancer cell line cells are mixed together at a 10:1 ratio in a 384 wells plate, and varying amounts of T cell engager are added. After 48 hours, the T cells are washed away leaving attached to the plate target cells that were not killed by the T cells. To quantitate the remaining viable cells, CellTiter-Glo® Luminescent Cell Viability Assay (Promega) is used.
Cytokine Assays
AlphaLISA assays (Perkin Elmer) for TNFalpha and Interferon gamma are used to obtain evidence that T cells are activated by trispecific molecules in the presence of target cells. For this assay, primary human T cells and human tumor cells are incubated in the presence of test molecules as described under cytotoxicity assays. After 48 h of incubation, 2 microliter aliquots of the assay supernatants are analyzed according to the manufacturer's instructions.
Diffusion Assays
A layer of Matrigel (75 µL) was added to 24 well Transwell inserts (0.4 µm), after which PBS was added to the upper and lower chambers (100 and 1025 µL, respectively) and equilibrated overnight at 4° C. 100 pmol of IgG or Fab (goat anti-human Fc, Jackson ImmunoResearch) or trispecific molecules was added to the upper chamber, and diffusion of each molecule into the lower chamber was quantified over time by an ELISA specific to each molecule. IgG and Fab were captured by donkey anti-goat IgG (Jackson ImmunoResearch) that had been immobilized on ELISA plates, and were detected with a horseradish peroxidase conjugated donkey anti-goat IgG (Jackson ImmunoResearch) and TMB development. Trispecific molecules were captured by human serum albumin (Athens Research & Technology) that had been immobilized on ELISA plates, and were detected with a horseradish peroxidase conjugated anti-His antibody (Genscript) and TMB development.

Relative diffusion at each timepoint was calculated as: (concentration in the lower chamber at time=t)/(concentration in the upper chamber at time=t).

Statistically significant differences in diffusion between the IgG molecule and the Fab or trispecific molecules were identified using an unpaired t-test.

Example 8: Affinity Measurements for EGFR Targeting Trispecific Molecules

The affinities of the three binding domains in the EGFR targeting molecule were measured by biolayer inferometry using an Octet instrument and are summarized in Table 1.

Trispecific molecules in which the EGFR binding domain is located at the N-terminus of the molecule showed significantly higher affinities to EGFR, compared to trispecific molecules that contained the EGFR binding domain in the center or in the C-terminal position. Similarly, the trispecific molecules containing the albumin binding domain at the N-terminus also exhibited higher affinities to HSA than those containing albumin in the middle or C-terminal positions. In contrast, all trispecific molecules exhibited very similar affinities to human CD3, independent of the position of the binding domain within the trispecific molecule.

Example 9: Affinity Measurements for PSMA Targeting Trispecific Molecules

The affinities of the three binding domains in the PSMA targeting molecules were measured by biolayer inferometry using an Octet instrument and are summarized in Table 2.

Trispecific molecules containing the albumin binding domain at the N-terminus had higher affinities to HSA than those containing the albumin binding domain in the middle or C-terminal positions. In contrast, the position of the CD3 binding domain did not affect the affinity for its target. Likewise, the position of the PSMA binding domain had little impact on affinity, with all trispecific molecules having affinities for human PSMA within 3-fold of each other.

Example 10: Cytotoxicity Assays with Trispecific Molecules

Trispecific molecules were tested in T cell dependent cytotoxicity (TDCC) assays for their ability to induce primary human T cells to kill human tumor cells in a tumor target dependent manner.

Figure 5:
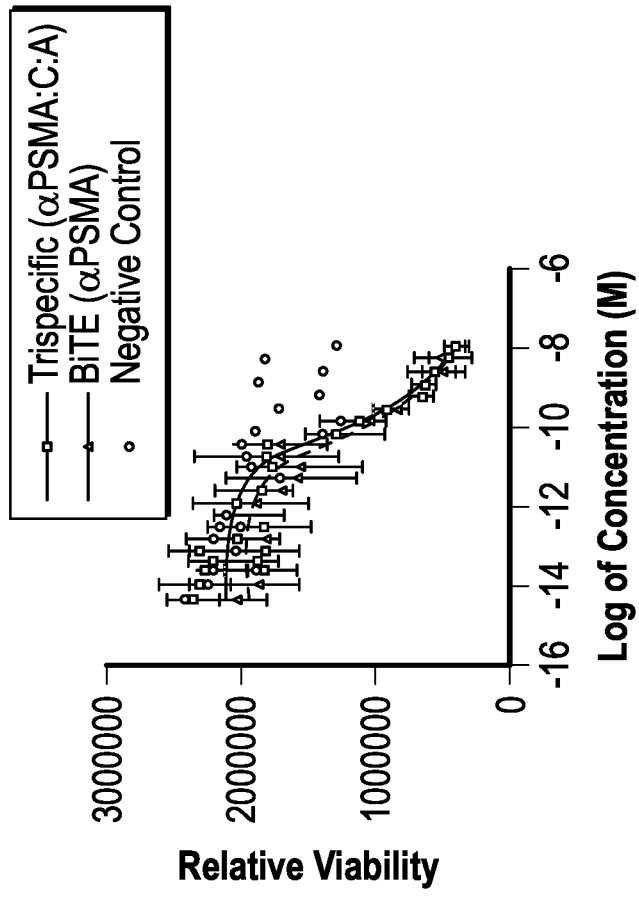
FIG. 5 compares the ability of BiTE molecules (EGFR targeting BiTE from Lutterbuese et al. 2007. PNAS 107: 12605-12610 and PSMA targeting BiTE pasotuxizumab) with the ability of EGFR and PSMA targeting VH domain containing trispecific molecules to induce primary human T cells to kill tumor cells.
Figure 5:
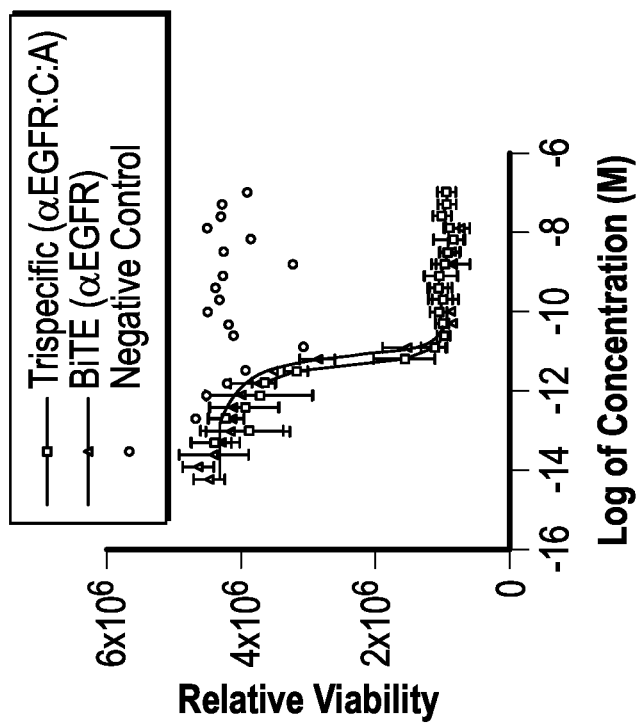

Trispecific molecules containing single domain antibody derived tumor targeting domains against EGFR or PSMA can induce potent cell killing in a manner comparable to bispecific T cell engagers (BiTE), see FIG. 5.

Figure 4:
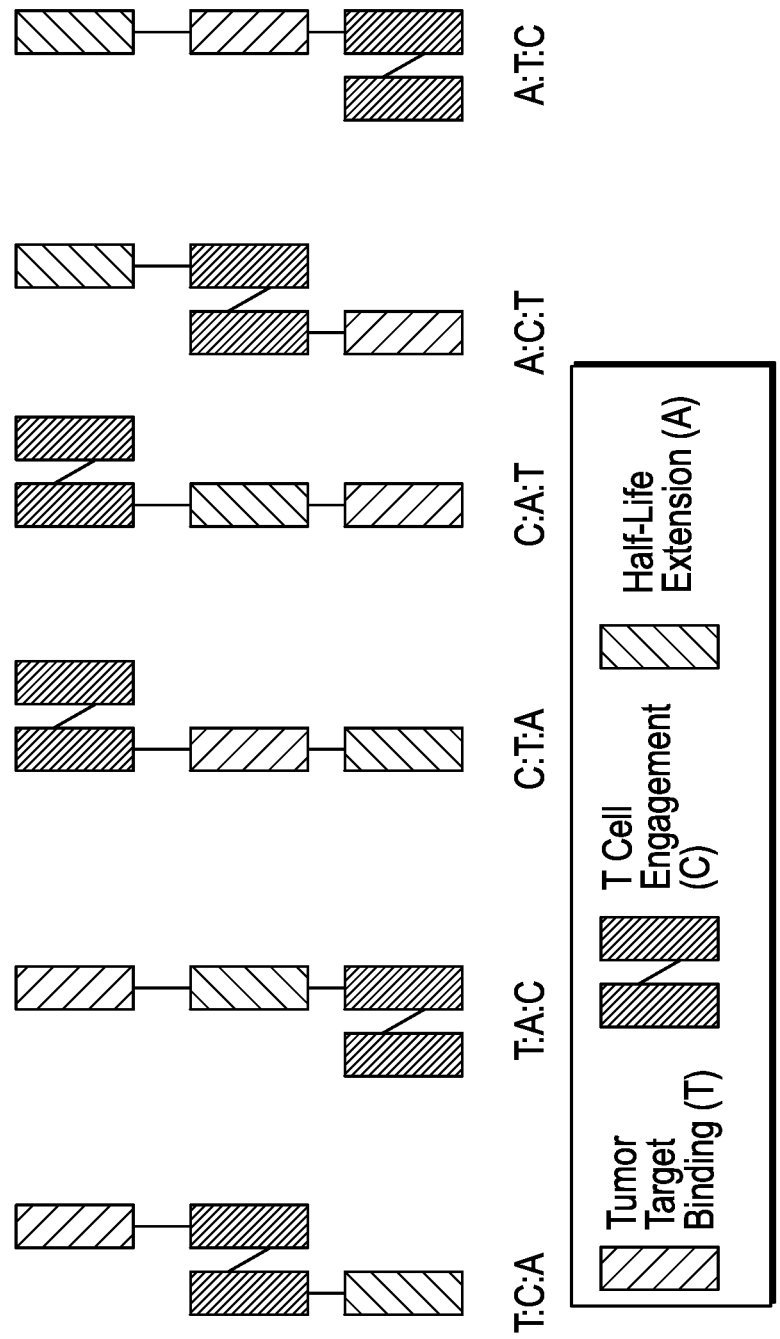
FIG. 4 is schematic representation of the six different ways in which the three domains of these trispecific antigen binding molecules can be arranged.

Six EGFR targeting trispecific molecules with a single domain anti-EGFR antibody (see FIG. 4) and a trispecific molecule containing an anti-EGFR scFv were tested in TDCC assays using NCI-1563 human lung adenocarcinoma cell line. For comparison, an EGFR BiTE was included in each assay (Lutterbuese et al. 2007. PNAS 107: 12605-12610). All 7 EFGR targeting trispecific molecule configurations were demonstrated to effectively kill target cells (see representative data in Tables 3 and 4 and FIGS. 6 and 8) with a similar potency to the EGFR BiTE. The TDCC assay was also performed with the addition of 15 mg/ml human serum albumin to assess the impact of albumin binding on the TDCC activity of the trispecific molecules. As expected, the potency of the EGFR BiTE, which lacks an albumin binding domain, was similar in the absence or presence of albumin. The potencies of the trispecific molecules decreased in the presence of albumin, but the amount of the decrease was dependent on the configuration of the molecule. The configurations whose potencies decreased the least in the presence of albumin were the EGFR-scFv:C:A and E:A:C (anti-EGFR-scFv:anti-CD3E-scFv:anti-ALB-sdAb and anti-EGFR-sdAb:anti-ALB-sdAb:anti-CD3E-scFv).

To demonstrate that the results of the EGFR targeting trispecific molecules may apply to all trispecific molecules, five PSMA targeting trispecific molecules with a single domain anti-PSMA antibody and a trispecific molecule containing an anti-PSMA scFv were tested in a TDCC assay using 22Rv1 human prostate carcinoma epithelial cell line. For comparison, a PSMA BiTE (pasotuxizumab) was included in the assay. Representative results are found in Table 5 and FIG. 7. Most of the PSMA targeting trispecific molecules had similar activity to the PSMA BiTE in the TDCC assay except for a trispecific molecule with a A:C:P configuration (anti-PSMA-sdAb:anti-CD3E-scFv:anti-ALB-sdAb). These trispecific molecules were also tested in a TDCC assay containing 15 mg/ml human serum albumin to assess the impact of albumin binding on the TDCC activity of the trispecific molecules. As expected, the potency of the PSMA BiTE, which lacks an albumin binding domain, was similar in the absence or presence of albumin. The potencies of the trispecific molecules decreased in the presence of albumin, but the amount of the decrease was dependent on the configuration of the molecule. The configurations whose potency decreased the least in the presence of albumin was the P:A:C (anti-PSMA-sdAb:anti-ALB-sdAb:anti-CD3E-scFv).

Figure 6:
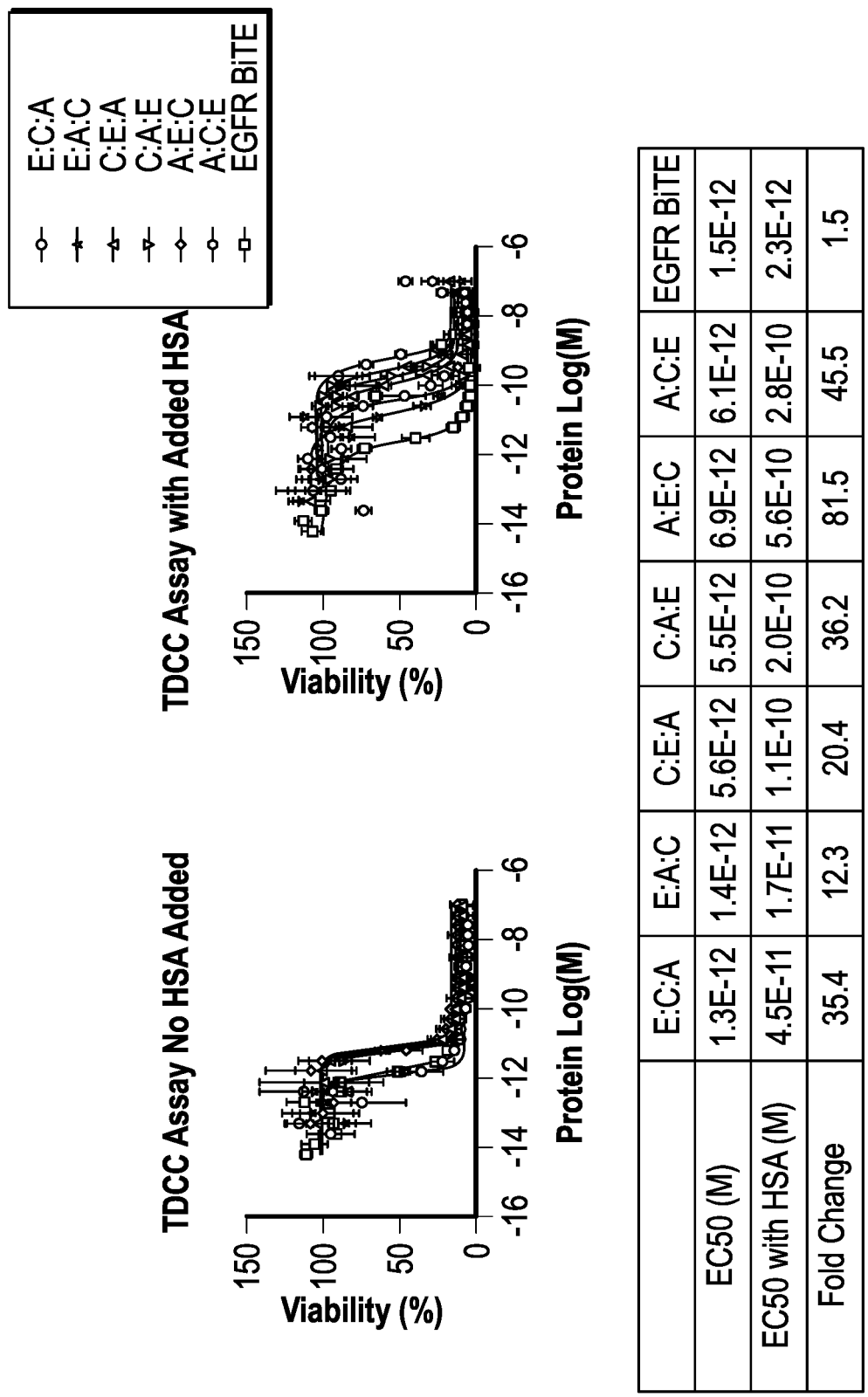
FIG. 6 shows that all six possible configurations of a trispecific molecule containing an EGFR targeting VH domain can induce T cells to kill the human tumor cell line NCI-1563. The experiment was performed in the absence (left side) and presence (right side) of human serum albumin with an EGFR targeting BiTE as positive control.
Figure 7:
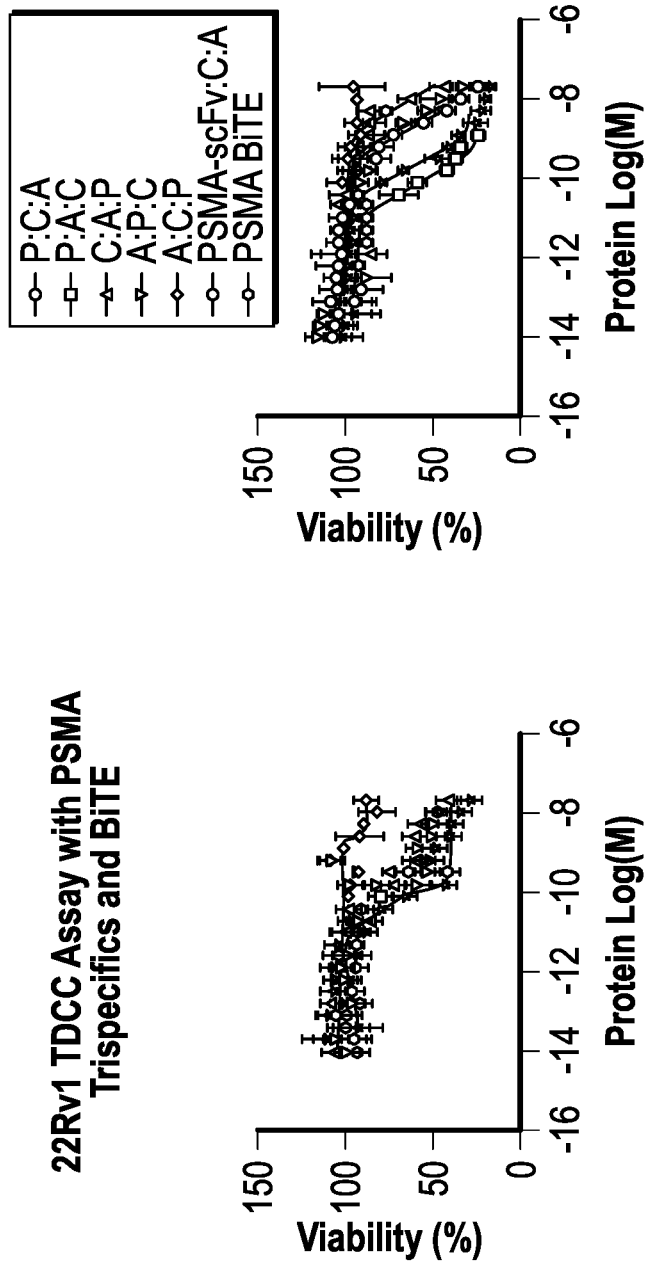
FIG. 7 assesses the ability of five possible configurations of a trispecific molecule containing a PSMA targeting VH domain to induce T cells to kill the human tumor cell line 22Rv1. The experiment was performed in the absence (left side) and presence (right side) of human serum albumin with a PSMA targeting BiTE as positive control. Also shown is the activity of a PSMA targeting trispecific molecule with a PSMA targeting scFv.
Figure 8:
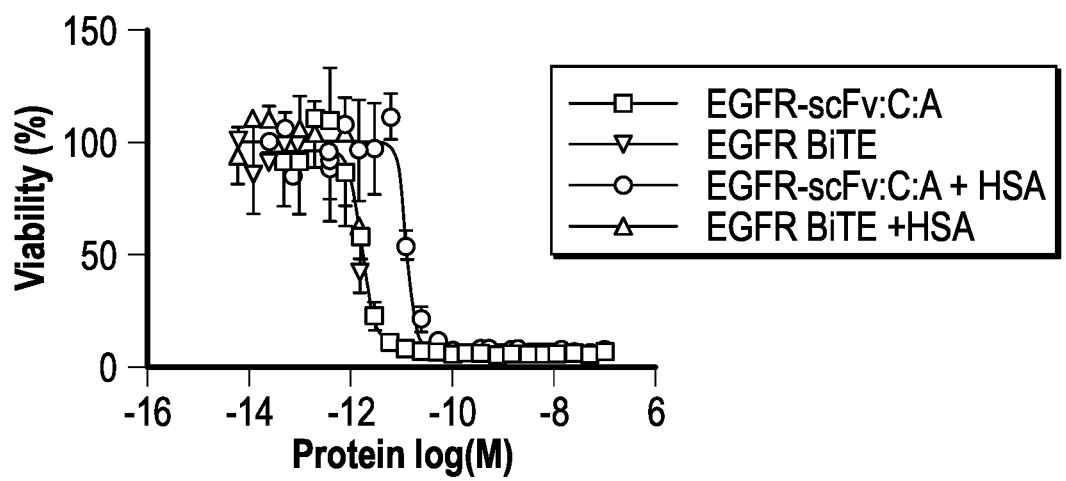
FIG. 8 shows that that the trispecific molecules can consist of a constant core element comprising an anti-CD3ε single chain variable fragment (scFv) and an anti-HSA variable heavy chain region; and a variable target binding domain that can be a scFv.
Figure 9:
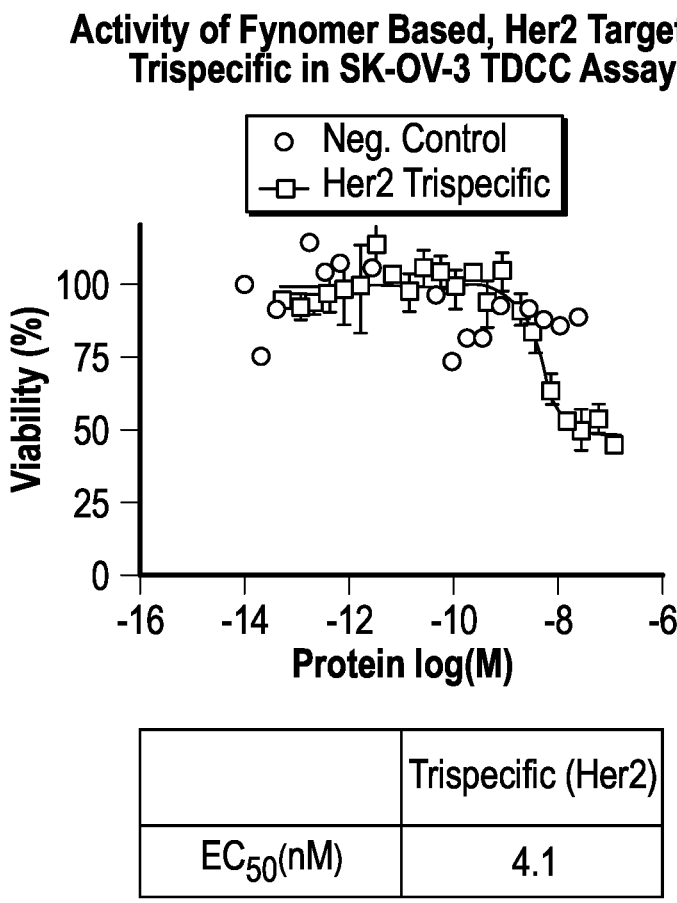
FIG. 9 demonstrates that trispecific molecules that use a fynomer as opposed to an antibody derived domain for tumor targeting can induce T cells to kill tumor cells.

The trispecific molecules described here can utilize various modalities to target tumor cells. FIGS. 5, 6 and 7 show trispecific molecules with sdAb derived tumor targeting domains, and FIGS. 7 and 8 show that trispecific molecules with a scFv derived tumor binding domain can work equally well. FIG. 9 demonstrates that the tumor targeting domain is not limited to constructs derived from antibodies like sdAbs and scFvs, but that non-immunoglobulin domains can also work. In this example, a 7 kDa fynomer specific to Her2 is used to redirect resting human T cells to kill the human ovarian cancer cells.

Example 11: Cytokine Production Assays with Trispecific Molecules

In order to show that the trispecific molecules tested here did activate T cells and redirected these T cells to kill tumor cells, the production of the cytokines TNFα and IFNγ was determined in parallel to the cell killing activity of the T cells, since T cells produce these cytokines as they get activated.

Figure 10:
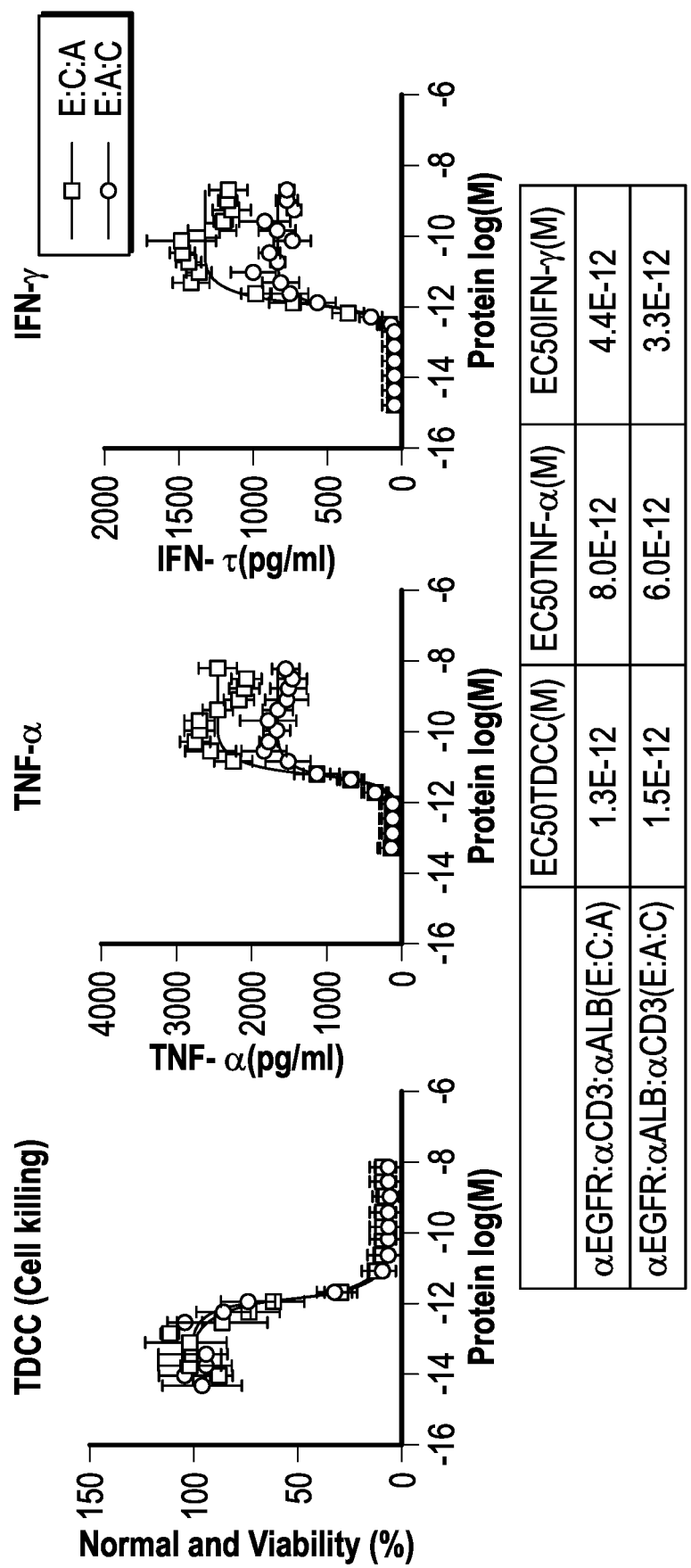
FIG. 10 shows that when EGFR targeting trispecific molecules redirect T cells to kill human CaPan2 tumor cells (panel A), the T cells get activated and produce the cytokines TNF-α (panel B) and IFNγ (panel C) in a manner dependent on the dose of the trispecific.
Figure 11:
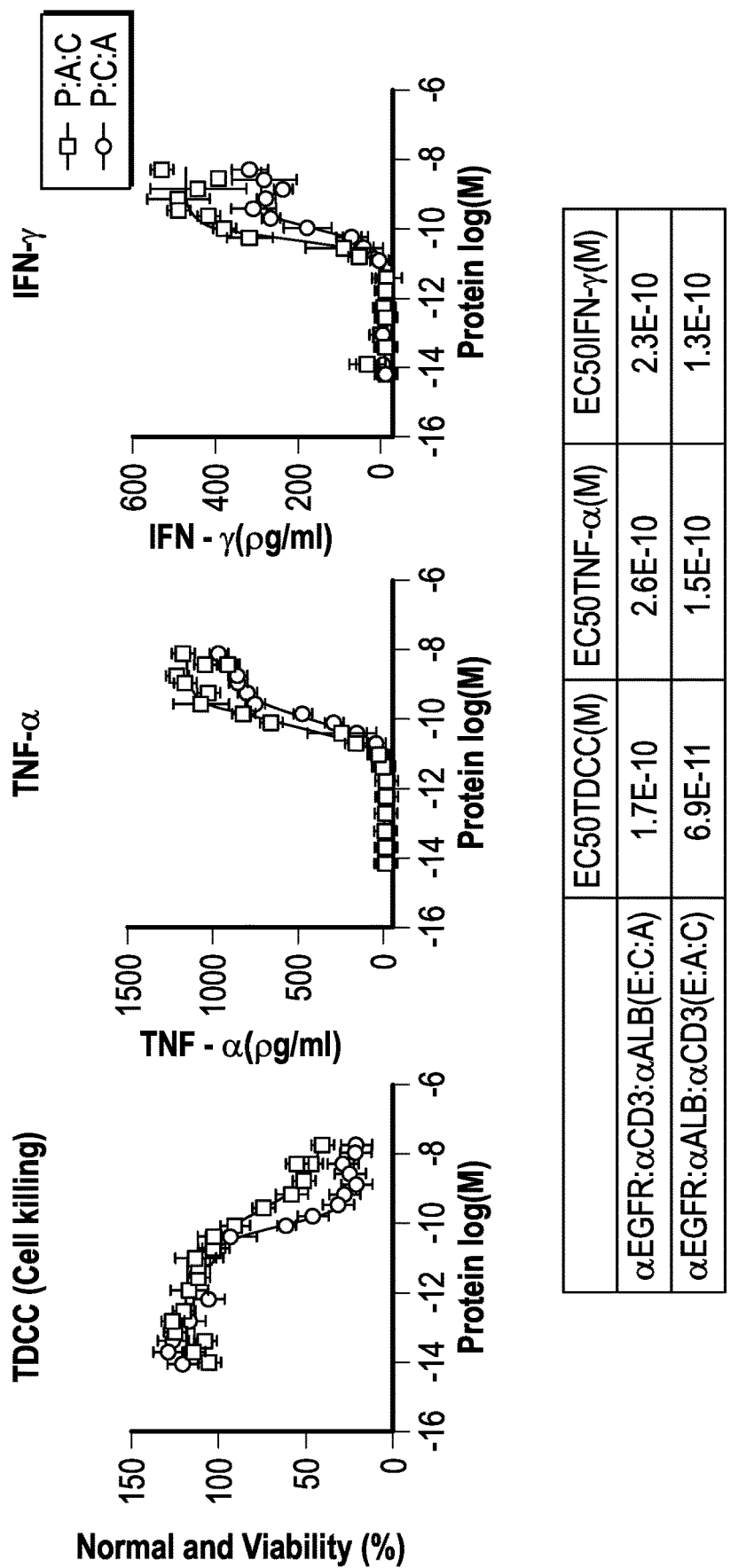
FIG. 11 shows that when PSMA targeting trispecific molecules redirect T cells to kill human 22Rv1 tumor cells (panel A), the T cells get activated and produce the cytokines TNF-α (panel B) and IFNγ (panel C) in a manner dependent on the dose of the trispecific.

As shown in FIGS. 10 and 11, the four tested EGFR and PSMA targeting trispecific molecules stimulated TNFα and Interferon γ production with potency similar to their cell killing activity. These data are consistent with the statement that the trispecific molecules activate the T Cells when engaging target cells.

Example 12: Diffusion Assays

Figure 12:
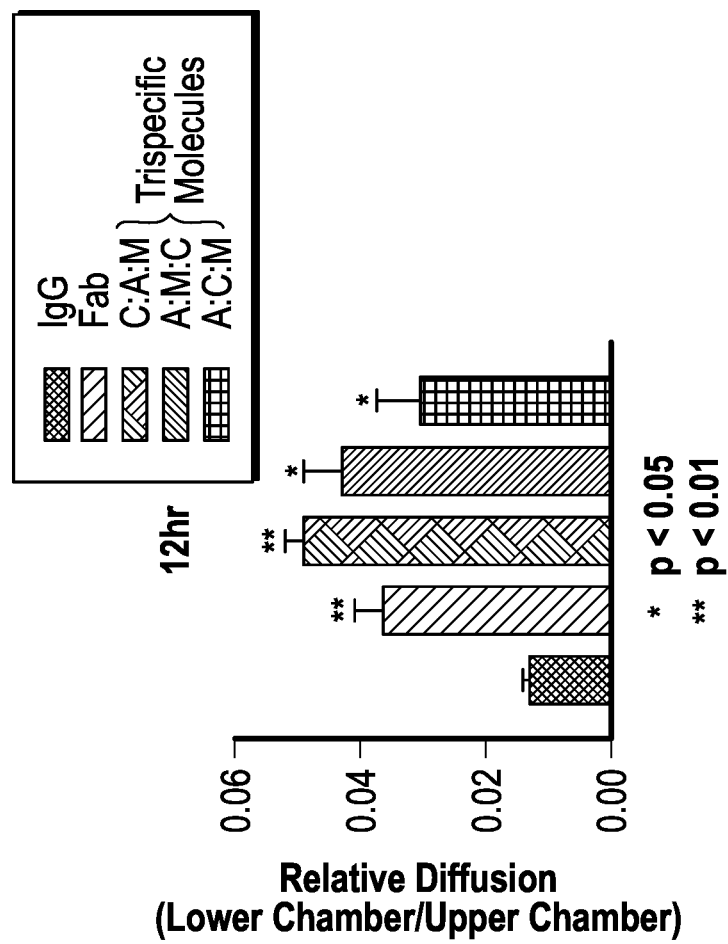
FIG. 12 shows that MSLN targeting trispecific molecules can migrate through matrigel faster than conventional antibodies.
Figure 12:
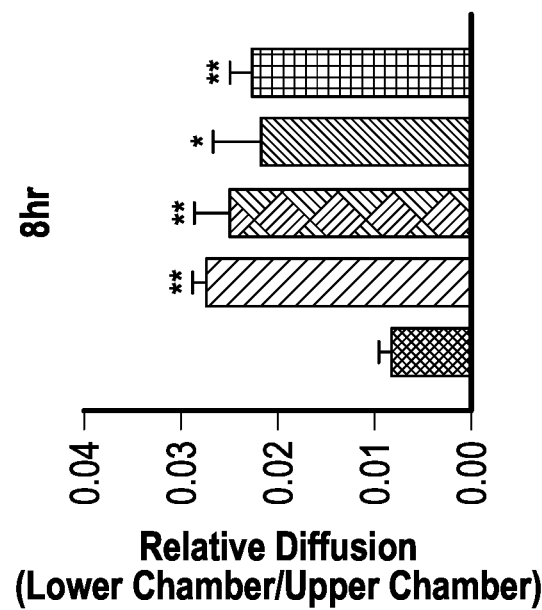

The trispecific molecules analyzed here are smaller than conventional IgG molecules, and hence are expected to diffuse faster and penetrate tissues better than monoclonal antibodies. A diffusion/migration assay through matrigel was developed to assess this property. For this purpose, transwell assay plates were coated with matrigel, a gelatinous protein mixture resembling the complex extracellular environment found in many tissues. Trispecific molecules, full length IgG or Fab fragments were added to the upper chamber. After eight and 12 hours, the lower chamber was assessed for the amount of macromolecule able to migrate through the matrix. As shown in FIG. 12, the trispecific molecules migrated at both time points at a rater much faster than full length IgG molecules.

Figure 13:
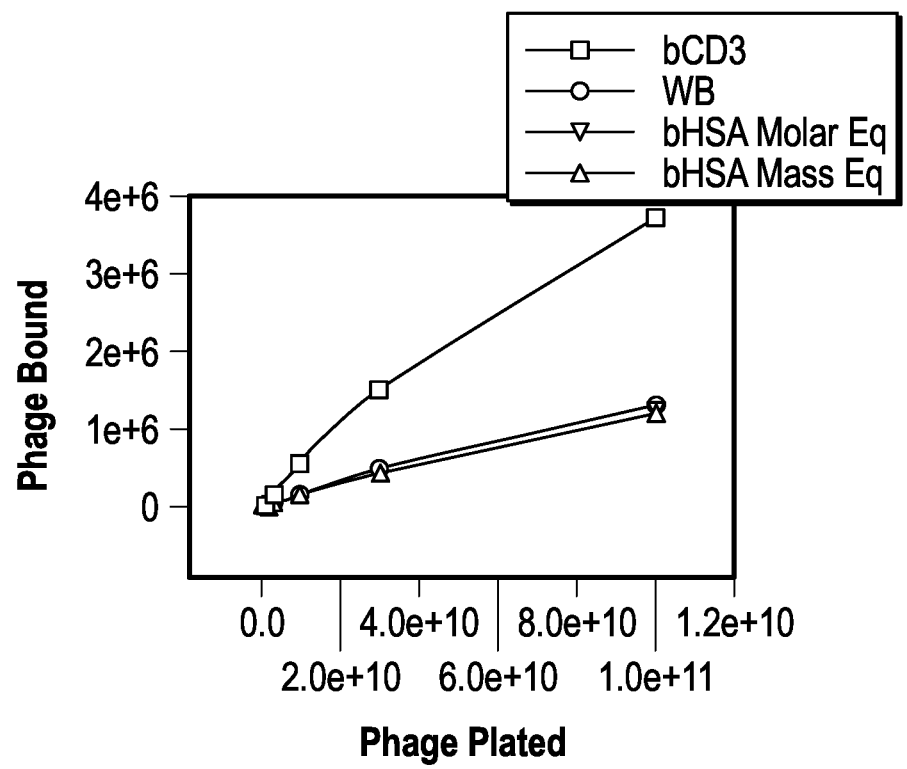
FIG. 13 shows phage titration on biotin-CD3ε and biotin-HSA.

Example 13: Identification of Anti-CD3 scFv Variants with Varying Affinities for Human CD3ε Characterization of Parental Anti-CD3ε Phage The parental anti-CD3ε showed good binding to biotin-CD3ε and low binding to biotin-HSA (FIG. 13).

Anti-CD3ε scFv Phage Libraries

A single substitution library was provided for the heavy chain CDR1, heavy chain CDR2, heavy chain CDR3, light chain CDR1, light chain CDR2, and light chain CDR3 domains. Residues were varied one at a time via mutagensis.

Selection of Clones and Determination of Binding Affinity

Single substitution libraries were bound to biotinylated hu-CD3ε, washed, eluted, and counted. Biotinylated cynoCD3 was used as the round1 selection target, and washed for 4 hours after combinatorial phage binding from the two independent libraries (~2x selection). Biotinylated hu-CD3 was used as the round 2 selection target, and washed for 3 hours after binding of both libraries (<2x selection). PCRed inserts from the second round of selection were subcloned into the pcDNA3.4 His6 expression vector. 180 clones were picked and DNA was purified, sequenced, and transfected into Expi293. A panel of sixteen clones with a range of affinities for human CD3ε were selected for more precise $K_d$ determination (Table 6).

Table 1 summarizes the affinities of trispecific molecules containing an EGFR targeting single domain antibody for the three target antigens. Key to table abbreviations: E=anti-EGFR single domain antibody, C=anti-CD3E scFv, A=anti-albumin single domain antibody.

| Trispecific Configuration | Affinity | | |
|---|---|---|---|
| | huEGFR $K_D$ (nM) | huCD3 $K_D$ (nM) | HSA $K_D$ (nM) |
| E:C:A | 0.4 | 4.7 | 22.2 |
| E:A:C | 0.8 | 4.7 | 17.7 |
| C:E:A | 44.8 | 4.0 | 17.9 |
| C:A:E | 54.5 | 4.2 | 17.2 |
| A:E:C | 48.3 | 4.5 | 4.1 |
| A:C:E | 49.1 | 3.7 | 3.8 |

Table 2 summarizes the affinities of trispecific molecules containing a PSMA targeting single domain antibody for the three target antigens. Key to table abbreviations: P=anti-PSMA single domain antibody, C=anti-CD3E scFv, A=anti-albumin single domain antibody.

| Trispecific Configuration | Affinity | | |
|---|---|---|---|
| | huPSMA $K_D$ (nM) | huCD3 $K_D$ (nM) | HSA $K_D$ (nM) |
| P:C:A | 16.7 | 3.6 | 24.0 |
| P:A:C | 31.6 | 4.1 | 21.0 |
| C:A:P | 51.0 | 4.2 | 21.7 |
| A:P:C | 25.0 | 2.1 | 3.5 |
| A:C:P | 39.7 | 2.7 | 3.5 |

Table 3 summarizes the potencies of trispecific molecules containing an EGFR targeting single domain antibody in cell killing assays. EC50 values are presented as molar concentrations. Key to table abbreviations: E=anti-EGFR single domain antibody, C=anti-CD3E scFv, A=anti-albumin single domain antibody.

| Protein | EC50 (M) | EC50 with HSA (M) | Fold change |
|---|---|---|---|
| E:C:A | 1.30E−12 | 4.50E−11 | 35.4 |
| E:A:C | 1.40E−12 | 1.70E−11 | 12.3 |
| C:E:A | 5.60E−12 | 1.10E−10 | 20.4 |
| C:A:E | 5.50E−12 | 2.00E−10 | 36.2 |
| A:E:C | 6.90E−12 | 5.60E−10 | 81.5 |
| A:C:E | 6.10E−12 | 2.80E−10 | 45.5 |
| EGFR BITE | 1.50E−12 | 2.30E−12 | 1.5 |

Table 4 summarizes the potencies of trispecific molecules containing an EGFR targeting scFv antibody and a BiTE molecule in cell killing assays. EC50 values are presented as molar concentrations. Key to table abbreviations: E=anti-EGFR single domain antibody, C=anti-CD3E scFv, A=anti-albumin single domain antibody.

| Protein | EC50 (M) | EC50 with HSA (M) | Fold change |
|---|---|---|---|
| EGFR-scFv:C:A | 1.60E−12 | 1.30E−13 | 7.8 |
| EGFR BITE | 1.30E−12 | 1.70E−12 | 1.3 |

Table 5 summarizes the potencies of trispecific molecules containing a PSMA targeting single domain antibody in cell killing assays. EC50 values are presented as molar concentrations. Key to table abbreviations: P=anti-PSMA single domain antibody, C=anti-CD3E scFv, A=anti-albumin single domain antibody.

| Protein | EC50 (M) | EC50 with HSA (M) | Fold change |
|---|---|---|---|
| P:C:A | 1.70E−10 | 2.35E−09 | 14.2 |
| P:A:C | 5.90E−11 | 2.23E−10 | 3.8 |
| C:A:P | 2.50E−10 | 1.23E−08 | 49.6 |
| A:P:C | 9.10E−11 | 4.02E−09 | 44 |
| A:C:P | inactive | inactive | |
| PSMA-scFV:C:A | 5.80E−10 | 2.00E−09 | 3.5 |
| PSMA BITE | 1.30E−10 | 6.56E−11 | 0.5 |

Table 6 summarizes binding affinities of CD3e scFv phage libraries.

| anti-CD3e scFv | KD (nM) hum CD3e | kon(1/Ms) | kdis(1/s) | KD (nM) cyno CD3e | kon(1/Ms) | kdis(1/s) | cyno/hum ratio |
|---|---|---|---|---|---|---|---|
| wt | 4.4 | 4.71E+05 | 2.07E−03 | 3.9 | 4.63E+05 | 1.83E−03 | 0.9 |
| 2B2 | 3.8 | 6.08E+05 | 2.32E−03 | 3.5 | 5.57E+05 | 1.93E−03 | 0.9 |
| 9F2 | 4.1 | 3.61E+05 | 1.33E−03 | 3.4 | 3.38E+05 | 1.05E−03 | 0.8 |
| 5A2 | 4.3 | 5.66E+05 | 2.36E−03 | 4.2 | 4.75E+05 | 1.93E−03 | 1.0 |
| 6A2 | 4.7 | 5.22E+05 | 2.48E−03 | 4.9 | 4.56E+05 | 2.22E−03 | 1.0 |
| 2D2 | 6.4 | 5.27E+05 | 3.38E−03 | 6.6 | 4.71E+05 | 3.09E−03 | 1.0 |
| 3F2 | 8.0 | 7.04E+05 | 5.02E−03 | 6.6 | 7.12E+05 | 4.38E−03 | 0.8 |
| 2E4 | 14.4 | 4.16E+05 | 5.99E−03 | 13.2 | 4.04E+05 | 5.32E−03 | 0.9 |
| 2H2 | 16.0 | 5.87E+05 | 9.06E−03 | 16.0 | 5.25E+05 | 8.37E−03 | 1.0 |
| 10B2 | 17.9 | 4.90E+05 | 8.74E−03 | 16.6 | 4.93E+05 | 8.15E−03 | 0.9 |
| 1A2 | 19.9 | 5.99E+05 | 1.19E−02 | 17 | 5.31E+05 | 9.03E−03 | 0.9 |
| 1C2 | 36.8 | 6.63E+05 | 2.44E−02 | 30 | 6.69E+05 | 1.97E−02 | 0.8 |
| 2A4 | 46.3 | 3.64E+05 | 1.66E−02 | 43.4 | 3.53E+05 | 1.53E−02 | 0.9 |
| 10E4 | 49.8 | 5.22E+05 | 2.60E−02 | 46.8 | 5.08E+05 | 2.38E−02 | 0.9 |
| 8A5 | 109 | 7.46E+05 | 8.10E−02 | 103 | 7.23E+05 | 7.44E−02 | 0.9 |
| 2G5 | 117 | 9.94E+05 | 1.15E−01 | 115 | 9.64E+05 | 1.11E−01 | 1.0 |
| 1G4 | 132.9 | 1.67E+05 | 2.20E−02 | 133.7 | 1.64E+05 | 2.19E−02 | 1.0 |

TABLE 7

Sequences

| SEQ ID NO: | Construct | Abbreviation | Sequence |
|---|---|---|---|
| 1 | αEGFR:αCD3: αAlbumin Trispecific | E:C:A | EVQLVESGGGLVQAGGSLRLSCAASGRTFSSYAMGWFRQAPGKE REFVVAINWSSGSTYYADSVKGRFTISRDNAKNTMYLQMNSLKPE DTAVYYCAAGYQINSGNYNFKDYEYDYWGQGTQVTVSSGGGGS GGGGSEVQLVESGGGLVQPGGSLKLSCAASGFTFNKYAMNWVRQ APGKGLEWVARIRSKYNNYATYYADSVKDRFTISRDDSKNTAYLQ MNNLKTEDTAVYYCVRHGNFGNSYISYWAYWGQGTLVTVSSGG GGSGGGGSGGGGSQTVVTQEPSLTVSPGGTVTLTCGSSTGAVTS GNYPNWVQQKPGQAPRGLIGGTKFLAPGTPARFSGSLLGGKAAL TLSGVQPEDEAEYYCVLWYSNRWVFGGGTKLTVLGGGGSGGGGS EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSHHHHHH |
| 2 | αEGFR: αAlbumin: αCD3 Trispecific | E:A:C | EVQLVESGGGLVQAGGSLRLSCAASGRIFSSYAMGWFRQAPGKE REFVVAINWSSGSTYYADSVKGRFTISRDNAKNTMYLQMNSLKPE DTAVYYCAAGYQINSGNYNFKDYEYDYWGQGTQVTVSSGGGGS GGGSEVQLVESGGGLVQPGNSLRLSCAASGFTFSSFGMSWVRQA PGKGLEWVSSISGSGSDTLYADSVKGRFTISRDNAKTTLYLQMNSL RPEDTAVYYCTIGGSLSRSSQGTLVTVSSGGGGSGGGSEVQLVES GGGLVQPGGSLKLSCAASGFTFNKYAMNWVRQAPGKGLEWVA RIRSKYNNYATYYADSVKDRFTISRDDSKNTAYLQMNNLKTEDTA VYYCVRHGNFGNSYISYWAYWGQGTLVTVSSGGGGSGGGGSGG GGSQTVVTQEPSLTVSPGGTVTLTCGSSTGAVTSGNYPNWVQQK PGQAPRGLIGGTKFLAPGTPARFSGSLLGGKAALTLSGVQPEDEAE YYCVLWYSNRWVFGGGTKLTVLHHHHHH |
| 3 | αCD3:αEGFR: αAlbumin Trispecific | C:E:A | EVQLVESGGGLVQPGGSLKLSCAASGFTFNKYAMNWVRQAPGK GLEWVARIRSKYNNYATYYADSVKDRFTISRDDSKNTAYLQMNNL KTEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLGGGGSGGGGSEVQL VESGGGLVQAGGSLRLSCAASGRTFSSYAMGWFRQAPGKEREFV VAINWSSGSTYYADSVKGRFTISRDNAKNTMYLQMNSLKPEDTA VYYCAAGYQINSGNYNFKDYEYDYWGQGTQVIVSSGGGGSGGG SEVQLVESGGGLVQPGNSLRLSCAASGFIFSSFGMSWVRQAPGK GLEWVSSISGSGSDTLYADSVKGRFTISRDNAKTTLYLQMNSLRPE DTAVYYCTIGGSLSRSSQGTLVTVSSHHHHHH* |
| 4 | αCD3: αAlbumin: αEGFR Trispecific | C:A:E | EVQLVESGGGLVQPGGSLKLSCAASGFTFNKYAMNWVRQAPGK GLEWVARIRSKYNNYATYYADSVKDRFTISRDDSKNTAYLQMNSG KTEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLGGGGSGGGGSEVQL VESGGGLVQPGNSLRLSCAASGFTFSSFGMSWVRQAPGKGLEW |

TABLE 7 -continued

Sequences

| SEQ ID NO: | Construct | Abbreviation | Sequence |
|---|---|---|---|
| | | | VSSISGSGSDTLYADSVKGRFTISRDNAKTTLYLQMNSLRPEDTAV YYCTIGGSLSRSSQGTLVTVSSGGGGSGGGGSEVQLVESGGGLVQA GGSLRLSCAASGRTFSSYAMGWFRQAPGKEREFVVAINWSSGST YYADSVKGRFTISRDNAKNTMYLQMNSLKPEDTAVYYCAAGYQI NSGNYNFKDYEYDYWGQGTQVTVSSHHHHHH |
| 5 | αAlbumin: αEGFR:αCD3 Trispecific | A:E:C | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGGSEVQLVESGGGL VQAGGSLRLSCAASGRTFSSYAMGWFRQAPGKEREFVVAINWSS GSTYYADSVKGRFTISRDNAKNTMYLQMNSLKPEDTAVYYCAAG YQINSGNYNFKDYEYDYWGQGTQVTVSSGGGGSGGGGSEVQLVE SGGGLVQPGGSLKLSCAASGFTFNKYAMNWVRQAPGKGLEWV ARIRSKYNNYATYYADSVKDRFTISRDDSKNTAYLQMNNLKTEDT AVYYCVRHGNFGNSYISYWAYWGQGTLVTVSSGGGGSGGGGSG GGGSQTVVTQEPSLTVSPGGTVTLTCGSSTGAVTSGNYPNWVQQ KPGQAPRGLIGGTKFLAPGTPARFSGSLLGGKAALTLSGVQPEDEA EYYCVLWYSNRWVFGGGTKLTVLHHHHHH* |
| 6 | αAlbumin: αCD3:αEGFR Trispecific | A:C:E | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGGSEVQLVESGGGL VQPGGSLKLSCAASGFTFNKYAMNWVRQAPGKGLEWVARIRSK YNNYATYYADSVKDRFTISRDDSKNTAYLQMNNLKTEDTAVYYCV RHGNFGNSYISYWAYWGQGTLVTVSSGGGGSGGGGSGGGGSQ TVVTQEPSLTVSPGGTVTLTCGSSTGAVTSGNYPNWVQQKPGQA PRGLIGGTKFLAPGTPARFSGSLLGGKAALTLSGVQPEDEAEYYCV LWYSNRWVFGGGTKLTVLGGGGSGGGGSEVQLVESGGGLVQAG GSLRLSCAASGRTFSSYAMGWFRQAPGKEREFVVAINWSSGSTYY ADSVKGRFTISRDNAKNTMYLQMNSLKPEDTAVYYCAAGYQINS GNYNFKDYEYDYWGQGTQVTVSSHHHHHH* |
| 7 | EGFR BiTE | | DILLTQSPVILSVSPGERVSFSCRASQSIGTNIHWYQQRTNGSPRLL IKYASESISGIPSRFSGSGSGTDFTLSINSVESEDIADYYCQQNNNW PTTFGAGTKLELKGGGGSGGGGSGGGGSQVQLKQSGPGLVQPS QSLSITCTVSGFSLTNYGVHWVRQSPGKGLEWLGVIWSGGNTDY NTPFTSRLSINKDNSKSQVFFKMNSLQSNDTAIYYCARALTYYDYE FAYWGQGTLVTVSASGGGGSEVQLVESGGGLVQPGGSLKLSCAA SGFTFNKYAMNWVRQAPGKGLEWVARIRSKYNNYATYYADSVK DRFTISRDDSKNTAYLQMNNLKTEDTAVYYCVRHGNFGNSYISYW AYWGQGTLVTVSSGGGGSGGGGSGGGGSQTVVTQEPSLTVSPG GTVTLTCGSSTGAVTSGNYPNWVQQKPGQAPRGLIGGTKFLAPG TPARFSGSLLGGKAALTLSGVQPEDEAEYYCVLWYSNRWVFGGG TKLTVLHHHHHH |
| 8 | EGFR-scFv:C:A | EGFR-scFv:C:A | DILLTQSPVILSVSPGERVSFSCRASQSIGTNIHWYQQRTNGSPRLL IKYASESISGIPSRFSGSGSGTDFTLSINSVESEDIADYYCQQNNNW PTTFGAGTKLELKGGGGSGGGGSGGGGSQVQLKQSGPGLVQPS QSLSITCTVSGFSLTNYGVHWVRQSPGKGLEWLGVIWSGGNTDY NTPFTSRLSINKDNSKSQVFFKMNSLQSNDTAIYYCARALTYYDYE FAYWGQGTLVTVSASGGGGSEVQLVESGGGLVQPGGSLKLSCAA SGFTFNKYAMNWVRQAPGKGLEWVARIRSKYNNYATYYADSVK DRFTISRDDSKNTAYLQMNNLKTEDTAVYYCVRHGNFGNSYISYW AYWGQGTLVTVSSGGGGSGGGGSGGGGSQTVVTQEPSLTVSPG GTVTLTCGSSTGAVTSGNYPNWVQQKPGQAPRGLIGGTKFLAPG TPARFSGSLLGGKAALTLSGVQPEDEAEYYCVLWYSNRWVFGGG TKLTVLGGGGSGGGSEVQLVESGGGLVQPGNSLRLSCAASGFTFS SFGMSWVRQAPGKGLEWVSSISGSGSDTLYADSVKGRFTISRDN AKTTLYLQMNSLRPEDTAVYYCTIGGSLSRSSQGTLVTVSSHHHHH H |
| 9 | αPSMA:αCD3: αAlbumin Trispecific | P:C:A | EVQLVESGGGLVQPGGSLTLSCAASRFMISEYSMHWVRQAPGKG LEWVSTINPAGTTDYAESVKGRFTISRDNAKNTLYLQMNSLKPED TAVYYCDGYGYRGQGTQVTVSSGGGGSGGGGSEVQLVESGGGLV QPGGSLKLSCAASGFTFNKYAMNWVRQAPGKGLEWVARIRSKY NNYATYYADSVKDRFTISRDDSKNTAYLQMNNLKTEDTAVYYCVR HGNFGNSYISYWAYWGQGTLVTVSSGGGGSGGGGSGGGGSQT VVTQEPSLTVSPGGTVTLTCGSSTGAVTSGNYPNWVQQKPGQAP RGLIGGTKFLAPGTPARFSGSLLGGKAALTLSGVQPEDEAEYYCVL WYSNRWVFGGGTKLTVLGGGGSGGGSEVQLVESGGGLVQPGN SLRLSCAASGFTFSSFGMSWVRQAPGKGLEWVSSISGSGSDTLYA DSVKGRFTISRDNAKTTLYLQMNSLRPEDTAVYYCTIGGSLSRSSQ GTLVTVSSHHHHHH |

TABLE 7-continued

Sequences

| SEQ ID NO: | Construct | Abbreviation | Sequence |
|---|---|---|---|
| 10 | αPSMA: αAlbumin: aCD3 Trispecific | P:A:C | EVQLVESGGGLVQPGGSLTLSCAASRFMISEYSMHWVRQAPGKG LEWVSTINPAGTTDYAESVKGRFTISRDNAKNTLYLQMNSLKPED TAVYYCDGYGYRGQGTQVIVSSGGGGSGGGGSEVQLVESGGGL VQPGNSLRLSCAASGFTFSSFGMSWVRQAPGKGLEWVSSISGSGS DTLYADSVKGRFTISRDNAKTTLYLQMNSLRPEDTAVYYCTIGGSL SRSSQGTLVTVSSGGGGSGGGSEVQLVESGGGLVQPGGSLKLSCA ASGFTFNKYAMNWVRQAPGKGLEWVARIRSKYNNYATYYADSV KDRFTISRDDSKNTAYLQMNNLKTEDTAVYYCVRHGNFGNSYISY WAYWGQGTLVTVSSGGGGSGGGGSGGGGSQTVVTQEPSLTVS PGGTVTLTCGSSTGAVTSGNYPNWVQQKPGQAPRGLIGGTKFLA PGTPARFSGSLLGGKAALTLSGVQPEDEAEYYCVLWYSNRWVFG GGTKLTVLHHHHHH |
| 11 | αCD3: αAlbumin: αPSMA Trispecific | C:A:P | EVQLVESGGGLVQPGGSLKLSCAASGFTFNKYAMNWVRQAPGK GLEWVARIRSKYNNYATYYADSVKDRFTISRDDSKNTAYLQMNNL KTEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLGGGGSGGGGSEVQL VESGGGLVQPGNSLRLSCAASGFTFSSFGMSWVRQAPGKGLEW VSSISGSGSDTLYADSVKGRFTISRDNAKTTLYLQMNSLRPEDTAV YYCTIGGSLSRSSQGTLVIVSSGGGGSGGGSEVQLVESGGGLVQP GGSLTLSCAASRFMISEYSMHWVRQAPGKGLEWVSTINPAGTTD YAESVKGRFTISRDNAKNTLYLQMNSLKPEDTAVYYCDGYGRGQ GTQVTVSSHHHHHH |
| 12 | αAlbumin: αPSMA:αCD3 Trispecific | A:P:C | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGSEVQLVESGGGL VQPGGSLTLSCAASRFMISEYSMHWVRQAPGKGLEWVSTINPAG TTDYAESVKGRFTISRDNAKNTLYLQMNSLKPEDTAVYYCDGYGY RGQGTQVIVSSGGGGSEVQLVESGGGLVQPGGSLKLSCAASGFT FNKYAMNWVRQAPGKGLEWVARIRSKYNNYATYYADSVKDRFTI SRDDSKNTAYLQMNNLKTEDTAVYYCVRHGNFGNSYISYWAYW GQGTLVTVSSGGGGSGGGGSGGGGSQTVVTQEPSLTVSPGGTV TLTCGSSTGAVTSGNYPNWVQQKPGQAPRGLIGGTKFLAPGTPA RFSGSLLGGKAALTLSGVQPEDEAEYYCVLWYSNRWVFGGGTKLT VLHHHHHH* |
| 13 | αAlbumin: αCD3:αPSMA Trispecific | A:C:P | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGSEVQLVESGGGL VQPGGSLKLSCAASGFTFNKYAMNWVRQAPGKGLEWVARIRSK YNNYATYYADSVKDRFTISRDDSKNTAYLQMNNLKTEDTAVYYCV RHGNFGNSYISYWAYWGQGTLVTVSSGGGGSGGGGSGGGGSQ TVVTQEPSLTVSPGGTVTLTCGSSTGAVTSGNYPNWVQQKPGQA PRGLIGGTKFLAPGTPARFSGSLLGGKAALTLSGVQPEDEAEYYCV LWYSNRWVFGGGTKLTVLGGGGSGGGSEVQLVESGGGLVQPG GSLTLSCAASRFMISEYSMHWVRQAPGKGLEWVSTINPAGTTDY AESVKGRFTISRDNAKNTLYLQMNSLKPEDTAVYYCDGYGRGQ GTQVTVSSHHHHHH* |
| 14 | αPSMA-scFv:αCD3: αAlbumin Trispecific | PSMA-scFv:C:A | QVQLVESGGGLVKPGESLRLSCAASGFTFSDYYMYWVRQAPGKG LEWVAIISDGGYYTYYSDIIKGRFTISRDNAKNSLYLQMNSLKAEDT AVYYCARGFPLLRHGAMDYWGQGTLVTVSSGGGGSGGGGSGG GGSDIQMTQSPSSLSASVGDRVTITCKASQNVDTNVAWYQQKP GQAPKSLIYSASYRYSDVPSRFSGSASGTDFTLTISSVQSEDFATYYC QQYDSYPYTFGGGTKLEIKSGGGGSEVQLVESGGGLVQPGGSLKL SCAASGFTFNKYAMNWVRQAPGKGLEWVARIRSKYNNYATYYA DSVKDRFTISRDDSKNTAYLQMNNLKTEDTAVYYCVRHGNFGNS YISYWAYWGQGTLVTVSSGGGGSGGGGSGGGGSQTVVTQEPSL TVSPGGTVTLTCGSSTGAVTSGNYPNWVQQKPGQAPRGLIGGTK FLAPGTPARFSGSLLGGKAALTLSGVQPEDEAEYYCVLWYSNRWV FGGGTKLTVLGGGGSGGGGSEVQLVESGGGLVQPGNSLRLSCAAS GFTFSSFGMSWVRQAPGKGLEWVSSISGSGSDTLYADSVKGRFTI SRDNAKTTLYLQMNSLRPEDTAVYYCTIGGSLSRSSQGTLVTVSSH HHHH |
| 15 | PSMA BiTE | | QVQLVESGGGLVKPGESLRLSCAASGFTFSDYYMYWVRQAPGKG LEWVAIISDGGYYTYYSDIIKGRFTISRDNAKNSLYLQMNSLKAEDT AVYYCARGFPLLRHGAMDYWGQGTLVTVSSGGGGSGGGGSGG GGSDIQMTQSPSSLSASVGDRVTITCKASQNVDTNVAWYQQKP GQAPKSLIYSASYRYSDVPSRFSGSASGTDFTLTISSVQSEDFATYYC QQYDSYPYTFGGGTKLEIKSGGGGSEVQLVESGGGLVQPGGSLKL SCAASGFTFNKYAMNWVRQAPGKGLEWVARIRSKYNNYATYYA |

TABLE 7 -continued

Sequences

| SEQ ID NO: | Construct | Abbreviation | Sequence |
|---|---|---|---|
| | | | DSVKDRFTISRDDSKNTAYLQMNNLKTEDTAVYYCVRHGNFGNS YISYWAYWGQGTLVTVSSGGGGSGGGGSGGGGSQTVVTQEPSL TVSPGGTVTLTCGSSTGAVTSGNYPNWVQQKPGQAPRGLIGGTK FLAPGTPARFSGSLLGGKAALTLSGVQPEDEAEYYCVLWYSNRWV FGGGTKLTVLHHHHHH |
| 16 | Her2-Fynomer:αCD3: αAlbumin Trispecific | | GVTLFVALYDYTSYNTRDLSFHKGEKFQILRMEDGVWWEARSLTT GETGYIPSNYVAPVDSIQGGGGSGGGGSEVQLVESGGGLVQPGGS LKLSCAASGFTFNKYAMNWVRQAPGKGLEWVARIRSKYNNYATY YADSVKDRFTISRDDSKNTAYLQMNNLKTEDTAVYYCVRHGNFG NSYISYWAYWGQGTLVTVSSGGGGSGGGGSGGGGSQTVVTQEP SLTVSPGGTVTLTCGSSTGAVTSGNYPNWVQQKPGQAPRGLIGG TKFLAPGTPARFSGSLLGGKAALTLSGVQPEDEAEYYCVLWYSNR WVFGGGTKLTVLGGGGSGGGGSEVQLVESGGGLVQPGNSLRLSC AASGFTFSSFGMSWVRQAPGKGLEWVSSISGSGSDTLYADSVKG RFTISRDNAKTTLYLQMNSLRPEDTAVYYCTIGGSLSRSSQGTLVTV SSHHHHHH* |
| 17 | αCD3: αAlbumin: αMSLN Trispecific | C:A:M | EVQLVESGGGLVQPGGSLKLSCAASGFTFNKYAMNWVRQAPGK GLEWVARIRSKYNNYATYYADSVKDRFTISRDDSKNTAYLQMNNL KTEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLGGGGSGGGGSEVQL VESGGGLVQPGNSLRLSCAASGFTFSSFGMSWVRQAPGKGLEW VSSISGSGSDTLYADSVKGRFTISRDNAKTTLYLQMNSLRPEDTAV YYCTIGGSLSRSSQGTLVTVSSGGGGSGGGGSQVQLVQSGGGLVQ PGGSLRLSCAASDFDFAAYDMSWVRQAPGQGLEWVAIISHDGID KYYDDSVKGRFTISRDNSKNTLYLQMNTLRAEDTATYQCLRLGAV GQGTLVTVSSHHHHHH |
| 18 | αAlbumin: αMSLN:αCD3 Trispecific | A:M:C | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGGSQVQLVQSGGG VQPGGSLRLSCAASDFDFAAYDMSWVRQAPGQGLEWVAIISHD GIDKYYDDSVKGRFTISRDNSKNTLYLQMNTLRAEDTATYQCLRLG AVGQGTLVTVSSGGGGSGGGGSEVQLVESGGGLVQPGGSLKLSCA ASGFTFNKYAMNWVRQAPGKGLEWVARIRSKYNNYATYYADSV KDRFTISRDDSKNTAYLQMNNLKTEDTAVYYCVRHGNFGNSYISY WAYWGQGTLVTVSSGGGGSGGGGSGGGGSQTVVTQEPSLTVS PGGTVTLTCGSSTGAVTSGNYPNWVQQKPGQAPRGLIGGTKFLA PGTPARFSGSLLGGKAALTLSGVQPEDEAEYYCVLWYSNRWVFG GGTKLTVLHHHHHH |
| 19 | αAlbumin: αCD3:αMSLN Trispecific | A:C:M | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSSGGGGSGGGGSEVQLVESGGGL VQPGGSLKLSCAASGFTFNKYAMNWVRQAPGKGLEWVARIRSK YNNYATYYADSVKDRFTISRDDSKNTAYLQMNNLKTEDTAVYYCV RHGNFGNSYISYWAYWGQGTLVTVSSGGGGSGGGGSGGGGSQ TVVTQEPSLTVSPGGTVTLTCGSSTGAVTSGNYPNWVQQKPGQA PRGLIGGTKFLAPGTPARFSGSLLGGKAALTLSGVQPEDEAEYYCV LWYSNRWVFGGGTKLTVLGGGGSGGGGSQVQLVQSGGGLVQPG GSLRLSCAASDFDFAAYDMSWVRQAPGQGLEWVAIISHDGIDKY YDDSVKGRFTISRDNSKNTLYLQMNTLRAEDTATYQCLRLGAVGQ GTLVTVSSHHHHHH* |

TABLE 8

Sequences

| SEQ ID NO: | Binder | Name | Chain | Sequence |
|---|---|---|---|---|
| 20 | CD3 | Anti-huCD3E-scFv | | DIKLQQSGAELARPGASVKMSCKTSGYTFTRYTMHWVKQRPGQ GLEWIGYINPSRGYTNYNQKFKDKATLTTDKSSSTAYMQLSSLTSE DSAVYYCARYYDDHYCLDYWGQGTTLTVSSVEGGSGGSGGSGG GGVDDIQLTQSPAIMSASPGEKVTMTCRASSSVSYMNWYQQKS GTSPKRWIYDTSKVASGVPYRFSGSGSGTSYSLTISSMEAEDAATY YCQQWSSNPLTFGAGTKLELK |

TABLE 8-continued

Sequences

| SEQ ID NO: | Binder | Name | Chain | Sequence |
|---|---|---|---|---|
| 21 | CD3 | Anti-huCD3E | Heavy variable | QVQLVESGGGVVQPGRSLRLSCAASGFKFSGYGMHWVRQAPGK GLEWVAVIWYDGSKKYYVDSVKGRFTISRDNSKNTLYLQMNSLR AEDTAVYYCARQMGYWHFDLWGRGTLVTVSS |
| 22 | CD3 | Anti-huCD3E | Light variable | EIVLTQSPATLSLSPGERATLSCRASQSVSSYLAWYQQKPGQAPRL LIYDASNRATGIPARFSGSGSGTDFTLTISSLEPEDFAVYYCQQRSN WPPLTFGGGTKVEIK |
| 23 | CD3 | Anti-huCD3E | Heavy variable | EVQLLESGGGLVQPGGSLRLSCAASGFTFSSFPMAWVRQAPGKG LEWVSTISTSGGRTYYRDSVKGRFTISRDNSKNTLYLQMNSLRAED TAVYYCAKFRQYSGGFDYWGQGTLVTVSS |
| 24 | CD3 | Anti-huCD3E | Light variable | DIQLTQPNSVSTSLGSTVKLSCTLSSGNIENNYVHWYQLYEGRSPT TMIYDDDKRPDGVPDRFSGSIDRSSNSAFLTIHNVAIEDEAIYFCHS YVSSFNVFGGGTKLTVLR |
| 25 | CD3 | Anti-huCD3E-scFv | | DVQLVQSGAEVKKPGASVKVSCKASGYTFTRYTMHWVRQAPGQ GLEWIGYINPSRGYTNYADSVKGRFTITTDKSTSTAYMELSSLRSED TATYYCARYYDDHYCLDYWGQGTTVTVSSGEGTSTGSGGSGGSG GADDIVLTQSPATLSLSPGERATLSCRASQSVSYMNWYQQKPGK APKRWIYDTSKVASGVPARFSGSGSGTDYSLTINSLEAEDAATYYC QQWSSNPLTFGGGTKVEIK |
| 26 | CD3 | Anti-huCD3E (humanized OKT3) | Heavy variable | QVQLVQSGGGVVQPGRSLRLSCAASGYTFTRYTMHWVRQAPGK GLEWIGYINPSRGYTNYNQKVKDRFTISRDNSKNTAFLQMDSLRP EDTGVYFCARYYDDHYCLDYWGQGTPVTVSS |
| 27 | CD3 | Anti-huCD3E (humanized OKT3) | Light variable | DIQMTQSPSSLSASVGDRVTITCSASSSVSYMNWYQQTPGKAPK RWIYDTSKLASGVPSRFSGSGSGTDYTFTISSLQPEDIATYYCQQW SSNPFTFGQGTKLQITR |
| 28 | CD3 | CD3 binder | Heavy variable | EVQLLESGGGLVQPGGSLRLSCAASGFTFSTYAMNWVRQAPGKG LEWVSRIRSKYNNYATYYADSVKGRFTISRDDSKNTLYLQMNSLRA EDTAVYYCVRHGNFGNSYVSWFAYWGQGTLVTVSS |
| 29 | CD3 | CD3 binder | Light variable | QAVVTQEPSLTVSPGGTVTLTCGSSTGAVTTSNYANWVQEKPGQ AFRGLIGGTNKRAPGTPARFSGSLLGGKAALTLSGAQPEDEAEYYC ALWYSNLWVFGGGTKLTVL |
| 30 | CD3 | CD3 binder | Heavy variable | EVQLVESGGGLVQPGRSLRLSCAASGFTFDDYTMHWVRQAPGK GLEWVSGISWNSGSIGYADSVKGRFTISRDNAKKSLYLQMNSLRA EDTALYYCAKDNSGYGHYYYGMDVWGQGTTVTVAS |
| 31 | CD3 | CD3 binder | Light variable | AEIVMTQSPATLSVSPGERATLSCRASQSVSSNLAWYQQKPGQA PRLLIYGASTRATGIPARFSGSGSGTEFTLTISSLQSEDFAVYYCQHYI NWPLTFGGGTKVEIK |
| 32 | CD3 | CD3 binder | Heavy variable | QVQLQQSGAELARPGASVKMSCKASGYTFTRSTMHWVKQRPG QGLEWIGYINPSSAYTNYNQKFKDKATLTADKSSSTAYMQLSSLTS EDSAVYYCASRQVHYDYNGFPYWGQGTLVTVSS |
| 33 | CD3 | CD3 binder | Light variable | QVVLTQSPAIMSAFPGEKVTMTCSASSSVSYMNWYQQKSGTSPK RWIYDSSKLASGVPARFSGSGSGTSYSLTISSMETEDAATYYCQQ WSRNPPTFGGGTKLQITR |
| 34 | CD3 | CD3 binder | Heavy variable | EVKLLESGGGLVQPKGSLKLSCAASGFTFNTYAMNWVRQAPGKG LEWVARIRSKYNNYATYYADSVKDRFTISRDDSQSILYLQMNNLKT EDTAMYYCVRHGNFGNSYVSWFAYWGQGTLVTVSA |
| 35 | CD3 | CD3 binder | Light variable | QAVVTQESALTTSPGETVTLTCRSSTGAVTTSNYANWVQEKPDHL FTGLIGGTNKRAPGVPARFSGSLIGDKAALTITGAQTEDEAIYFCAL WYSNLWVFGGGTKLTVLG |
| 36 | CD3 | humaninzed scFv | | EVQLVESGGGLVQPGGSLRLSCAASGFTFNTYAMNWVRQAPGK GLEWVGRIRSKYNNYATYYADVKGRFTISRDDSKNTLYLQMNSL RAEDTAVYYCVRHGNFGNSYVSWFAYWGQGTLVTVSSGGGGS GGGSGGGGSQAVVTQEPSLTVSPGGTVTLTCGSSTGAVTTSNYA NWVQQKPGQAPRGLIGGTNKRAPGVPARFSGSLLGGKAALTLSG AQPEDEAEYYCALWYSNLWVFGGGTKLTVL |
| 37 | CD3 | CD3 binder | | QVQLQQSGAELARPGASVKMSCKASGYTFTRYTMHWVKQRPG QGLEWIGYINPSRGYTNYNQKFKDKATLTTDKSSSTAYMQLSSLTS EDSAVYYCARYYDDHYSLDYWGQGTTLTVSSAKTTPDIVLTQSPAI |

TABLE 8-continued

Sequences

| SEQ ID NO: | Binder | Name | Chain | Sequence |
|---|---|---|---|---|
|  |  |  |  | MSASPGEKVTMTCSASSSVSYMNWYQQKSGTSPKRWIYDTSKLA SGVPAHFRGSGSGTSYSLTISGMEAEDAATYYCQQWSSNPFTFGS GTKLEINRADTAAAGSHHHHHH |
| 38 | HSA | VH only domain |  | EVQLLESGGGLVQPGGSLRLSCAASGFTFSKYWMSWVRQAPGK GLEWVSSIDFMGPHTYYADSVKGRFTISRDNSKNTLYLQMNSLRA EDTAVYYCAKGRTSMLPMKGKFDYWGQGTLVTVSS |
| 39 | HSA | VH only domain |  | EVQLLESGGGLVQPGGSLRLSCTASGFTFDEYNMSWVRQAPGKG LEWVSTILPHGDRTYYADSVKGRFTISRDNSKNTLYLQMNSLRAE DTAVYYCAKQDPLYRFDYWGQGTLVTVSS |
| 40 | HSA | VL only domain |  | DIQMTQSPSSLSASVGDRVTITCRASQKIATYLNWYQQKPGKAPK LLIYRSSSLQSAVPSRFSGSGSGTVFTLTISSLQPEDFATYYCQQTYA VPPTFGQGTKVEIKR |
| 41 | HSA | VL only domain |  | DIQMTQSPSSLSASVGDRVTITCRASQSISSYLNWYQQKPGKAPKL LIYRNSPLQSGVPSRFSGSGSGTDFTLTISSLQPEDFATYYCQQTYR VPPTFGQGTKVEIKR |
| 42 | HSA | MSA21 |  | QVQLQESGGGLVQPGGSLRLSCEASGFTFSRFGMTWVRQAPGK GVEWVSGISSLGDSTLYADSVKGRFTISRDNAKNTLYLQMNSLKPE DTAVYYCTIGGSLNPGGQGTQVTVSS |
| 43 | HSA | NON-NATURAL CONSENSUS ALBUMIN BINDING DOMAINS |  | LKEAKEKAIEELKKAGITSDYYFDLINKAKTVEGVNALKDEILKA |
| 44 | HSA | anti-ALB FAB | Heavy variable | EVQLLESGGGLVQPGGSLRLSCAVSGIDLSNYAINWVRQAPGKCL EWIGIIWASGTTFYATWAKGRFTISRDNSKNTVYLQMNSLRAEDT AVYYCARTVPGYSTAPYFDLWGQGTLVTVSS |
| 45 | HSA | anti-ALB FAB | Light variable | DIQMTQSPSSVSASVGDRVTITCQSSPSVWSNFLSWYQQKPGKA PKLLIYEASKLTSGVPSRFSGSGSGTDFTLTISSLQPEDFATYYCGGG YSSISDTTFGCGTKVEIKRT |
| 46 | HSA | HSA VH only |  | AVQLVESGGGLVQPGNSLRLSCAASGFTFRSFGMSWVRQAPGKE PEWVSSISGSGSDTLYADSVKGRFTISRDNAKTTLYLQMNSLKPED TAVYYCTIGGSLSRSSQGTQVTVSS |
| 47 | HSA | HSA VH only |  | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSS |
| 48 | HSA | HSA VH only |  | AVQLVESGGGLVQGGSLRLACAASERIFDLNLMGWYRQGPGN ERELVATCITVGDSTNYADSVKGRFTISMDYTKQTVYLHMNSLRPE DTGLYYCKIRRTWHSELWGQGTQVTVSS |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A trispecific antigen-binding protein, wherein said protein comprises (a) a first domain (A) which comprises a single chain variable fragment (scFv) that specifically binds to human CD3;
   (b) a second domain (B) which comprises a single domain antibody (sdAb) that binds human serum albumin, wherein the second domain comprises an amino acid sequence of SEQ ID NO: 47;
   (c) a third domain (C) which comprises a scFv or sdAb that specifically binds to a target tumor antigen that is EGFR, PSMA, HER2 or MSLN;
   wherein the domains are linked in the order H$_2$N-(C)-(B)-(A)-COOH or by linkers L1 and L2 in the order H$_2$N-(C)-L1-(B)-L2-(A)-COOH.

2. The trispecific antigen-binding protein of claim 1, wherein the first domain is humanized or human.

3. The trispecific antigen-binding protein of claim 1, wherein linkers L1 and L2 are each, independently, (GS)$_n$ (SEQ ID NO: 49), (GGS)$_n$ (SEQ ID NO: 50), (GGGS)$_n$ (SEQ ID NO: 51), (GGSG)$_n$ (SEQ ID NO: 52), (GGSGG)$_n$ (SEQ ID NO: 53), or (GGGGS)$_n$ (SEQ ID NO: 54); and wherein n is 1, 2, 3, 4, 5, 6, 7, 8, 9, or 10.

4. The trispecific antigen-binding protein of claim 1, wherein linkers L1 and L2 are each, independently, (GGGGS)$_4$ (SEQ ID NO: 55) or (GGGGS)$_3$ (SEQ ID NO: 56).

5. The trispecific antigen-binding protein of claim 1, wherein the first domain is specific for CD3ε (epsilon).

6. The trispecific antigen-binding protein of claim 1, wherein the first domain has crossreactivity with cynomolgus CD3.

7. A polynucleotide encoding the trispecific antigen-binding protein of claim 1.

8. A vector comprising the polynucleotide of claim 7.

9. A pharmaceutical composition comprising (i) the trispecific antigen-binding protein according to claim 1 and (ii) a pharmaceutically acceptable carrier.

10. A pharmaceutical composition comprising (i) the vector according to claim 8 and (ii) a pharmaceutically acceptable carrier.

11. A trispecific antigen-binding protein, wherein said protein comprises (a) a first domain (A) which comprises a single chain variable fragment (scFv) that specifically binds to human CD3;
(b) a second domain (B) which comprises a single domain antibody (sdAb) that binds human serum albumin, wherein the second domain comprises an amino acid sequence with a 90% identity to SEQ ID NO: 47;
(c) a third domain (C) which comprises a scFv or sdAb that specifically binds to a target tumor antigen that is EGFR, PSMA, HER2 or MSLN;
wherein the domains are linked in the order $H_2N$-(C)-(B)-(A)-COOH or by linkers L1 and L2.

12. The trispecific antigen-binding protein of claim 1, wherein the second domain comprises an amino acid sequence with a 95% identity to SEQ ID NO: 47.

13. The trispecific antigen-binding protein of claim 11, wherein the first domain is humanized or human.

14. The trispecific antigen-binding protein of claim 11, wherein linkers L1 and L2 are each, independently, $(GS)_n$ (SEQ ID NO: 49), $(GGS)_n$ (SEQ ID NO: 50), $(GGGS)_n$ (SEQ ID NO: 51), $(GGSG)_n$ (SEQ ID NO: 52), $(GGSGG)_n$ (SEQ ID NO: 53), or $(GGGGS)_n$ (SEQ ID NO: 54); and wherein n is 1, 2, 3, 4, 5, 6, 7, 8, 9, or 10.

15. The trispecific antigen-binding protein of claim 11, wherein linkers L1 and L2 are each, independently, $(GGGGS)_4$ (SEQ ID NO: 55) or $(GGGGS)_3$ (SEQ ID NO: 56).

16. The trispecific antigen-binding protein of claim 11, wherein the first domain is specific for CD3ε (epsilon).

17. The trispecific antigen-binding protein of claim 11, wherein the first domain has crossreactivity with cynomolgus CD3.

18. A polynucleotide encoding the trispecific antigen-binding protein of claim 11.

19. A vector comprising the polynucleotide of claim 18.

20. A pharmaceutical composition comprising (i) the trispecific antigen-binding protein according to claim 11 and (ii) a pharmaceutically acceptable carrier.

21. A pharmaceutical composition comprising (i) the vector according to claim 19 and (ii) a pharmaceutically acceptable carrier.

* * * * *